United States Patent
Tsuna et al.

(10) Patent No.: US 12,168,804 B2
(45) Date of Patent: Dec. 17, 2024

(54) LISTERIA-MONOCYTOGENES DETECTION METHOD

(71) Applicants: NIPPN CORPORATION, Tokyo (JP); FASMAC CO., LTD., Atsugi (JP)

(72) Inventors: Mika Tsuna, Atsugi (JP); Yoshitaka Harada, Atsugi (JP); Yasuhiro Seto, Atsugi (JP); Kazuto Takasaki, Atsugi (JP)

(73) Assignees: NIPPN CORPORATION, Tokyo (JP); FASMAC CO., LTD., Atsugi (JP)

( * ) Notice: Subject to any disclaimer, the term of this patent is extended or adjusted under 35 U.S.C. 154(b) by 1145 days.

(21) Appl. No.: 16/632,051

(22) PCT Filed: Dec. 18, 2017

(86) PCT No.: PCT/JP2017/045280
§ 371 (c)(1),
(2) Date: Aug. 20, 2020

(87) PCT Pub. No.: WO2019/016976
PCT Pub. Date: Jan. 24, 2019

(65) Prior Publication Data
US 2021/0024979 A1  Jan. 28, 2021

(30) Foreign Application Priority Data
Jul. 20, 2017 (JP) ................................. 2017-141201

(51) Int. Cl.
| | |
|---|---|
| C12Q 1/689 | (2018.01) |
| C12Q 1/6853 | (2018.01) |
| C12Q 1/686 | (2018.01) |
| C12Q 1/6869 | (2018.01) |
| G01N 33/52 | (2006.01) |

(52) U.S. Cl.
CPC ........... *C12Q 1/689* (2013.01); *C12Q 1/6853* (2013.01); *C12Q 1/686* (2013.01); *C12Q 1/6869* (2013.01); *G01N 33/52* (2013.01); *C12Q 2600/156* (2013.01); *G01N 2458/00* (2013.01); *G01N 2469/00* (2013.01)

(58) Field of Classification Search
CPC ................................ C12Q 1/689; C12Q 1/686
See application file for complete search history.

(56) References Cited

U.S. PATENT DOCUMENTS

2006/0257894 A1  11/2006 Doumith et al.
2021/0024979 A1  1/2021 Tsuna et al.

FOREIGN PATENT DOCUMENTS

| JP | 2007-61061 A | 3/2007 |
| JP | 2010/0263873 A | 11/2010 |
| JP | 2018-57363 A | 4/2018 |
| WO | WO 2019/016976 A1 | 1/2019 |

OTHER PUBLICATIONS

Deng et al., "Probing the pan-genome of *Listeria monocytogenes*: new insights into intraspecific niche expansion and genomic diversification," BMC Genomics (2010), vol. 11, No. 500, pp. 1-21.
English translation of International Preliminary Report on Patentability and Written Opinion mailed Jan. 30, 2020, in PCT/JP2017/045280.
English translation of International Search Report mailed Mar. 13, 2018, in PCT/JP2017/045280.
Notification No. 1128, Article 2 of the Department of Food Safety, "Examination of *Listeria monocytogenes*", Nov. 28, 2014.
Paul et al., "Genome comparison of *Listeria monocytogenes* serotype 4a strain HCC23 with selected lineage I and lineage II *L. monocytogenes* strains and other *Listeria* strains," Genomics Data (2014), vol. 2, pp. 219-225.
Tan et al., "Development of *Listeria*Base and comparative analysis of *Listeria monocytogenes*," BMC Genomics (2015), vol. 16, No. 755, pp. 1-19.
Tao et al., "Mining of novel species-specific primers for PCR detection of *Listeria monocytogenes* based on genomic approach," World J. Microbiol. Biotechnol. (2015), vol. 31, pp. 1955-1966.
Tsuna et al., "Development of simple method for detection of *Listeria monocytogenes*," Abstracts of the 38th Annual Meeting of Japanese Society of Food Microbiology, Aug. 31, 2017.
Tsuna et al., "Development of simple method for detection of *Listeria monocytogenes*," Poster Session, The 38th Annual Meeting of Japanese Society of Food Microbiology, Oct. 5 to 6, 2017.

*Primary Examiner* — Samuel C Woolwine
*Assistant Examiner* — Lisa Horth
(74) *Attorney, Agent, or Firm* — Birch, Stewart, Kolasch & Birch, LLP

(57) ABSTRACT

Novel means that enables detection of the *monocytogenes* bacterium alone distinctly from other bacteria belonging to the genus *Listeria* with sufficiently high accuracy is disclosed. The present inventors intensively analyzed the genome of the *monocytogenes* bacterium to identify two genes (the lmo0084 gene and the lmo2736 gene) as target regions with which the *monocytogenes* bacterium can be specifically detected distinctly from other bacteria belonging to the genus *Listeria* utilizing a nucleic acid amplification method. By a further intensive study of the base sequences of these two genes, primer setting regions for highly accurate, specific detection of the *monocytogenes* bacterium alone were identified, and preferred particular examples of PCR primer sets, LAMP primer sets, and real-time PCR primer-probe sets were established.

9 Claims, 3 Drawing Sheets

Specification includes a Sequence Listing.

Primer set No. 4   Forward Primer: lmo00084 F281A
Reverse Primer: lmo00084 R757B
PCR product size: 476 bp

LISTERIA-MONOCYTOGENES DETECTION METHOD

REFERENCE TO ELECTRONIC SEQUENCE LISTING

The application contains a Sequence Listing which is hereby incorporated by reference in its entirety. Said .txt copy, created on Jan. 1, 2020, is named "2020-01-17-SequenceListing-0760-0513PUS1.txt" and is 49,849 bytes in size. The sequence listing contained in this txt. file is part of the specification and is hereby incorporated by reference herein in its entirety.

TECHNICAL FIELD

The present invention relates to a method of specifically detecting Listeria monocytogenes and primers therefor.

BACKGROUND ART

Listeriosis is an infection caused by Listeria monocytogenes (which may be hereinafter referred to as "monocytogenes bacterium"). Among the about 10 bacterial species known for the genus Listeria, only the monocytogenes bacterium causes listeriosis in human.

In Western countries, this bacterium is regarded as a serious food-poisoning bacterium. Also in Japan, the monocytogenes bacterium is often detected from a variety of foods including meat products and dairy products. Since the monocytogenes bacterium can be killed by ordinary cooking with heat, food poisoning hardly occurs by foods requiring cooking with heat. However, since the monocytogenes bacterium grows even under low-temperature conditions, for example, in a refrigerator, the risk of food poisoning by the monocytogenes bacterium still exists even when appropriate storage is carried out at low temperature for foods eaten without cooking with heat, such as dairy products including cheese; and ham, salami, and smoked salmon.

In the official qualitative test for the monocytogenes bacterium, judgment for the monocytogenes bacterium is carried out based on formation of a colony accompanied by a milky-white halo on a selective isolation medium such as ALOA agar medium or CHROMagar medium (Non-patent Document 1). However, the genus Listeria includes halo-forming species other than the monocytogenes bacterium. Therefore, in cases of contamination with such bacteria belonging to the genus Listeria, they are judged as positive for the monocytogenes bacterium. Further, the official test using a selective isolation medium takes days to carry out the judgment since it requires several days of confirmation culture, and the confirmation culture requires skill, which is problematic.

A variety of primers for detection of the monocytogenes bacterium by real-time PCR or the like have been reported (for example, Patent Documents 1 and 2), and there are also commercially available kits. In these prior art techniques, genes associated with pathogenicity of the monocytogenes bacterium are targeted. However, since the known methods including the commercially available kits have failed to sufficiently suppress production of false negatives and false positives, they are not sufficiently satisfactory as test methods for specifically detecting only the monocytogenes bacterium.

PRIOR ART DOCUMENT(S)

Patent Document(s)

Patent Document 1: JP 2010-263873 A
Patent Document 2: JP 2007-61061 A

Non-Patent Document(s)

Non-Patent Document 1: Notification No. 1128, Article 2 of the Department of Food Safety, "Examination of Listeria monocytogenes", Nov. 28, 2014

SUMMARY OF THE INVENTION

Problems to be Solved by the Invention

An object of the present invention is to provide means that enables detection of the monocytogenes bacterium alone distinctly from other bacteria belonging to the genus Listeria with sufficiently high accuracy.

Means for Solving the Problems

The present inventors intensively analyzed the genome of the monocytogenes bacterium to identify two genes as target regions with which the monocytogenes bacterium can be specifically detected distinctly from other bacteria belonging to the genus Listeria utilizing a nucleic acid amplification method. The present inventors studied the base sequences of these two genes in more detail, and carried out an intensive study by designing a large number of primers and using a variety of combinations of the primers for genomic DNAs of monocytogenes bacterial strains and other bacterial strains belonging to the genus Listeria. As a result, the present inventors succeeded in identification of primer setting regions for specific detection of the monocytogenes bacterium alone with high accuracy, and also in establishment of preferred particular examples of PCR primer sets and LAMP primer sets, thereby completing the present invention.

More specifically, the present invention provides a primer set for detection of Listeria monocytogenes, comprising any of the following primer sets for amplification of a partial region of the lmo0084 gene or the lmo2736 gene of Listeria monocytogenes:

(A-1) a set of a forward primer containing in its 3'-side the base sequence of SEQ ID NO:26 or a sequence which is the same as the base sequence except that not more than 4 bases are substituted at a genetic polymorphism site(s) in the base sequence, and a reverse primer containing in its 3'-side the base sequence of SEQ ID NO:30 or a sequence which is the same as the base sequence except that not more than 4 bases are substituted at a genetic polymorphism site(s) in the base sequence;

(A-2) a set of a forward primer containing in its 3'-side the base sequence of SEQ ID NO:26 or a sequence which is the same as the base sequence except that not more than 4 bases are substituted at a genetic polymorphism site(s) in the base sequence, and a reverse primer containing in its 3'-side the base sequence of SEQ ID NO:31 or a sequence which is the same as the base sequence except that not more than 4 bases are substituted at a genetic polymorphism site(s) in the base sequence;

(A-3) a set of a forward primer containing in its 3'-side the base sequence of SEQ ID NO:27 or a sequence which is the same as the base sequence except that not more than 4 bases are substituted at a genetic polymorphism site(s) in the base sequence, and a reverse primer containing in its 3'-side the base sequence of SEQ ID NO:30 or a sequence which is the same as the base sequence except that not more than 4 bases are substituted at a genetic polymorphism site(s) in the base sequence;

(A-4) a set of a forward primer containing in its 3'-side the base sequence of SEQ ID NO:27 or a sequence which is the same as the base sequence except that not more than 4 bases are substituted at a genetic polymorphism site(s) in the base sequence, and a reverse primer containing in its 3'-side the base sequence of SEQ ID NO:31 or a sequence which is the same as the base sequence except that not more than 4 bases are substituted at a genetic polymorphism site(s) in the base sequence;

(A-5) a set of a forward primer containing in its 3'-side the base sequence of SEQ ID NO:28 or a sequence which is the same as the base sequence except that not more than 4 bases are substituted at a genetic polymorphism site(s) in the base sequence, and a reverse primer containing in its 3'-side the base sequence of SEQ ID NO:30 or a sequence which is the same as the base sequence except that not more than 4 bases are substituted at a genetic polymorphism site(s) in the base sequence;

(A-6) a set of a forward primer containing in its 3'-side the base sequence of SEQ ID NO:28 or a sequence which is the same as the base sequence except that not more than 4 bases are substituted at a genetic polymorphism site(s) in the base sequence, and a reverse primer containing in its 3'-side the base sequence of SEQ ID NO:31 or a sequence which is the same as the base sequence except that not more than 4 bases are substituted at a genetic polymorphism site(s) in the base sequence;

(A-7) a set of a forward primer containing in its 3'-side the base sequence of SEQ ID NO:29 or a sequence which is the same as the base sequence except that not more than 4 bases are substituted at a genetic polymorphism site(s) in the base sequence, and a reverse primer containing in its 3'-side the base sequence of SEQ ID NO:30 or a sequence which is the same as the base sequence except that not more than 4 bases are substituted at a genetic polymorphism site(s) in the base sequence;

(A-8) a set of a forward primer containing in its 3'-side the base sequence of SEQ ID NO:29 or a sequence which is the same as the base sequence except that not more than 4 bases are substituted at a genetic polymorphism site(s) in the base sequence, and a reverse primer containing in its 3'-side the base sequence of SEQ ID NO:31 or a sequence which is the same as the base sequence except that not more than 4 bases are substituted at a genetic polymorphism site(s) in the base sequence;

(B-1) a set of a forward primer containing in its 3'-side the base sequence of SEQ ID NO:58 or a sequence which is the same as the base sequence except that not more than 4 bases are substituted at a genetic polymorphism site(s) in the base sequence, and a reverse primer containing in its 3'-side the base sequence of SEQ ID NO:59 or a sequence which is the same as the base sequence except that not more than 4 bases are substituted at a genetic polymorphism site(s) in the base sequence;

(C-1) a set of a forward primer containing in its 3'-side the base sequence of SEQ ID NO:32 or a sequence which is the same as the base sequence except that not more than 4 bases are substituted at a genetic polymorphism site(s) in the base sequence, and a reverse primer containing in its 3'-side the base sequence of SEQ ID NO:37 or a sequence which is the same as the base sequence except that not more than 4 bases are substituted at a genetic polymorphism site(s) in the base sequence;

(D-1) a set of a forward primer containing in its 3'-side the base sequence of SEQ ID NO:33 or a sequence which is the same as the base sequence except that not more than 4 bases are substituted at a genetic polymorphism site(s) in the base sequence, and a reverse primer containing in its 3'-side the base sequence of SEQ ID NO:38 or a sequence which is the same as the base sequence except that not more than 4 bases are substituted at a genetic polymorphism site(s) in the base sequence;

(E-1) a set of a forward primer containing in its 3'-side the base sequence of SEQ ID NO:34 or a sequence which is the same as the base sequence except that not more than 4 bases are substituted at a genetic polymorphism site(s) in the base sequence, and a reverse primer containing in its 3'-side the base sequence of SEQ ID NO:38 or a sequence which is the same as the base sequence except that not more than 4 bases are substituted at a genetic polymorphism site(s) in the base sequence;

(F-1) a set of a forward primer containing in its 3'-side the base sequence of SEQ ID NO:34 or a sequence which is the same as the base sequence except that not more than 4 bases are substituted at a genetic polymorphism site(s) in the base sequence, and a reverse primer containing in its 3'-side the base sequence of SEQ ID NO:39 or a sequence which is the same as the base sequence except that not more than 4 bases are substituted at a genetic polymorphism site(s) in the base sequence;

(G-1) a set of a forward primer containing in its 3'-side the base sequence of SEQ ID NO:34 or a sequence which is the same as the base sequence except that not more than 4 bases are substituted at a genetic polymorphism site(s) in the base sequence, and a reverse primer containing in its 3'-side the base sequence of SEQ ID NO:40 or a sequence which is the same as the base sequence except that not more than 4 bases are substituted at a genetic polymorphism site(s) in the base sequence;

(H-1) a set of a forward primer containing in its 3'-side the base sequence of SEQ ID NO:35 or a sequence which is the same as the base sequence except that not more than 4 bases are substituted at a genetic polymorphism site(s) in the base sequence, and a reverse primer containing in its 3'-side the base sequence of SEQ ID NO:39 or a sequence which is the same as the base sequence except that not more than 4 bases are substituted at a genetic polymorphism site(s) in the base sequence;

(I-1) a set of a forward primer containing in its 3'-side the base sequence of SEQ ID NO:35 or a sequence which is the same as the base sequence except that not more than 4 bases are substituted at a genetic polymorphism site(s) in the base sequence, and a reverse primer containing in its 3'-side the base sequence of SEQ ID NO:40 or a sequence which is the same as the base sequence except that not more than 4 bases are substituted at a genetic polymorphism site(s) in the base sequence;

(I-2) a set of a forward primer containing in its 3'-side the base sequence of SEQ ID NO:60 or a sequence which is the same as the base sequence except that not more than 4 bases are substituted at a genetic polymorphism site(s) in the base sequence, and a reverse primer containing in its 3'-side the base sequence of SEQ ID NO:61 or a sequence which is the same as the base sequence except that not more than 4 bases are substituted at a genetic polymorphism site(s) in the base sequence;

(I-3) a set of a forward primer containing in its 3'-side the base sequence of SEQ ID NO:62 or a sequence which is the same as the base sequence except that not more than 4 bases are substituted at a genetic polymorphism site(s) in the base sequence, and a reverse primer containing in its 3'-side the base sequence of SEQ ID NO:61 or a sequence which is the same as the base sequence except that not more than 4 bases are substituted at a genetic polymorphism site(s) in the base sequence;

(J-1) a set of a forward primer containing in its 3'-side the base sequence of SEQ ID NO:35 or a sequence which is the same as the base sequence except that not more than 4 bases are substituted at a genetic polymorphism site(s) in the base sequence, and a reverse primer containing in its 3'-side the base sequence of SEQ ID NO:41 or a sequence which is the same as the base sequence except that not more than 4 bases are substituted at a genetic polymorphism site(s) in the base sequence;

(K-1) a set of a forward primer containing in its 3'-side the base sequence of SEQ ID NO:36 or a sequence which is the same as the base sequence except that not more than 4 bases are substituted at a genetic polymorphism site(s) in the base sequence, and a reverse primer containing in its 3'-side the base sequence of SEQ ID NO:39 or a sequence which is the same as the base sequence except that not more than 4 bases are substituted at a genetic polymorphism site(s) in the base sequence;

(L-1) a set of a forward primer containing in its 3'-side the base sequence of SEQ ID NO:36 or a sequence which is the same as the base sequence except that not more than 4 bases are substituted at a genetic polymorphism site(s) in the base sequence, and a reverse primer containing in its 3'-side the base sequence of SEQ ID NO:40 or a sequence which is the same as the base sequence except that not more than 4 bases are substituted at a genetic polymorphism site(s) in the base sequence; and (M-1) a set of a forward primer containing in its 3'-side the base sequence of SEQ ID NO:63 or a sequence which is the same as the base sequence except that not more than 4 bases are substituted at a genetic polymorphism site(s) in the base sequence, and a reverse primer containing in its 3'-side the base sequence of SEQ ID NO:64 or a sequence which is the same as the base sequence except that not more than 4 bases are substituted at a genetic polymorphism site(s) in the base sequence.

The present invention also provides a primer set for detection of *Listeria monocytogenes*, comprising any of the following sets:

(A-9) a set of a mixed forward primer containing in its 3'-side the base sequence of SEQ ID NO:67, and a mixed reverse primer containing in its 3'-side the base sequence of SEQ ID NO:69;

(A-10) a set of a mixed forward primer containing in its 3'-side the base sequence of SEQ ID NO:68, and a mixed reverse primer containing in its 3'-side the base sequence of SEQ ID NO:69;

(D-2) a set of a mixed forward primer containing in its 3'-side the base sequence of SEQ ID NO:70, and a mixed reverse primer containing in its 3'-side the base sequence of SEQ ID NO:74;

(E-2) a set of a mixed forward primer containing in its 3'-side the base sequence of SEQ ID NO:71, and a mixed reverse primer containing in its 3'-side the base sequence of SEQ ID NO:74;

(F-2) a set of a mixed forward primer containing in its 3'-side the base sequence of SEQ ID NO:71, and a mixed reverse primer containing in its 3'-side the base sequence of SEQ ID NO:75;

(G-2) a set of a mixed forward primer containing in its 3'-side the base sequence of SEQ ID NO:71, and a mixed reverse primer containing in its 3'-side the base sequence of SEQ ID NO:76;

(H-2) a set of a mixed forward primer containing in its 3'-side the base sequence of SEQ ID NO:72, and a mixed reverse primer containing in its 3'-side the base sequence of SEQ ID NO:75;

(I-4) a set of a mixed forward primer containing in its 3'-side the base sequence of SEQ ID NO:72, and a mixed reverse primer containing in its 3'-side the base sequence of SEQ ID NO:76;

(J-2) a set of a mixed forward primer containing in its 3'-side the base sequence of SEQ ID NO:72, and a reverse primer containing in its 3'-side the base sequence of SEQ ID NO:41 or a sequence which is the same as the base sequence except that not more than 4 bases are substituted at a genetic polymorphism site(s) in the base sequence;

(K-3) a set of a mixed forward primer containing in its 3'-side the base sequence of SEQ ID NO:73, and a mixed reverse primer containing in its 3'-side the base sequence of SEQ ID NO:75;

(L-2) a set of a mixed forward primer containing in its 3'-side the base sequence of SEQ ID NO:73, and a mixed reverse primer containing in its 3'-side the base sequence of SEQ ID NO:76;

(N-1) a set of a mixed forward primer containing in its 3'-side the base sequence of SEQ ID NO:71, and a reverse primer containing in its 3'-side the base sequence of SEQ ID NO:41 or a sequence which is the same as the base sequence except that not more than 4 bases are substituted at a genetic polymorphism site(s) in the base sequence; and (O-1) a set of a mixed forward primer containing in its 3'-side the base sequence of SEQ ID NO:73, and a reverse primer containing in its 3'-side the base sequence of SEQ ID NO:41 or a sequence which is the same as the base sequence except that not more than 4 bases are substituted at a genetic polymorphism site(s) in the base sequence.

The present invention also provides a loop-mediated isothermal amplification primer set for detection of *Listeria monocytogenes*, comprising any of the following sets:

(i) a set of an F3 primer composed of the base sequence of SEQ ID NO:42, a B3 primer composed of the base sequence of SEQ ID NO:43, an FIP primer composed of the base sequence of SEQ ID NO:4, and a BIP primer composed of the base sequence of SEQ ID NO:45;

(ii) a set of an F3 primer composed of the base sequence of SEQ ID NO:46, a B3 primer composed of the base sequence of SEQ ID NO:47, an FIP primer composed of the base sequence of SEQ ID NO:48, and a BIP primer composed of the base sequence of SEQ ID NO:49;

(iii) a set of an F3 primer composed of the base sequence of SEQ ID NO:50, a B3 primer composed of the base sequence of SEQ ID NO:51, an FIP primer composed of the base sequence of SEQ ID NO:52, and a BIP primer composed of the base sequence of SEQ ID NO:53; and (iv) a set of an F3 primer composed of the base sequence of SEQ ID NO:54, a B3 primer composed of the base sequence of SEQ ID NO:55, an FIP primer composed of the base sequence of SEQ ID NO:56, and a BIP primer composed of the base sequence of SEQ ID NO:57.

The present invention also provides a method of detecting *Listeria monocytogenes*, comprising a step of amplifying a partial region of the lmo0084 gene or the lmo2736 gene by a nucleic acid amplification method using the primer set of the present invention described above.

The present invention also provides a probe for detection of *Listeria monocytogenes*, comprising an oligonucleotide portion having the base sequence of SEQ ID NO:77, SEQ ID NOs:80 to 82, SEQ ID NO:85 (wherein ngaan is tgaaa or cgaac), or SEQ ID NO:86 (wherein ngcaan is ggcaag or cgcaac).

The present invention also provides a primer-probe set for real-time PCR for detection of *Listeria monocytogenes*, comprising any of the following sets of primers and a probe:

[1] a set of a forward primer containing in its 3'-side the base sequence of SEQ ID NO:67, a reverse primer containing in its 3'-side the base sequence of SEQ ID NO:69, and a probe containing an oligonucleotide portion having the base sequence of SEQ ID NO:77 or 80;

[2] a set of a forward primer containing in its 3'-side the base sequence of SEQ ID NO:67, a reverse primer containing in its 3'-side the base sequence of SEQ ID NO:69, and a mixed probe containing an oligonucleotide portion having the base sequence of SEQ ID NO:85 (wherein ngaan is tgaaa or cgaac);

[3] a set of a forward primer containing in its 3'-side the base sequence of SEQ ID NO:68, a reverse primer containing in its 3'-side the base sequence of SEQ ID NO:69, and a probe containing an oligonucleotide portion having the base sequence of SEQ ID NO:77 or 80;

[4] a set of a forward primer containing in its 3'-side the base sequence of SEQ ID NO:68, a reverse primer containing in its 3'-side the base sequence of SEQ ID NO:69, and a mixed probe containing an oligonucleotide portion having the base sequence of SEQ ID NO:85 (wherein ngaan is tgaaa or cgaac);

[5] a set of a forward primer containing in its 3'-side the base sequence of SEQ ID NO:32, a reverse primer containing in its 3'-side the base sequence of SEQ ID NO:37, and a probe containing an oligonucleotide portion having the base sequence of SEQ ID NO:81; and

[6] a set of a forward primer containing in its 3'-side the base sequence of SEQ ID NO:70, a reverse primer containing in its 3'-side the base sequence of SEQ ID NO:74, and a probe containing an oligonucleotide portion having the base sequence of SEQ ID NO:82; and

[7] a set of a forward primer containing in its 3'-side the base sequence of SEQ ID NO:72, a reverse primer containing in its 3'-side the base sequence of SEQ ID NO:76, and a mixed probe containing an oligonucleotide portion having the base sequence of SEQ ID NO:86 (wherein ngcaan is ggcaag or cgcaac).

Effect of the Invention

According to the present invention, primers with which various bacterial strains of the *monocytogenes* bacterium can be specifically detected distinctly from other bacteria belonging to the genus *Listeria* are provided. According to the method of the present invention, occurrence of false negatives and false positives can be remarkably reduced compared to test methods based on conventional nucleic acid amplification methods. Bacteria belonging to the genus *Listeria* also include species other than the *monocytogenes* bacterium that form colonies accompanied by milky-white halos on a selective isolation medium. According to the present invention, no amplification occurs with those bacterial strains, and such bacterial strains can therefore be distinguished from the *monocytogenes* bacterium even based on the result of a nucleic acid amplification method alone. Further, serotypes of the *monocytogenes* bacterium can be identified by designing probes targeting polymorphic sequences characteristic to the individual serotypes, such as the TaqMan (registered trademark) probe 0084TMP535-558 (CC) in the following Examples, and carrying out real-time PCR.

BRIEF DESCRIPTION OF THE DRAWINGS

FIG. 1-2 shows images of colonies obtained by culturing species belonging to the genus *Listeria* other than the *monocytogenes* bacterium on ALOA agar medium or CHROMagar medium (examples of images of a false-positive colony forming a halo).

FIG. 1-3 shows images of colonies obtained by culturing species belonging to the genus *Listeria* other than the *monocytogenes* bacterium on ALOA agar medium or CHROMagar medium (examples of images of a negative colony forming no halo).

FIG. 2-1 shows an example of the result of PCR using PCR primers for detection of *Listeria monocytogenes* designed in Examples. The PCR was carried out using Prime set No. 4, which targets the lmo00084 gene. Detection was carried out by 2% agarose gel electrophoresis. The 476-bp PCR products indicated by arrows are specific amplification products from the *monocytogenes* bacterium. The number assigned to each lane corresponds to a bacterial strain No. listed in Table 5-1 or Table 5-2. The numbers 1 to 10 correspond to *monocytogenes* (corresponding, from No. 1, to the serotypes 1/2a, 1/2b, 1/2c, 3a, 3b, 3c, 4a, 4b, 4d, and 5 in this order), and the numbers 11 to 22 correspond to species belonging to the genus *Listeria* other than *monocytogenes*.

FIG. 2-2 shows an example of the result of PCR using PCR primers for detection of *Listeria monocytogenes* designed in Examples. The PCR was carried out using Prime set No. 1, which targets the lmo02736 gene. Detection was carried out by 2% agarose gel electrophoresis. The 168-bp PCR products indicated by arrows are specific amplification products from the *monocytogenes* bacterium. The arrows indicate the specific amplification products. The number assigned to each lane is the same as in FIG. 2-1.

MODE FOR CARRYING OUT THE INVENTION

Figure 1:
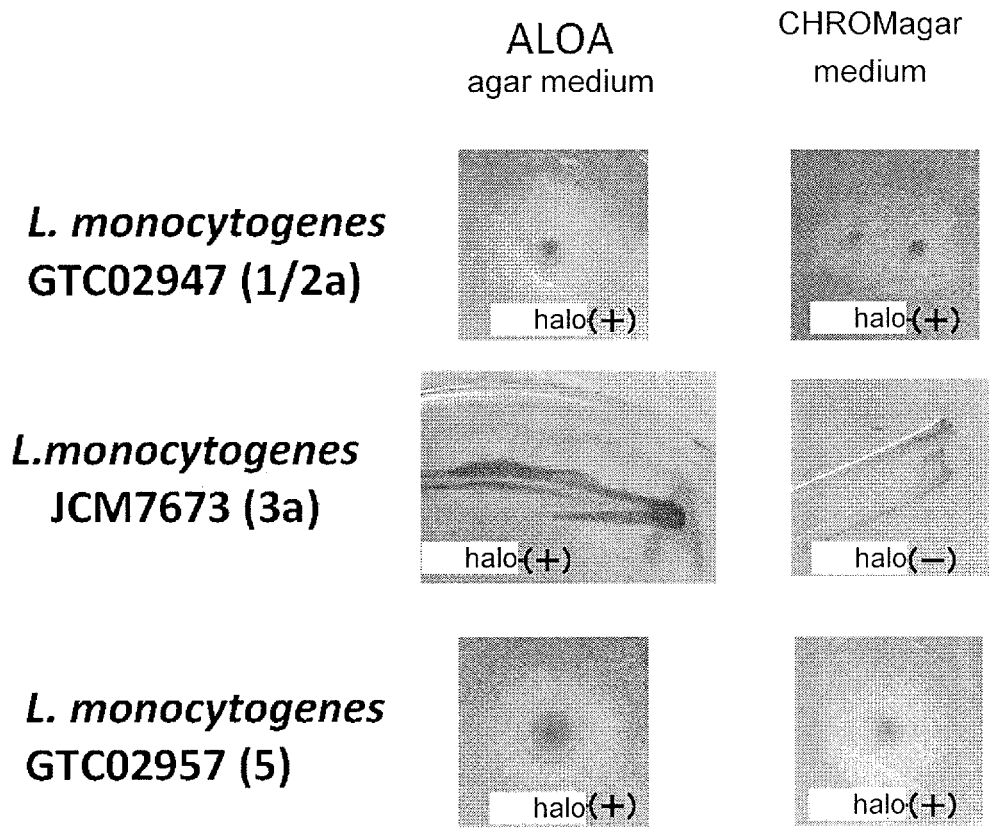
FIG. 1-1 shows images of colonies obtained by culturing the *monocytogenes* bacterium on ALOA agar medium or CHROMagar medium (examples of images of a positive colony forming a halo or a false-negative colony forming no halo).

One of the following two genes present in the genome of the *monocytogenes* bacterium is the target to be detected in the present invention.

TABLE 1

| Gene name (*) | Gene length | Gene type | Description |
| --- | --- | --- | --- |
| lmo0084 | 984 | CDS | similar to oxidoreductases |
| lmo2736 | 1134 | CDS | conserved hypothetical protein |

(*) In the genomic sequence information of GenBank Accession No. AL591824.1, the lmo0084 gene corresponds to the region of 86747-87744, and lmo2736 corresponds to the region of 2811788-2812921.

SEQ ID NOs:1 to 12 in SEQUENCE LISTING show base sequences of the lmo0084 gene in the serotypes 1/2a, 1/2b, 1/2c, 3a, 3b, 3c, 4a, 4b, 4c, 4d, 4e, and 7, respectively, of the *monocytogenes* bacterium. SEQ ID NOs:13 to 25 show base sequences of the lmo2736 gene of the above individual serotypes of the *monocytogenes* bacterium (regarding 4b, two kinds of base sequences are shown as SEQ ID NOs:20 and 21). In the present description, specification of partial regions of each gene is carried out using, as a standard, the base sequence in the serotype 1/2a shown in SEQ ID NO:1 for the lmo0084 gene, or the base sequence in the serotype 1/2a shown in SEQ ID NO:13 for the lmo2736 gene. For example, "the region of position 306 to position 737 in the lmo0084 gene shown in SEQ ID NO:1" includes the region of position 306 to position 737 in the lmo0084 gene of various serotypes. The same applies to the lmo2736 gene. The accession numbers of the sequences of SEQ ID NOs:1 to 25 are as shown below in Table 2.

TABLE 2

| SEQ ID NO. | Gene name | Serotype | Accession No. |
| --- | --- | --- | --- |
| 1 | lmo0084 | 1/2a | NC_018592.1 |
| 2 | lmo0084 | 1/2b | NC_018587.1 |
| 3 | lmo0084 | 1/2c | NC_018588.1 |
| 4 | lmo0084 | 3a | NC_018593.1 |
| 5 | lmo0084 | 3b | NC_018586.1 |
| 6 | lmo0084 | 3c | NC_018589.1 |
| 7 | lmo0084 | 4a | NC_017529.1 |
| 8 | lmo0084 | 4b | NC_019556.1 |
| 9 | lmo0084 | 4c | NC_018590.1 |
| 10 | lmo0084 | 4d | NC_018584.1 |
| 11 | lmo0084 | 4e | NC_018585.1 |
| 12 | lmo0084 | 7 | NC_018591.1 |
| 13 | lmo2736 | 1/2a | NC_018592.1 |
| 14 | lmo2736 | 1/2b | NC_018587.1 |
| 15 | lmo2736 | 1/2c | NC_018588.1 |
| 16 | lmo2736 | 3a | NC_018593.1 |
| 17 | lmo2736 | 3b | NC_018586.1 |
| 18 | lmo2736 | 3c | NC_018589.1 |
| 19 | lmo2736 | 4a | NC_017529.1 |

TABLE 2-continued

| SEQ ID NO. | Gene name | Serotype | Accession No. |
| --- | --- | --- | --- |
| 20 | lmo2736 | 4b | NC_019556.1 |
| 21 | lmo2736 | 4b | NC_018642.1 |
| 22 | lmo2736 | 4c | NC_018590.1 |
| 23 | lmo2736 | 4d | NC_018584.1 |
| 24 | lmo2736 | 4e | NC_018585.1 |
| 25 | lmo2736 | 7 | NC_018591.1 |

The specific detection of the *monocytogenes* bacterium can be carried out by a nucleic acid amplification method using a primer(s) for detection of *Listeria monocytogenes*, which primer(s) specifically hybridize(s) to a region in the lmo0084 gene or the lmo2736 gene. As the nucleic acid amplification method, various known methods such as the PCR method or the isothermal amplification method may be used. In the present invention, the term "primer" includes PCR primers and isothermal amplification primers. In the present invention, the PCR method means a nucleic acid amplification method in which the temperature is repeatedly changed to amplify a region of interest.

The term "specifically hybridizes" means that, under normal hybridization conditions, the primer hybridizes only to a target region, and does not substantially hybridize to other regions. The term "under normal hybridization conditions" means that a reaction is carried out under conditions used for annealing in normal PCR, for example, at an appropriate annealing temperature of about 54° C. to 60° C. using a common buffer such as 50 mM KCl, 10 mM Tris-HCl (pH 8.3 to 9.0), 1.5 mM $MgCl_2$ in cases of PCR using Taq polymerase. However, the appropriate annealing temperature is not limited to the above example, and may be determined based on the Tm value of the primer and an empirical rule by the experimenter. Those skilled in the art can easily determine the temperature. The term "does not substantially hybridize" means that the primer does not hybridize at all, or, even in cases where it hybridizes, a much smaller amount of the primer hybridizes compared to the case where the primer hybridizes to the target region, so that only a relatively ignorable, small amount of the primer hybridizes.

For detection of the amplification product obtained by the nucleic acid amplification method, any known detection method may be applied. In cases of the PCR method, the detection may be carried out by electrophoresis, the intercalation method, the quencher-mediated fluorescence detection method, or the like, and, in cases of the isothermal amplification method, the detection may be carried out by a method in which pyrophosphoric acid as an amplification by-product is insolubilized, the intercalation method, the quencher-mediated fluorescence detection method, or the like. Alternatively, the amplification product may be detected by nucleic acid chromatography.

The term "PCR method" also includes the real-time PCR method. In real-time PCR, detection and monitoring of the amplification product are commonly carried out by the intercalation method or the quencher-mediated fluorescence detection method. In the following Examples, a specific example of the real-time PCR detection system using the TaqMan (registered trademark) probe method as one example of the quencher-mediated fluorescence detection method is described. However, the detection method is not limited thereto, and a variety of methods may be employed.

In cases of nucleic acid chromatography, the detection is possible by carrying out nucleic acid amplification using a primer set for detection of the *monocytogenes* bacterium of the invention, and then developing the resulting amplification product on a strip on which a capture substance that specifically binds to the amplification product is immobilized in the shape of a line or the like. For capturing the amplification product, for example, a labeling compound such as biotin or DIG, or an arbitrary base sequence may be added to the 5-side of the forward or reverse primer, and a labeling-compound-specific binding substance such as avidin or an anti-DIG antibody, or an oligonucleotide probe having a base sequence complementary to the arbitrary base sequence may be immobilized as the capture substance on the strip. For further increasing the specificity of the detection, as the capture probe on the strip, a probe having a base sequence that specifically hybridizes to a certain partial sequence in the region amplified by the primers may be used. In order to provide such a capture probe, a partial region in the region amplified by the primers may be appropriately selected, and a probe capable of hybridizing to the amplification product of each serotype may be designed with reference to the base sequence of the lmo0084 gene of each serotype of SEQ ID NOs:1 to 12 or the base sequence of the lmo2736 gene of each serotype of SEQ ID NOs:13 to 25. The detection system may be constructed in the same manner as in a known nucleic acid chromatography method, and examples of the detection system include coloring detection methods using an enzyme such as peroxidase or using particles such as colloidal gold or colored latex.

The isothermal amplification method is not limited, and various isothermal amplification methods such as the Loop-Mediated Isothermal Amplification (LAMP) method, the Strand Displacement Amplification (SDA) method, the Isothermal and Chimeric primer-initiated Amplification of Nucleic acids (ICAN) method, the Helicase-Dependent Amplification (HDA) method, and the Nicking Enzyme Amplification Reaction (NEAR) method may be employed. Examples of the isothermal amplification primers include the LAMP primers designed in the following Examples.

In the present invention, typical samples to be tested are samples collected from foods (including raw materials and processed foods). However, the samples to be tested are not limited thereto, and include a variety of samples whose test for the *monocytogenes* bacterium is desired, such as swabs from production lines and fingers of workers in food factories.

As a primer set to be used for the nucleic acid amplification method such as the PCR method or the isothermal amplification method for specifically detecting the *monocytogenes* bacterium distinctly from other bacteria belonging to the genus *Listeria* and from other food-poisoning microbes, a primer set which specifically hybridizes to a region in the lmo0084 gene sequence of SEQ ID NO:1 or the lmo2736 gene sequence of SEQ ID NO:13 may be used. The primer set may be designed taking into account the primer length, the GC content, the Tm value, bias of bases, contiguous sequences, complementarity inside and between primers, the molecular weight of the amplification product, genetic polymorphisms in the target region, and the like. In cases where the primer set is used in the PCR method, it may be designed to have a length of about 15 to 30 bases, a GC content of about 40 to 60%, and a Tm value of about 50 to 70° C. For a nucleic acid amplification method other than the PCR method, the primer set may be designed according to the principle of the method, for example, as in the LAMP method described below.

Each primer constituting such a primer set is generally preferably designed for a region having less sequence diversity among serotypes, but may also be designed in a region having a small number of genetic polymorphisms. In cases where the primer is designed for a region containing a genetic polymorphism(s), the primer may be designed such that a base substitution(s) reflecting the genetic polymorphism(s) is/are added to the gene sequence in the serotype 1/2a of SEQ ID NO:1 or SEQ ID NO:13. The number of the base substitution(s) reflecting the genetic polymorphism(s) is preferably not more than 20%, more preferably not more than 15% per primer. More specifically, in cases of a primer having a chain length of 20 bases containing no additional sequence, the primer may be designed to have a sequence in which not more than 4, preferably not more than 3 bases are substituted at a genetic polymorphism site(s) in the 20-base region. In some cases, the thus designed primer may have a sequence identical to the sequence of a partial region of the gene sequence of another serotype, or the complementary strand thereof. In cases where primers containing substitutions at a genetic polymorphism site(s) are used, primers for the individual genetic polymorphisms may be used; a primer mixture prepared by mixing the primers for the individual genetic polymorphisms may be used; or a mixed primer synthesized such that the genetic polymorphism site(s) has/have mixed bases according to the genetic polymorphisms (for example, when some serotypes have G while other serotypes have C as the base at a certain site, a mixed primer prepared such that the base at the site is S (G or C)); may be used.

In the present invention, a primer for specifically detecting the *monocytogenes* bacterium may be designed such that the primer specifically hybridizes to any of the following regions (1) to (14) taking the above factors into account.

(1) The region of position 261 to position 325 of the lmo0084 gene sequence of SEQ ID NO:1, or the region complementary to this region.

LMO0084-F286A (SEQ ID NO:26), LMO0084-F286B (SEQ ID NO:27), LMO0084-F281A (SEQ ID NO:28), and LMO0084-F281B (SEQ ID NO:29) in Examples are specific examples of a forward primer that hybridizes to the region complementary to the region of position 261 to position 325. LMO0084-F286/M (SEQ ID NO:67) and LMO0084-F281/M (SEQ ID NO:68) are specific examples of a mixed forward primer that hybridizes to the region complementary to this region. Primers containing the base sequence of SEQ ID NO:59 in the 3'-side thereof, such as the LAMP primer LMO84 BIP (SEQ ID NO:45) in Examples, are specific examples of a reverse primer that hybridizes to the region of position 261 to position 325.

(2) The region of position 718 to position 777 of the lmo0084 gene sequence of SEQ ID NO:1, or the region complementary to this region.

LMO0084-R757A (SEQ ID NO:30) and LMO0084-R757B (SEQ ID NO:31) in Examples are specific examples of a reverse primer that hybridizes to the region of position 718 to position 777. LMO0084-R757/M (SEQ ID NO:69) is a specific example of a mixed reverse primer that hybridizes to this region.

(3) The region of position 108 to position 166 of the lmo0084 gene sequence of SEQ ID NO:1, or the region complementary to this region.

Primers containing the base sequence of SEQ ID NO:58 in the 3'-side thereof, such as the LAMP primer LMO84 FIP (SEQ ID NO:44) in Examples, are specific examples of a forward primer that hybridizes to the region complementary to the region of position 108 to position 166.

(4) The region of position 1 to position 47 of the lmo2736 gene sequence of SEQ ID NO:13, or the region complementary to this region.

LMO2736-F8 (SEQ ID NO:32) in Examples is a specific example of a forward primer that hybridizes to the region complementary to the region of position 1 to position 47.

(5) The region of position 202 to position 261 of the lmo2736 gene sequence of SEQ ID NO:13, or the region complementary to this region.

LMO2736-F222 (SEQ ID NO:33) in Examples is a specific example of a forward primer that hybridizes to the region complementary to the region of position 202 to position 261. LMO2736-F222/M (SEQ ID NO:70) is a specific example of a mixed forward primer that hybridizes to the region complementary to this region.

(6) The region of position 468 to position 527 of the lmo2736 gene sequence of SEQ ID NO:13, or the region complementary to this region.

LMO2736-F488 (SEQ ID NO:34) in Examples is a specific example of a forward primer that hybridizes to the region complementary to the region of position 468 to position 527. LMO2736-F488/M (SEQ ID NO:71) is a specific example of a mixed forward primer that hybridizes to the region complementary to this region.

(7) The region of position 510 to position 569 of the lmo2736 gene sequence of SEQ ID NO:13, or the region complementary to this region.

LMO2736-F530 (SEQ ID NO:35) in Examples, and primers containing the base sequence of SEQ ID NO:60 or 62 in the 3'-side thereof, such as LMO2736-1 FIP (SEQ ID NO:48) and LMO2736-2 FIP (SEQ ID NO:52) in Examples, are specific examples of a forward primer that hybridizes to the region complementary to the region of position 510 to position 569. LMO2736-F530/M (SEQ ID NO:72) is a specific example of a mixed forward primer that hybridizes to the region complementary to this region.

(8) The region of position 552 to position 611 of the lmo2736 gene sequence of SEQ ID NO:13, or the region complementary to this region.

LMO2736-F572 (SEQ ID NO:36) is a specific example of a forward primer that hybridizes to the region complementary to the region of position 552 to position 611; LMO2736-F572/M (SEQ ID NO:73) is a specific example of a mixed forward primer that hybridizes to the region complementary to this region; and LMO2736-R591 (SEQ ID NO:38) is a specific example of a reverse primer that hybridizes to the region of position 552 to position 611.

(9) The region of position 137 to position 196 of the lmo2736 gene sequence of SEQ ID NO:13, or the region complementary to this region.

LMO2736-R176 (SEQ ID NO:37) in Examples is a specific example of a reverse primer that hybridizes to the region of position 137 to position 196.

(10) The region of position 646 to position 705 of the lmo2736 gene sequence of SEQ ID NO:13, or the region complementary to this region.

LMO2736-R685 (SEQ ID NO:39) in Examples is a specific example of a reverse primer that hybridizes to the region of position 646 to position 705. LMO2736-R685/M (SEQ ID NO:75) is a specific example of a mixed reverse primer that hybridizes to this region.

(11) The region of position 732 to position 791 of the lmo2736 gene sequence of SEQ ID NO:13, or the region complementary to this region.

LMO2736-R771 (SEQ ID NO:40) in Examples, and primers containing the base sequence of SEQ ID NO:61 in the 3'-side thereof, such as LMO2736-1 BIP (SEQ ID NO:49) and LMO2736-2 BIP (SEQ ID NO:53) in Examples, are specific examples of a reverse primer that hybridizes to the region of position 732 to position 791. LMO2736-R771/M (SEQ ID NO:76) is a specific example of a mixed reverse primer that hybridizes to this region.

(12) The region of position 953 to position 1012 of the lmo2736 gene sequence of SEQ ID NO:13, or the region complementary to this region.

LMO2736-R992 (SEQ ID NO:41) in Examples is a specific example of a reverse primer that hybridizes to the region of position 953 to position 1012.

(13) The region of position 496 to position 560 of the lmo2736 gene sequence of SEQ ID NO:13, or the region complementary to this region.

Primers containing the base sequence of SEQ ID NO:63 in the 3'-side thereof, such as the LAMP primer LMO2736-10 FIP (SEQ ID NO:56) in Examples, are specific examples of a forward primer that hybridizes to the region complementary to the region of position 496 to position 560.

(14) The region of position 721 to position 775 of the lmo2736 gene sequence of SEQ ID NO:13, or the region complementary to this region.

Primers containing the base sequence of SEQ ID NO:64 in the 3'-side thereof, such as the LAMP primer LMO2736-10 BIP (SEQ ID NO:57) in Examples, are specific examples of a reverse primer that hybridizes to the region of position 721 to position 775.

The primers that specifically hybridize to the regions (1) to (3) of the lmo0084 gene may be, for example, primers each containing in its 3'-side a sequence having not less than 15 consecutive bases, preferably not less than 18 consecutive bases in the region of position 261 to position 325, the region of position 718 to position 777, or the region of position 108 to position 166 in the base sequence of SEQ ID NO:1, or in the region complementary to any of these; or a sequence which is the same as this sequence except that not more than 20% of bases are substituted at a genetic polymorphism site(s) therein.

The primers that specifically hybridize to the regions (4) to (14) of the lmo2736 gene may be, for example, primers each containing in its 3'-side a sequence having not less than 15 consecutive bases, preferably not less than 18 consecutive bases in the region of position 1 to position 47, the region of position 202 to position 261, the region of position 468 to position 527, the region of position 510 to position 569, the region of position 552 to position 611, the region of position 137 to position 196, the region of position 646 to position 705, the region of position 732 to position 791, the region of position 953 to position 1012, the region of position 496 to position 560, or the region of position 721 to position 775 in the base sequence of SEQ ID NO:13, or in the region complementary to any of these; or a sequence which is the same as this sequence except that not more than 20% of bases are substituted at a genetic polymorphism site(s) therein.

Specific examples of a preferred sequence that can be employed for a primer for amplifying/detecting a partial region of the lmo0084 gene include SEQ ID NOs:26 to 31, 58, and 59. SEQ ID NOs:58 and 59 are 3'-side partial sequences of SEQ ID NOs:44 and 45, which are LAMP primer sequences (sequences of the F2 or B2 portion, which hybridize to target sites in the lmo0084 gene). SEQ ID NOs:26 to 29 and 58 are sequences of the sense strand of the lmo0084 gene, and can be used as the sequences of forward primers that hybridize to the antisense strand of the gene. SEQ ID NOs:30, 31, and 59 are sequences of the antisense strand of the lmo0084 gene, and can be used as sequences of reverse primers that hybridize to the sense strand of the gene.

Specific examples of a preferred sequence that can be employed for a primer for amplifying/detecting a partial region of the lmo2736 gene include SEQ ID NOs:32 to 41, and 60 to 64. SEQ ID NOs:60 to 64 are 3'-side partial sequences of SEQ ID NOs:48, 49, 52, 53, 56, and 57, which are LAMP primer sequences (sequences of the F2 or B2 portion, which hybridize to target sites in the lmo2736 gene). SEQ ID NOs:32 to 36, 60, 62, and 63 are sequences of the sense strand of the lmo2736 gene, and can be used as the sequences of forward primers that hybridize to the antisense strand of the gene. SEQ ID NOs:37 to 41, 61, and 64 are sequences of the antisense strand of the lmo2736 gene, and can be used as sequences of reverse primers that hybridize to the sense strand of the gene.

SEQ ID NOs:26 to 31 and SEQ ID NOs:32 to 41, which were mentioned as preferred specific examples of sequences that can be employed for primers for amplifying/detecting a partial region of the lmo0084 gene or the lmo2736 gene, can be used as LAMP primers by providing an additional sequence to the 5'-side thereof as described below.

Examples of the set of a forward primer and a reverse primer for amplification of a partial region of the lmo0084 gene or the lmo2736 gene of the *monocytogenes* bacterium, designed for the regions (1) to (14), include primer sets containing any of the following. The primer set may be PCR primers, or isothermal amplification primers such as LAMP primers.

(A) A set of a forward primer that hybridizes to the region (1) and a reverse primer that hybridizes to the region (2).
(B) A set of a forward primer that hybridizes to the region (3) and a reverse primer that hybridizes to the region (1).
(C) A set of a forward primer that hybridizes to the region (4) and a reverse primer that hybridizes to the region (9).
(D) A set of a forward primer that hybridizes to the region (5) and a reverse primer that hybridizes to the region (8).
(E) A set of a forward primer that hybridizes to the region (6) and a reverse primer that hybridizes to the region (8).
(F) A set of a forward primer that hybridizes to the region (6) and a reverse primer that hybridizes to the region (10).
(G) A set of a forward primer that hybridizes to the region (6) and a reverse primer that hybridizes to the region (11).
(H) A set of a forward primer that hybridizes to the region (7) and a reverse primer that hybridizes to the region (10).
(I) A set of a forward primer that hybridizes to the region (7) and a reverse primer that hybridizes to the region (11).
(J) A set of a forward primer that hybridizes to the region (7) and a reverse primer that hybridizes to the region (12).
(K) A set of a forward primer that hybridizes to the region (8) and a reverse primer that hybridizes to the region (10).
(L) A set of a forward primer that hybridizes to the region (8) and a reverse primer that hybridizes to the region (11).
(M) A set of a forward primer that hybridizes to the region (13) and a reverse primer that hybridizes to the region (14).
(N) A set of a forward primer that hybridizes to the region (6) and a reverse primer that hybridizes to the region (12).
(O) A set of a forward primer that hybridizes to the region (8) and a reverse primer that hybridizes to the region (12).

Specific examples of the sets (A) to (O) described above include the following sets. The alphabets correspond to the (A) to (O), respectively. For example, the following (A-1) to (A-10) are examples of the set (A).

(A-1) A set of a forward primer containing in its 3'-side a sequence having not less than 15 consecutive bases, preferably not less than 18 consecutive bases in the base sequence of SEQ ID NO:26, more preferably the full-length sequence of the base sequence, or a sequence which is the same as the base sequence of SEQ ID NO:26 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:30, more preferably the full-length sequence of the base sequence, or a sequence which is the same as the base sequence of SEQ ID NO:30 except that not more than 4 bases are substituted at a genetic polymorphism site(s) therein. Specific examples of this set include the set of LMO0084-F286A and LMO0084-R757A in the Examples described below.

(A-2) A set of a forward primer containing in its 3'-side a sequence having not less than 15 consecutive bases, preferably not less than 18 consecutive bases in the base sequence of SEQ ID NO:26, more preferably the full-length sequence of the base sequence, or a sequence which is the same as the base sequence of SEQ ID NO:26 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:31, more preferably the full-length sequence of the base sequence, or a sequence which is the same as the base sequence of SEQ ID NO:31 except that not more than 4 bases are substituted at a genetic polymorphism site(s) therein. Specific examples of this set include the set of LMO0084-F286A and LMO0084-R757B in the Examples described below.

(A-3) A set of a forward primer containing in its 3'-side a sequence having not less than 15 consecutive bases, preferably not less than 18 consecutive bases in the base sequence of SEQ ID NO:27, more preferably the full-length sequence of the base sequence, or a sequence which is the same as the base sequence of SEQ ID NO:27 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:30, more preferably the full-length sequence of the base sequence, or a sequence which is the same as the base sequence of SEQ ID NO:30 except that not more than 4 bases are substituted at a genetic polymorphism site(s) therein. Specific examples of this set include the set of LMO0084-F286B and LMO0084-R757A in the Examples described below.

(A-4) A set of a forward primer containing in its 3'-side a sequence having not less than 15 consecutive bases, preferably not less than 18 consecutive bases in the base sequence of SEQ ID NO:27, more preferably the full-length sequence of the base sequence, or a sequence which is the same as the base sequence of SEQ ID NO:27 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:31, more preferably the full-length sequence of the base sequence, or a sequence which is the same as the base sequence of SEQ ID NO:31 except that not more than 4 bases are substituted at a genetic polymorphism site(s) therein. Specific examples of this set include the set of LMO0084-F286B and LMO0084-R757B in the Examples described below.

(A-5) A set of a forward primer containing in its 3'-side a sequence having not less than 15 consecutive bases, preferably not less than 18 consecutive bases in the base sequence of SEQ ID NO:28, more preferably the full-length sequence of the base sequence, or a sequence which is the same as the base sequence of SEQ ID NO:28 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:30, more preferably the full-length sequence of the base sequence, or a sequence which is the same as the base sequence of SEQ ID NO:30 except that not more than 4 bases are substituted at a genetic polymorphism site(s) therein. Specific examples of this set include the set of LMO0084-F281A and LMO0084-R757A in the Examples described below.

(A-6) A set of a forward primer containing in its 3'-side a sequence having not less than 15 consecutive bases, preferably not less than 18 consecutive bases in the base sequence of SEQ ID NO:28, more preferably the full-length sequence of the base sequence, or a sequence which is the same as the base sequence of SEQ ID NO:28 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:31, more preferably the full-length sequence of the base sequence, or a sequence which is the same as the base sequence of SEQ ID NO:31 except that not more than 4 bases are substituted at a genetic polymorphism site(s) therein. Specific examples of this set include the set of LMO0084-F281A and LMO0084-R757B in the Examples described below.

(A-7) A set of a forward primer containing in its 3'-side a sequence having not less than 15 consecutive bases, preferably not less than 18 consecutive bases in the base sequence of SEQ ID NO:29, more preferably the full-length sequence of the base sequence, or a sequence which is the same as the base sequence of SEQ ID NO:29 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:30, more preferably the full-length sequence of the base sequence, or a sequence which is the same as the base sequence of SEQ ID NO:30 except that not more than 4 bases are substituted at a genetic polymorphism site(s) therein. Specific examples of this set include the set of LMO0084-F281B and LMO0084-R757A in the Examples described below.

(A-8) A set of a forward primer containing in its 3'-side a sequence having not less than 15 consecutive bases, preferably not less than 18 consecutive bases in the base sequence of SEQ ID NO:29, more preferably the full-length sequence of the base sequence, or a sequence which is the same as the base sequence of SEQ ID NO:29 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:31, more preferably the full-length sequence of the base sequence, or a sequence which is the same as the base sequence of SEQ ID NO:31 except that not more than 4 bases are substituted at a genetic polymorphism site(s) therein. Specific examples of this set include the set of LMO0084-F281B and LMO0084-R757B in the Examples described below.

(A-9) A set of a mixed forward primer containing in its 3'-side a sequence having not less than 15 consecutive bases, preferably not less than 18 consecutive bases in the base sequence of SEQ ID NO:67, more preferably the full-length sequence of the base sequence, and a mixed reverse primer containing in its 3'-side a sequence having not less than 15 consecutive bases, preferably not less than 18 consecutive bases in the base sequence of SEQ ID NO:69, more preferably the full-length sequence of the base sequence. Specific examples of this set include the set of LMO0084-F286/M and LMO0084-R757/M in the Examples described below.

(A-10) A set of a mixed forward primer containing in its 3'-side a sequence having not less than 15 consecutive bases, preferably not less than 18 consecutive bases in the base sequence of SEQ ID NO:68, more preferably the full-length sequence of the base sequence, and a mixed reverse primer containing in its 3'-side a sequence having not less than 15 consecutive bases, preferably not less than 18 consecutive bases in the base sequence of SEQ ID NO:69, more preferably the full-length sequence of the base sequence. Specific examples of this set include the set of LMO0084-F281/M and LMO0084-R757/M in the Examples described below.

(B-1) A set of a forward primer containing in its 3'-side a sequence having not less than 15 consecutive bases, preferably not less than 18 consecutive bases in the base sequence of SEQ ID NO:58, more preferably the full-length sequence of the base sequence, or a sequence which is the same as the base sequence of SEQ ID NO:58 except that not more than 4 bases are substituted at a genetic polymorphism site(s) therein, and a reverse primer containing in its 3'-side a sequence having not less than 15 consecutive bases in the base sequence of SEQ ID NO:59, preferably the full-length sequence of the base sequence, or a sequence which is the same as the base sequence of SEQ ID NO:59 except that not more than 4 bases are substituted at a genetic polymorphism site(s) therein. Specific examples of this set include the set of the LAMP primers LMO84 FIP and LMO84 BIP in the Examples described below.

(C-1) A set of a forward primer containing in its 3'-side a sequence having not less than 15 consecutive bases, preferably not less than 18 consecutive bases in the base sequence of SEQ ID NO:32, more preferably the full-length sequence of the base sequence, or a sequence which is the same as the base sequence of SEQ ID NO:32 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:37, more preferably the full-length sequence of the base sequence, or a sequence which is the same as the base sequence of SEQ ID NO:37 except that not more than 4 bases are substituted at a genetic polymorphism site(s) therein. Specific examples of this set include the set of LMO2736-F8 and LMO2736-R176 in the Examples described below.

(D-1) A set of a forward primer containing in its 3'-side a sequence having not less than 15 consecutive bases, preferably not less than 18 consecutive bases in the base sequence of SEQ ID NO:33, more preferably the full-length sequence of the base sequence, or a sequence which is the same as the base sequence of SEQ ID NO:33 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:38, more preferably the full-length sequence of the base sequence, or a sequence which is the same as the base sequence of SEQ ID NO:38 except that not more than 4 bases are substituted at a genetic polymorphism site(s) therein. Specific examples of this set include the set of LMO2736-F222 and LMO2736-R591 in the Examples described below.

(D-2) A set of a mixed forward primer containing in its 3'-side a sequence having not less than 15 consecutive bases, preferably not less than 18 consecutive bases in the base sequence of SEQ ID NO:70, more preferably the full-length sequence of the base sequence, and a mixed reverse primer containing in its 3'-side a sequence having not less than 15 consecutive bases, preferably not less than 18 consecutive bases in the base sequence of SEQ ID NO:74, more preferably the full-length sequence of the base sequence. Specific examples of this set include the set of LMO2736-F222/M and LMO2736-R591/M in the Examples described below.

(E-1) A set of a forward primer containing in its 3'-side a sequence having not less than 15 consecutive bases, preferably not less than 18 consecutive bases in the base sequence of SEQ ID NO:34, more preferably the full-length sequence of the base sequence, or a sequence which is the same as the base sequence of SEQ ID NO:34 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:38, more preferably the full-length sequence of the base sequence, or a sequence which is the same as the base sequence of SEQ ID NO:38 except that not more than 4 bases are substituted at a genetic polymorphism site(s) therein. Specific examples of this set include the set of LMO2736-F488 and LMO2736-R591 in the Examples described below.

(E-2) A set of a mixed forward primer containing in its 3'-side a sequence having not less than 15 consecutive bases, preferably not less than 18 consecutive bases in the base sequence of SEQ ID NO:71, more preferably the full-length sequence of the base sequence, and a mixed reverse primer containing in its 3'-side a sequence having not less than 15 consecutive bases, preferably not less than 18 consecutive bases in the base sequence of SEQ ID NO:74, more preferably the full-length sequence of the base sequence. Specific examples of this set include the set of LMO2736-F488/M and LMO2736-R591/M in the Examples described below.

(F-1) A set of a forward primer containing in its 3'-side a sequence having not less than 15 consecutive bases, preferably not less than 18 consecutive bases in the base sequence of SEQ ID NO:34, more preferably the full-length sequence of the base sequence, or a sequence which is the same as the base sequence of SEQ ID NO:34 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:39, more preferably the full-length sequence of the base sequence, or a sequence which is the same as the base sequence of SEQ ID NO:39 except that not more than 4 bases are substituted at a genetic polymorphism site(s) therein. Specific examples of this set include the set of LMO2736-F488 and LMO2736-R685 in the Examples described below.

(F-2) A set of a mixed forward primer containing in its 3'-side a sequence having not less than 15 consecutive bases, preferably not less than 18 consecutive bases in the base sequence of SEQ ID NO:71, more preferably the full-length sequence of the base sequence, and a mixed reverse primer containing in its 3'-side a sequence having not less than 15 consecutive bases, preferably not less than 18 consecutive bases in the base sequence of SEQ ID NO:75, more preferably the full-length sequence of the base sequence. Specific examples of this set include the set of LMO2736-F488/M and LMO2736-R685/M in the Examples described below.

(G-1) A set of a forward primer containing in its 3'-side a sequence having not less than 15 consecutive bases, preferably not less than 18 consecutive bases in the base sequence of SEQ ID NO:34, more preferably the full-length sequence of the base sequence, or a sequence which is the same as the base sequence of SEQ ID NO:34 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:40, more preferably the full-length sequence of the base sequence, or a sequence which is the same as the base sequence of SEQ ID NO:40 except that not more than 4 bases are substituted at a genetic polymorphism site(s) therein. Specific examples of this set include the set of LMO2736-F488 and LMO2736-R771 in the Examples described below.

(G-2) A set of a mixed forward primer containing in its 3'-side a sequence having not less than 15 consecutive bases, preferably not less than 18 consecutive bases in the base sequence of SEQ ID NO:71, more preferably the full-length sequence of the base sequence, and a mixed reverse primer containing in its 3'-side a sequence having not less than 15 consecutive bases, preferably not less than 18 consecutive bases in the base sequence of SEQ ID NO:76, more preferably the full-length sequence of the base sequence. Specific examples of this set include the set of LMO2736-F488/M and LMO2736-R771/M in the Examples described below.

(H-1) A set of a forward primer containing in its 3'-side a sequence having not less than 15 consecutive bases, preferably not less than 18 consecutive bases in the base sequence of SEQ ID NO:35, more preferably the full-length sequence of the base sequence, or a sequence which is the same as the base sequence of SEQ ID NO:35 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:39, more preferably the full-length sequence of the base sequence, or a sequence which is the same as the base sequence of SEQ ID NO:39 except that not more than 4 bases are substituted at a genetic polymorphism site(s) therein. Specific examples of this set include the set of LMO2736-F530 and LMO2736-R685 in the Examples described below.

(H-2) A set of a mixed forward primer containing in its 3'-side a sequence having not less than 15 consecutive bases, preferably not less than 18 consecutive bases in the base sequence of SEQ ID NO:72, more preferably the full-length sequence of the base sequence, and a mixed reverse primer containing in its 3'-side a sequence having not less than 15 consecutive bases, preferably not less than 18 consecutive bases in the base sequence of SEQ ID NO:75, more preferably the full-length sequence of the base sequence. Specific examples of this set include the set of LMO2736-F530/M and LMO2736-R685/M in the Examples described below.

(I-1) A set of a forward primer containing in its 3'-side a sequence having not less than 15 consecutive bases, preferably not less than 18 consecutive bases in the base sequence of SEQ ID NO:35, more preferably the full-length sequence of the base sequence, or a sequence which is the same as the base sequence of SEQ ID NO:35 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:40, more preferably the full-length sequence of the base sequence, or a sequence which is the same as the base sequence of SEQ ID NO:40 except that not more than 4 bases are substituted at a genetic polymorphism site(s) therein. Specific examples of this set include the set of LMO2736-F530 and LMO2736-R771 in the Examples described below.

(I-2) A set of a forward primer containing in its 3'-side a sequence having not less than 15 consecutive bases, preferably not less than 18 consecutive bases in the base sequence of SEQ ID NO:60, more preferably the full-length sequence of the base sequence, or a sequence which is the same as the base sequence of SEQ ID NO:60 except that not more than 4 bases are substituted at a genetic polymorphism site(s) therein, and a reverse primer containing in its 3'-side a sequence having not less than 15 consecutive bases in the base sequence of SEQ ID NO:61, preferably the full-length sequence of the base sequence, or a sequence which is the same as the base sequence of SEQ ID NO:61 except that not more than 4 bases are substituted at a genetic polymorphism site(s) therein. Specific examples of this set include the set of the LAMP primers LMO2736-1 FIP and LMO2736-1 BIP in the Examples described below.

(I-3) A set of a forward primer containing in its 3'-side a sequence having not less than 15 consecutive bases, preferably not less than 18 consecutive bases in the base sequence of SEQ ID NO:62, more preferably the full-length sequence of the base sequence, or a sequence which is the same as the base sequence of SEQ ID NO:62 except that not more than 4 bases are substituted at a genetic polymorphism site(s) therein, and a reverse primer containing in its 3'-side a sequence having not less than 15 consecutive bases in the base sequence of SEQ ID NO:61, preferably the full-length sequence of the base sequence, or a sequence which is the same as the base sequence of SEQ ID NO:61 except that not more than 4 bases are substituted at a genetic polymorphism site(s) therein. Specific examples of this set include the set of the LAMP primers LMO2736-2 FIP and LMO2736-2 BIP in the Examples described below.

(I-4) A set of a mixed forward primer containing in its 3'-side a sequence having not less than 15 consecutive bases, preferably not less than 18 consecutive bases in the base sequence of SEQ ID NO:72, more preferably the full-length sequence of the base sequence, and a mixed reverse primer containing in its 3'-side a sequence having not less than 15 consecutive bases, preferably not less than 18 consecutive bases in the base sequence of SEQ ID NO:76, more preferably the full-length sequence of the base sequence. Specific examples of this set include the set of LMO2736-F530/M and LMO2736-R771/M in the Examples described below.

(J-1) A set of a forward primer containing in its 3'-side a sequence having not less than 15 consecutive bases, preferably not less than 18 consecutive bases in the base sequence of SEQ ID NO:35, more preferably the full-length sequence of the base sequence, or a sequence which is the same as the base sequence of SEQ ID NO:35 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:41, more preferably the full-length sequence of the base sequence, or a sequence which is the same as the base sequence of SEQ ID NO:41 except that not more than 4 bases are substituted at a genetic polymorphism site(s) therein. Specific examples of this set include the set of LMO2736-F530 and LMO2736-R992 in the Examples described below.

(J-2) A set of a mixed forward primer containing in its 3'-side a sequence having not less than 15 consecutive bases, preferably not less than 18 consecutive bases in the base sequence of SEQ ID NO:72, more preferably the full-length sequence of the base sequence, and a reverse primer containing in its 3'-side a sequence having not less than 15 consecutive bases, preferably not less than 18 consecutive bases in the base sequence of SEQ ID NO:41, more preferably the full-length sequence of the base sequence, or a sequence which is the same as the base sequence of SEQ ID NO:41 except that not more than 4 bases are substituted at a genetic polymorphism site(s) therein. Specific examples of this set include the set of LMO2736-F530/M and LMO2736-R992 in the Examples described below.

(K-1) A set of a forward primer containing in its 3'-side a sequence having not less than 15 consecutive bases, preferably not less than 18 consecutive bases in the base sequence of SEQ ID NO:36, more preferably the full-length sequence of the base sequence, or a sequence which is the same as the base sequence of SEQ ID NO:36 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:39, more preferably the full-length sequence of the base sequence, or a sequence which is the same as the base sequence of SEQ ID NO:39 except that not more than 4 bases are substituted at a genetic polymorphism site(s) therein. Specific examples of this set include the set of LMO2736-F572 and LMO2736-R685 in the Examples described below.

(K-2) A set of a mixed forward primer containing in its 3'-side a sequence having not less than 15 consecutive bases, preferably not less than 18 consecutive bases in the base sequence of SEQ ID NO:73, more preferably the full-length sequence of the base sequence, and a mixed reverse primer containing in its 3'-side a sequence having not less than 15 consecutive bases, preferably not less than 18 consecutive bases in the base sequence of SEQ ID NO:75, more preferably the full-length sequence of the base sequence. Specific examples of this set include the set of LMO2736-F572/M and LMO2736-R685/M in the Examples described below.

(L-1) A set of a forward primer containing in its 3'-side a sequence having not less than 15 consecutive bases, preferably not less than 18 consecutive bases in the base sequence of SEQ ID NO:36, more preferably the full-length sequence of the base sequence, or a sequence which is the same as the base sequence of SEQ ID NO:36 except that not more than 4 bases are substituted at a genetic polymorphism site(s) therein, and a reverse primer containing in its 3'-side a sequence having not less than 15 consecutive bases, preferably not less than 18 consecutive bases in the base sequence of SEQ ID NO:40, more preferably the full-length sequence of the base sequence, or a sequence which is the same as the base sequence of SEQ ID NO:40 except that not more than 4 bases are substituted at a genetic polymorphism site(s) therein. Specific examples of this set include the set of LMO2736-F572 and LMO2736-R771 in the Examples described below.

(L-2) A set of a mixed forward primer containing in its 3'-side a sequence having not less than 15 consecutive bases, preferably not less than 18 consecutive bases in the base sequence of SEQ ID NO:73, more preferably the full-length sequence of the base sequence, and a mixed reverse primer containing in its 3'-side a sequence having not less than 15 consecutive bases, preferably not less than 18 consecutive bases in the base sequence of SEQ ID NO:76, more preferably the full-length sequence of the base sequence. Specific examples of this set include the set of LMO2736-F572/M and LMO2736-R771/M in the Examples described below.

(M-1) A set of a forward primer containing in its 3'-side a sequence having not less than 15 consecutive bases, preferably not less than 18 consecutive bases, more preferably not less than 20 consecutive bases in the base sequence of SEQ ID NO:63, still more preferably the full-length sequence of the base sequence, or a sequence which is the same as the base sequence of SEQ ID NO:63 except that not more than 4 bases are substituted at a genetic polymorphism site(s) therein, and a reverse primer containing in its 3'-side the base sequence of SEQ ID NO:64 or a sequence which is the same as the base sequence of SEQ ID NO:64 except that not more than 4 bases are substituted at a genetic polymorphism site(s) therein. Specific examples of this set include the set of the LAMP primers LMO2736-10 FIP and LMO2736-10 BIP in the Examples described below.

(N-1) A set of a mixed forward primer containing in its 3'-side a sequence having not less than 15 consecutive bases, preferably not less than 18 consecutive bases in the base sequence of SEQ ID NO:71, more preferably the full-length sequence of the base sequence, and a reverse primer containing in its 3'-side a sequence having not less than 15 consecutive bases, preferably not less than 18 consecutive bases in the base sequence of SEQ ID NO:41, more preferably the full-length sequence of the base sequence, or a sequence which is the same as the base sequence of SEQ ID NO:41 except that not more than 4 bases are substituted at a genetic polymorphism site(s) therein. Specific examples of this set include the set of LMO2736-F488/M and LMO2736-R992 in the Examples described below.

(O-1) A set of a mixed forward primer containing in its 3'-side a sequence having not less than 15 consecutive bases, preferably not less than 18 consecutive bases in the base sequence of SEQ ID NO:73, more preferably the full-length sequence of the base sequence, and a reverse primer containing in its 3'-side a sequence having not less than 15 consecutive bases, preferably not less than 18 consecutive bases in the base sequence of SEQ ID NO:41, more preferably the full-length sequence of the base sequence, or a sequence which is the same as the base sequence of SEQ ID NO:41 except that not more than 4 bases are substituted at a genetic polymorphism site(s) therein. Specific examples of this set include the set of LMO2736-F572/M and LMO2736-R992 in the Examples described below.

A primer containing a particular sequence in its 3'-side includes a primer in which an arbitrary sequence is added to the 5'-side of the particular sequence, and a primer composed of the particular sequence. For example, a primer containing the base sequence of SEQ ID NO:26 in its 3'-side includes a primer in which an arbitrary sequence is added to the 5'-side of the base sequence of SEQ ID NO:26, and a primer composed of the base sequence of SEQ ID NO:26.

Preferred specific examples of the genetic polymorphism sites in the base sequences described in (A-1) to (O-1) are as follows. Preferred specific examples of the primers containing a base substitution include primers each containing in its 3'-side a sequence in which at least one base selected from the following specific examples of genetic polymorphism sites is substituted. These specific examples are genetic polymorphism sites specified based on an alignment of the 12 kinds of lmo0084 gene sequences of 12 serotypes of SEQ ID NOs:1 to 12, and an alignment of the 13 kinds of lmo2736 gene sequences of 12 serotypes of SEQ ID NOs:13 to 25. It should noted, however, that genetic polymorphism sites other than the following specific examples may be found in cases where gene sequences of *monocytogenes* bacterial strains of other serotypes or other *monocytogenes* bacterial strains of the same serotypes are further taken into account, and that base substitutions in such sites are acceptable in the present invention. Thus, the genetic polymorphism sites in the sequences in the present invention are not limited to the following specific examples.

SEQ ID NO:26: position 6, position 15, and position 16
SEQ ID NO:27: position 6, position 15, and position 16
SEQ ID NO:28: position 2, position 11, and position 20
SEQ ID NO:29: position 2, position 11, and position 20
SEQ ID NO:30: position 8 and position 11
SEQ ID NO:31: position 8 and position 11
SEQ ID NO:33: position 5, position 18, and position 20
SEQ ID NO:34: position 5 and position 8
SEQ ID NO:35: position 5 and position 11
SEQ ID NO:36: position 5 and position 11
SEQ ID NO:38: position 10 and position 16
SEQ ID NO:39: position 14, position 15, and position 16
SEQ ID NO:40: position 7
SEQ ID NO:58: position 5, position 9, position 11, and position 14
SEQ ID NO:59: position 1 and position 10
SEQ ID NO:60: position 7 and position 13
SEQ ID NO:61: position 5
SEQ ID NO:62: position 7 and position 13
SEQ ID NO:63: position 1, position 4, position 19, and position 25
SEQ ID NO:64: position 6 and position 15

Preferred specific examples of the arbitrary additional sequence that may be present in the 5'-side of the primer include an additional sequence for construction of a LAMP primer. By selecting an arbitrary partial region positioned in the inner side relative to the target region of the primer, and adding the complementary strand of the partial region to the 5'-side of the primer, a LAMP primer can be constructed. Software for designing LAMP primers is known, and such known software can be used for designing LAMP primers for specific detection of the *monocytogenes* bacterium based on the specific primer setting regions (1) to (14) described above.

In the designing of a LAMP primer, the regions F3, F2, F1, B1, B2, and B3, located in this order from the 5'-upstream side, are necessary. A LAMP primer set is constituted with an FIP primer, in which the complementary sequence (the sequence of the antisense strand) of the F1 sequence is added to the 5'-end of F2; a BIP primer, in which the complementary sequence (the sequence of the sense strand) of the B1 sequence is added to the 5'-end of B2; a forward primer that hybridizes to the F3 region, and a reverse primer that hybridizes to the B3 region. The specific primer setting regions (1) to (14) described above may be employed for at least one of F2 and B2 among these, preferably for both of these. When the design is based on the primer sets of (a) to (v), in cases where the amplification size of the set is about 200 to 300 bp, both F2 and B2 may be selected such that they overlap with the primer setting regions. In cases where the amplification size of the set is outside this range, one of F2 and B2 may be selected such that it overlaps with the primer setting regions, and the other may be appropriately selected from candidate sequences proposed by the software.

The following (i) to (iv) are LAMP primer sets each of which was designed based on the set of LMO0084-F286A and LMO0084-R757B, which is one example of the primer set of (A-2), and the set of LMO2736-F530 and LMO2736-R771, which is one example of the primer set of (I-1). Preferred specific examples of the LAMP primer set for detection of the *monocytogenes* bacterium include these sets.

(i) A set of an F3 primer composed of the base sequence of SEQ ID NO:42, a B3 primer composed of the base sequence of SEQ ID NO:43, an FIP primer composed of the base sequence of SEQ ID NO:4, and a BIP primer composed of the base sequence of SEQ ID NO:45.

(ii) A set of an F3 primer composed of the base sequence of SEQ ID NO:46, a B3 primer composed of the base sequence of SEQ ID NO:47, an FIP primer composed of the base sequence of SEQ ID NO:48, and a BIP primer composed of the base sequence of SEQ ID NO:49.

(iii) A set of an F3 primer composed of the base sequence of SEQ ID NO:50, a B3 primer composed of the base sequence of SEQ ID NO:51, an FIP primer composed of the base sequence of SEQ ID NO:52, and a BIP primer composed of the base sequence of SEQ ID NO:53.

(iv) A set of an F3 primer composed of the base sequence of SEQ ID NO:54, a B3 primer composed of the base sequence of SEQ ID NO:55, an FIP primer composed of the base sequence of SEQ ID NO:56, and a BIP primer composed of the base sequence of SEQ ID NO:57.

Isothermal amplification primers used of methods other than the LAMP method may also be designed using known software or the like based on the specific primer setting regions (1) to (14) described above.

Preferred specific examples of the probe for detection of the PCR amplification product include probes containing oligonucleotide portions having the following sequences. The probe containing an oligonucleotide portion having the sequence of SEQ ID NO:85 is a mixed probe of a probe containing an oligonucleotide portion in which n---n is T---A (SEQ ID NO:78), and a probe containing an oligonucleotide portion in which n---n is C---C (SEQ ID NO:79). Similarly, the probe containing an oligonucleotide portion having the sequence of SEQ ID NO:86 is a mixed probe of a probe containing an oligonucleotide portion in which n----n is G----G (SEQ ID NO:83), and a probe containing an oligonucleotide portion in which n----n is C----C (SEQ ID NO:84).

<Probes for LMO0084 Gene>

(SEQ ID NO: 77)
TATTACATTCATAGAATTGACCC (set at position 366 to position 389)

(SEQ ID NO: 85)
ATCTGGTGGCGAGAAGCnGAAnA (set at position 535 to position 558; nGAAn is TGAAA or CGAAC)

(SEQ ID NO: 80)
TACCAAGATTCCAAAAAGAAGCCATG (set at position 686 to position 711)

<Probes for LMO2736 Gene>

(SEQ ID NO: 81)
AAAAAAGGCTGGACTAAAGC (set at position 70 to position 89)

(SEQ ID NO: 82)
ACGTCAAAAAAATCATTATC (set at position 372 to position 393)

(SEQ ID NO: 86)
GTTTTCGGTGCTCAAAAAGGnGCAAnTCC (set at position 619 to position 647; nGCAAn is GGCAAG or CGCAAC)

Each of the probe of SEQ ID NO:85 and the probe of SEQ ID NO:86 is a mixed probe of two kinds of oligonucleotide probes. The mixing ratio of these two kinds of probes, in terms of the molar ratio, may be about 1:5 to 5:1, for example, about 1:2 to 2:1, or about 1:1.5 to 1.5:1. The probes can be preferably used at a mixing ratio of 1:1.

Since the position where each probe is set is as described above, the probe may be used in combination with a primer set which amplifies a region containing this set region. A probe containing an oligonucleotide portion having these sequences can be preferably used as a capture probe for nucleic acid chromatography or a probe for real-time PCR. In cases where the probe is used as a real-time PCR probe, the 5'-end and the 3'-end of the oligonucleotide may be modified with a fluorescent substance and a quencher substance. It is common to modify the 5'-end with a fluorescent substance, and the 3'-end with a quencher substance. Especially preferred combinations of the primers and the probe are described in Table 23 and Table 25 in the following Examples.

EXAMPLES

The present invention is described below more concretely by way of Examples. However, the present invention is not limited to the following Examples.

I. Search for Target Genes

Conventional products for gene testing of the *monocytogenes* bacterium target pathogenicity genes of the *monocytogenes* bacterium, such as the hlyA gene, clpC gene, inlA gene, and plcA gene. However, they are not capable of distinguishing the *monocytogenes* bacterium from other bacteria belonging to the genus *Listeria*. Aiming at establishment of a primer set capable of distinguishing the *monocytogenes* bacterium from other bacteria belonging to the genus *Listeria* with high accuracy, a study was carried out using genes other than the pathogenicity genes described above as targets.

First, the site of http://genolist.pasteur.fr/ListiList/ was used. The information on *monocytogenes* in Accession No. NC_003210.1 and *innocua* in Accession No. NC_003212.1 on this site was utilized. *Listeria innocua* (number of genes: 3068) and *Listeria monocytogenes* (number of genes: 2941), which belong to the genus *Listeria*, were subjected to comparative genomic analysis to narrow down *monocytogenes*-specific genes to 296 genes.

Subsequently, for each of the selected 296 genes, BLAST search was carried out against a database to investigate whether or not the gene can be confirmed to be present in the genome sequences of all isolated strains of *monocytogenes* of each serotype deposited therein. Genes whose presence could not be confirmed in any of the isolated strains were excluded from the candidates. Examples of the search results are shown in Table 3.

study specificity to the *monocytogenes* bacterium. Based on comparison among sequences of various serotypes of *monocytogenes* (using the sequences of the accession numbers described above in Table 2), the PCR primers in this study were designed such that they target common regions. As a result, with LMO 0083, LMO 0444, LMO 0833, and MLO 2387, detection of some of the 6 strains was unsuccessful, or amplification occurred with other bacteria belonging to the genus *Listeria*. Thus, design of a primer set having high specificity was difficult therewith. For example, in the case of the LMO0833 gene, specificity was obtained since no amplification of the bacteria belonging to the genus *Listeria* was found as a result of combination of the primer F329 (ggaaagcaattgtccactcga; SEQ ID NO:65) and the primer R610 (tgttggtgagtagcgtggaa; SEQ ID NO:66). However, *monocytogenes* of the serotype 4a also did not show the amplification. Table 4 shows examples of the PCR results for the candidate genes. With LMO 0084 and LMO 2736, specific amplification products were obtained only from the 6 strains of the *monocytogenes* bacterium. For comparison, two commercially available kits for gene testing of the

TABLE 3

|  | Serotype | LM000038 | LM000077 | LM000313 | LMO02387 | LMO02736 |
|---|---|---|---|---|---|---|
| *L. monocytogenes* | 1/2a | 18 | 18 | 1 | 18 | 18 |
| *L. monocytogenes* | 1/2b | 5 | 5 | 2 | 5 | 5 |
| *L. monocytogenes* | 1/2c | 2 | 2 | 2 | 2 | 2 |
| *L. monocytogenes* | 3a | 2 | 2 | 0 | 2 | 2 |
| *L. monocytogenes* | 3b | 1 | 1 | 0 | 1 | 1 |
| *L. monocytogenes* | 3c | 1 | 1 | 1 | 1 | 1 |
| *L. monocytogenes* | 4a | 0 | 3 | 0 | 3 | 3 |
| *L. monocytogenes* | 4b | 12 | 12 | 5 | 12 | 12 |
| *L. monocytogenes* | 4c | 1 | 1 | 0 | 1 | 1 |
| *L. monocytogenes* | 4d | 1 | 1 | 0 | 1 | 1 |
| *L. monocytogenes* | 4e | 0 | 0 | 0 | 1 | 1 |
| *L. monocytogenes* | 7 | 1 | 1 | 0 | 1 | 1 |
|  |  | There is/are an isolated strain(s) for which the presence of the gene cannot be confirmed. ↓ Excluded from candidates | There is/are an isolated strain(s) for which the presence of the gene cannot be confirmed. ↓ Excluded from candidates | There is/are an isolated strain(s) for which the presence of the gene cannot be confirmed. ↓ Excluded from candidates | The presence of the gene could be confirmed in genomic sequences of all isolated strains deposited. ↓ Selected as a candidate | The presence of the gene could be confirmed in genomic sequences of all isolated strains deposited. ↓ Selected as a candidate |

By this, the candidate genes were finally narrowed down to 6 genes (LMO 0083, LMO 0084, LMO 0444, LMO 0833, LMO 2387, and LMO 2736).

For each of the 6 genes, a plurality of PCR primers were designed, and PCR was actually carried out for the 6 strains of the *monocytogenes* bacterium (serotypes 1/2a, 1/2b, 1/2c, 4a, 4b, and 4d) and 3 strains of other bacteria belonging to the genus *Listeria* (*L. innocua, L. grayi,* and *L. ivanovii*), to

*monocytogenes* bacterium were used for detection of the same bacterial strains. As a result, neither of these succeeded in specific detection of the *monocytogenes* bacteria used herein (Table 4). From these results, the candidate genes were narrowed down to LMO 0084 and LMO 2736, and construction of *monocytogenes* bacterium-specific primers was attempted therewith.

TABLE 4

| Gene name | Description | *L. monocytogenes* GTC02947 1/2a | *L. monocytogenes* GTC02948 1/2b | *L. monocytogenes* JCM7672 1/2c | *L. monocytogenes* JCM7674 4a | *L. monocytogenes* JCM7675 4b |
|---|---|---|---|---|---|---|
| LMO 0083 | similar to transcription regulator | − | + | + | + | + |
| LMO 0084 | similar to oxidoreductases | + | + | + | + | + |

TABLE 4-continued

| | | | | | | |
|---|---|---|---|---|---|---|
| LMO 0444 | conserved hypothetical protein | + | + | + | − | − |
| LMO 0833 | similar to transcription regulator | + | + | + | − | + |
| LMO 2387 | conserved hypothetical protein | + | + | + | + | + |
| LMO 2736 | conserved hypothetical protein | + | + | + | + | + |
| hlyA gene | Psthogenic Bacterial Multiplex PCR Detection kit TA10 (TAKARA: RR106A) | + | + | + | − | − |
| (Unknown) | mericon L. monocytogenes Kit (QIAGEN: 290023) | + | + | + | + | + |

| Gene name | Description | L. monocytogenes JCM7680 4d | L. gayi GTC02964T − | L. innocua GTC16426T − | L. Ivaimii JCM7681 − |
|---|---|---|---|---|---|
| LMO 0083 | similar to transcription regulator | + | − | − | − |
| LMO 0084 | similar to oxidoreductases | + | − | − | − |
| LMO 0444 | conserved hypothetical protein | − | − | − | − |
| LMO 0833 | similar to transcription regulator | + | − | − | − |
| LMO 2387 | conserved hypothetical protein | + | + | − | + |
| LMO 2736 | conserved hypothetical protein | + | − | − | − |
| hlyA gene | Pathogenic Bacterial Multiplex PCR Detection kit TA10 (TAKARA: RR106A) | − | − | − | − |
| (Unknown) | mericon L. monocytogenes Kit (QIAGEN: 290023) | + | + | + | + |

II. Construction of *monocytogenes* Bacterium-Specific Primer Sets

Base sequences of the two genes LMO 0084 and LMO 2736 in various serotypes, identified by the narrowing down as described above, were studied in more detail, and a large number of primers were designed therefrom. By performing a PCR study using an increased number of bacterial strains, construction of primers for specific detection of the *monocytogenes* bacterium with high accuracy was attempted.

<Methods>

1. Bacterial Strains Used

The bacterial strains subjected to the PCR test (Table 5-1 to Table 5-3) were obtained from Microbe Division, RIKEN BioResource Research Center (JCM); Center for Conservation of Microbial Genetic Resource, Organization for Research and Community Development, Gifu University (GTC); Department of Biotechnology, National Institute of Technology and Evaluation (IFO)); JA Zen-nob Institute of Animal Health (JA); and Institute of Applied Microbiology, University of Tokyo (IMCB).

TABLE 5-1

*Monocytogenes* bacterium

| Bacterial strain No. | Microorganism name | Resource name | Serotype |
|---|---|---|---|
| 1 | L. monocytogenes | GTC02947 | 1/2a |
| 2 | L. monocytogenes | GTC02948 | 1/2b |
| 3 | L. monocytogenes | JCM7672 | 1/2c |
| 4 | L. monocytogenes | JCM7673 | 3a |
| 5 | L. monocytogenes | JCM7677 | 3b |
| 6 | L. monocytogenes | JCM7678 | 3c |
| 7 | L. monocytogenes | JCM7674 | 4a |
| 8 | L. monocytogenes | JCM7675 | 4b |

TABLE 5-1-continued

*Monocytogenes* bacterium

| Bacterial strain No. | Microorganism name | Resource name | Serotype |
|---|---|---|---|
| 9 | L. monocytogenes | JCM7680 | 4d |
| 10 | L. monocytogenes | GTC02957 | 5 |

TABLE 5-2

Bacteria belonging to the genus *Listeria* other than the *monocytogenes* bacterium

| Bacterial strain No. | Microorganism name | Resource name |
|---|---|---|
| 11 | L. ivanovii | GTC02961 |
| 12 | L. ivanovii subsp. ivanovii | JCM7681 |
| 13 | L. ivanovii subsp. ivanovii | GTC01640T |
| 14 | L. ivanovii subsp. londoniensis | GTC01641 |
| 15 | L. innocua | GTC16426T |
| 16 | L. innocua | GTC02960 |
| 17 | L. welshimeri | GTC02963T |
| 18 | L. seeligeri | GTC16428T |
| 19 | L. grayi | GTC02964T |
| 20 | L. murrayi | GTC02964 |
| 21 | L. marthii | GTC16430T |
| 22 | L. rocourtiae | GTC16429T |

TABLE 5-3

Food-poisoning bacteria other than *Listeria* bacteria which tend to cause problems in the field of foods

| Bacterial strain No. | Microorganism name | Resource name | Serotype |
|---|---|---|---|
| 23 | *Escherichia coli* | ATCC10798 | |
| 24 | *Salmonella* subsp. *enterica* (I) | JA.107 | Type I |
| 25 | *Salmonella* subsp. *salamae* (II) | JA.125 | Type II |
| 26 | *Salmonella* subsp. *arizonae* (IIIa) | JA.76 | Type IIIa |
| 27 | *Salmonella* subsp. *diarizinae* (IIIb) | JA.129 | Type IIIb |
| 28 | *Salmonella* subsp. *houtenae* (IV) | JA.n-22 | Type IV |
| 29 | *Salmonella bongori* (V) | JA.94 | Type V |
| 30 | *Salmonella* subsp. *enterica* Typhimurium | ATCC43971 | |
| 31 | *Staphylococcus aureus* | ATCC6538P | |
| 32 | *Staphylococcus aureus* | ATCC25923 | |
| 33 | *Staphylococcus aureus* | ATCC29213 | |
| 34 | *Staphylococcus aureus* | JMC2197 | |
| 35 | *Staphylococcus aureus* | IMCB.IMA2 | |
| 36 | *Staphylococcus cohnii* | ATCC29974 | |
| 37 | *Staphylococcus haemolyticus* | ATCC29970 | |
| 38 | *Staphylococcus hyicus* subsp. | ATCC11249 | |
| 39 | *Staphylococcus intermedius* | ATCC29663 | |
| 40 | *Staphylococcus saprophyticus* | ATCC15305 | |
| 41 | *Citrobacter freundii* | ATCC8090 | |
| 42 | *Citrobacter freundii* | ATCC8043 | |
| 43 | *Proteus vulgaris* | IFO3988 | |
| 44 | *Lactobacillus bulgaricus* | IFO13953 | |
| 45 | *Lactobacillus helveticus* | IFO3809 | |
| 46 | *Streptococcus* sp. | IFO3535 | |
| 47 | *Streptococcus sanguis* | ATCC10558 | |
| 48 | *Streptococcus mitis* | ATCC6249 | |

2. Primers and PCR Reaction Conditions

Various primers were designed based on sequence information for the lmo0084 gene (SEQ ID NOs:1 to 12) and the lmo2736 gene (SEQ ID NOs:13 to 25) in various serotypes of *Listeria monocytogenes*. Table 6 shows part of those sequences. For the lmo0084 gene, primers of SEQ ID NOs:26, 28, and 30 were designed such that they reflect genetic polymorphism in the serotype 1/2a of the *monocytogenes* bacterium, and primers of SEQ ID NOs:27, 29, and 31 were designed such that they reflect genetic polymorphism in the serotype 4a. For the lmo2736 gene, primers of SEQ ID NOs:32, 37, and 41 were designed such that they reflect common sequences among the various serotypes of the *monocytogenes* bacterium, and primers of SEQ ID NOs:33, 34, 35, 36, 38, 39, and 40 were designed such that they reflect genetic polymorphism in the serotype 1/2c of the *monocytogenes* bacterium. The designed PCR primers were synthesized by custom synthesis by Fasmac Co., Ltd. Template DNA was obtained by extracting genomic DNA from each bacterial strain using a mericon DNA Bacteria Plus Kit (QIAGEN).

TABLE 6

| Target gene | Oligonucleotide name [a] | Sequence [b] | Setting position [c] | SEQ ID NO. |
|---|---|---|---|---|
| lmo0084 | LMO0084-F286A | AGCCGTCCAGAAAGCATCAA<br>-----*---------**---- | 286 to 305 | 26 |
| | LMO0084-F286B | AGCCGCCCAGAAAGTCTCAA<br>-----*---------**---- | 286 to 305 | 27 |
| | LMO0084-F281A | TCGATAGCCGTCCAGAAAGC<br>-*---------*---------* | 281 to 300 | 28 |
| | LMO0084-F281B | TTGATAGCCGCCCAGAAAGT<br>-*---------*---------* | 281 to 300 | 29 |
| | LMO0084-R757A | GCTCGTCGGCGATTTCTTTC<br>--------*--*--------- | 738 to 757 | 30 |
| | LMO0084-R757B | GCTCGTCGGCTATTTCTTTC<br>--------*--*--------- | 738 to 757 | 31 |
| lmo2736 | LMO2736-F8 | TCGTCATCGCACCTGATTCA<br>-------------------- | 8 to 27 | 32 |
| | LMO2736-F222 | GGCCTCCTACGGTATTCACG<br>----*------------*-* | 222 to 241 | 33 |
| | LMO2736-F488 | CCGGTGGCATTCATTTGCAA<br>----*--*------------ | 488 to 507 | 34 |
| | LMO2736-F530 | GCAACCTTAACCCAAAGCTG<br>----*------*-------- | 530 to 549 | 35 |
| | LMO2736-F572 | CCTGTGACGTSACGAATCCA<br>----*------*-------- | 572 to 591 | 36 |
| | LMO2736-R176 | TCCACCTCGGAAGACTCACT<br>-------------------- | 157 to 176 | 37 |
| | LMO2736-R591 | TGGATTCGTCACGTCACAGG<br>---------*-----*---- | 572 to 591 | 38 |
| | LMO2736-R685 | AGTTCTGCATGGCGTTCTCT<br>--------------***---- | 666 to 685 | 39 |
| | LMO2736-R771 | TAGTCCAGCAGCGATACCAC<br>-------*------------ | 752 to 771 | 40 |
| | LMO2736-R992 | TTGTTTTCGAGTGCAAGGCT<br>-------------------- | 973 to 992 | 41 |

[a] In the oligonucleotide names, F represents "forward", and R represents "reverse".
[b] * represents a base showing polymorphism based on comparison among the sequences of SEQ ID NOs: 1 to 25.
[c] The setting position is described using as a standard SEQ ID NO: 1 in the cases of the primers targeting lmo0084, and SEQ ID NO: 13 in the cases of the primers targeting lmo2736.

The composition of the PCR reaction liquid is shown below in Table 7. The PCR was carried out using GeneAmp PCR System 9700. The reaction cycle was as follows: 94° C. for 2 minutes→(94° C. for 20 seconds→60° C. for 20 seconds→72° C. for 40 seconds)×30 cycles→72° C. for 7 minutes→4° C.

TABLE 7

| Reagent | Manufacturer | Code. No. | Liquid volume (μL) |
|---|---|---|---|
| TaKaRa Ex Taq (5 U/μl) | TaKaRa | RR01AM | 0.2 |
| 10 × Ex Taq Buffer (Mg$^{2+}$ free) | TaKaRa | RR01AM | 2.0 |
| MgCl$_2$ (25 mM) | TaKaRa | RR01AM | 1.6 |
| dNTP Mixture (2.5 mM each) | TaKaRa | RR01AM | 1.6 |
| 100 μM Primer F | Fasmac | — | 0.1 |
| 100 μM Primer R | Fasmac | — | 0.1 |
| D.W. | — | — | 12.4 |
| 1 ng/μT Template DNA | — | — | 2.0 |
| Per tube | | | 20.0 |

3. Selective Isolation Medium for *monocytogenes*

Various bacteria belonging to the genus *Listeria* were plated on ALOA agar medium (Sysmex Corporation) or CHROMagar medium (Kanto Chemical Co., Inc.), and cultured at 37° C. for about 24 hours, followed by observation of colonies. The *monocytogenes* bacterium forms bluish-green colonies accompanied by milky-white halos on ALOA agar medium, and blue colonies accompanied by milky-white halos on CHROMagar medium.

<Results>

Figures 1, 2:
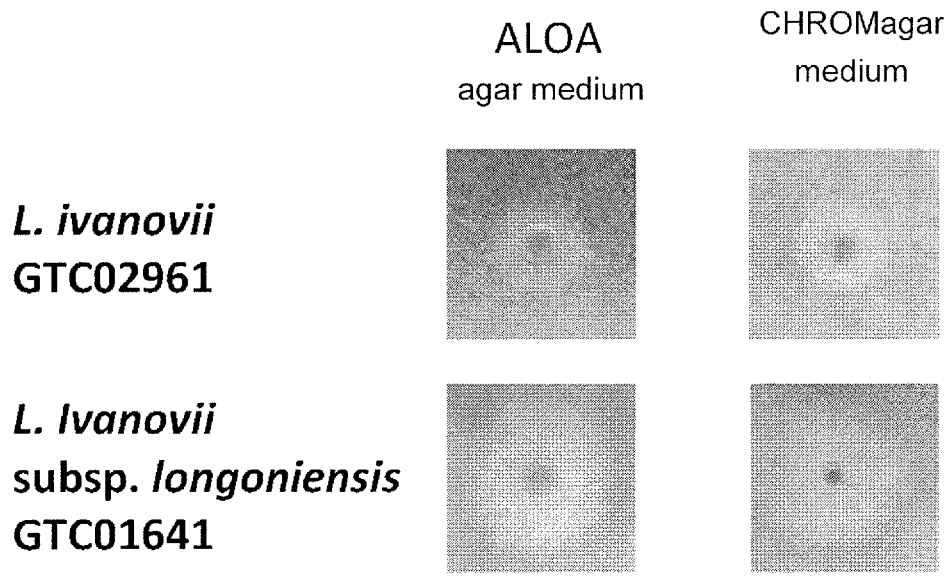
Figures 1, 2, 3:
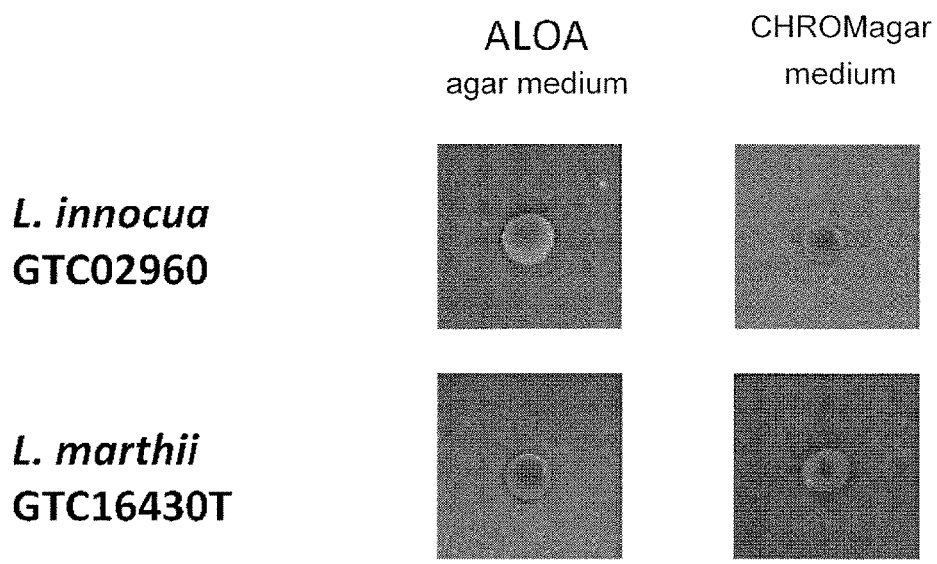
Figures 1, 2:
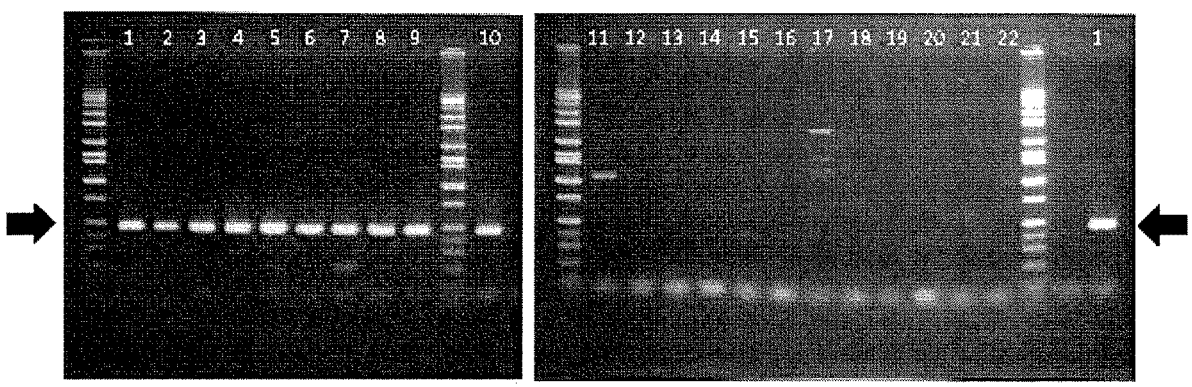
Figure 2:
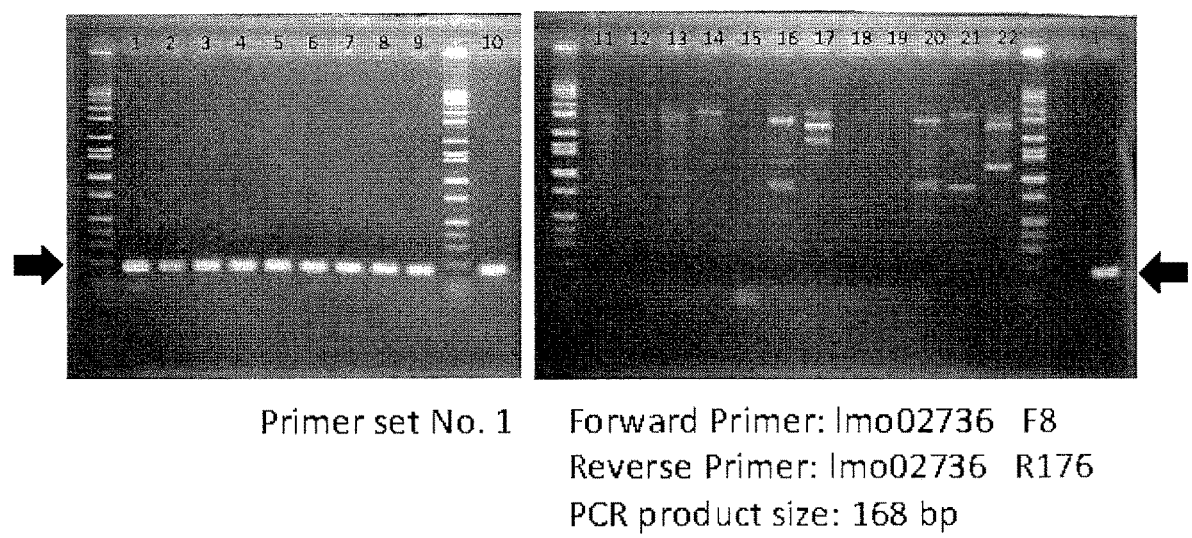

In the halo formation test, all strains of the *monocytogenes* bacterium showed formation of halos to give positive results although some strains such as the bacterial strain No. 4 partially showed colonies forming no halo. On the other hand, *L. ivanovii* (bacterial strain Nos. 11, 12, 13, and 14) and *L. seeligeri* (bacterial strain No. 18) showed false-positive results. No colony formation was found for 26 food-poisoning bacterial strains other than those of the genus *Listeria* (bacterial strain Nos. 23 to 48). Part of the results of the halo test are shown in FIG. 1-1 to FIG. 1-3.

As a result of study using various combinations of the designed primers, the *monocytogenes* bacterium could be specifically detected with the combinations shown in Table 8-1 to Table 8-4 independent of genetic polymorphism. None of these combinations produced a PCR product having the specific size from bacteria belonging to the genus *Listeria* other than the *monocytogenes* bacterium (bacterial strain Nos. 11 to 22), or from the other 26 food-poisoning bacterial strains (bacterial strain Nos. 23 to 48) (Table 9-1 to Table 9-6). Examples of the PCR results are shown in FIG. 2-1 and FIG. 2-2.

Since *L. ivanovii* and *L. seeligeri* form halos similarly to the *monocytogenes* bacterium on ALOA agar medium and CHROMagar medium, which are commonly used for selective isolation of the *monocytogenes* bacterium, they cannot be easily distinguished from the *monocytogenes* bacterium. However, with the primer sets shown in Table 8-1 to Table 8-4, various isolated bacterial strains of these bacteria belonging to the genus *Listeria* showed no amplification, giving negative results. On the other hand, the *monocytogenes* bacterial strain JMC7673 (bacterial strain No. 4 in the tables) could also be detected as the *monocytogenes* bacterium in spite of the fact that it also produces colonies forming no halo. Thus, it could be confirmed that the primer sets shown in Table 8-1 to Table 8-4 have very high specificities to the *monocytogenes* bacterium. It could be further confirmed that those primer sets are superior to the conventional *monocytogenes* bacterium detection PCR kits shown in Table 3.

TABLE 8-1

PCR for detection of the lmo0084 gene, and halo formation

| primer set No. | F primer | SEQ ID NO. | R primer | SEQ ID NO. | Amplification size (bp) | Bacterial strain No. (*monocytogenes* bacterium) | | | | | | | | | |
|---|---|---|---|---|---|---|---|---|---|---|---|---|---|---|---|
| | | | | | | 1 | 2 | 3 | 4 | 5 | 6 | 7 | 8 | 9 | 10 |
| 6 | F286A | 26 | R757A | 30 | 471 | + | + | + | + | + | + | + | + | + | + |
| 8 | F286A | 26 | R757B | 31 | 471 | + | + | + | + | + | + | + | + | + | + |
| 14 | F286B | 27 | R757A | 30 | 471 | + | + | + | + | + | + | + | + | + | + |
| 16 | F286B | 27 | R757B | 31 | 471 | + | + | + | + | + | + | + | + | + | + |
| 2 | F281A | 28 | R757A | 30 | 476 | + | + | + | + | + | + | + | + | + | + |
| 4 | F281A | 28 | R757B | 31 | 476 | + | + | + | + | + | + | + | + | + | + |
| 10 | F281B | 29 | R757A | 30 | 476 | + | + | + | + | + | + | + | + | + | + |
| 12 | F281B | 29 | R757B | 31 | 476 | + | + | + | + | + | + | + | + | + | + |
| Halo formation | | | | | | (+) | (+) | (+) | (+/−) | (+) | (+) | (+) | (+) | (+) | (+) |

TABLE 8-2

PCR for detection of the lmo0084 gene, and halo formation

| primer set No. | F primer | R primer | Amplification size (bp) | Bacterial strain No. (bacteria belonging to the genus *Listeria* other than the *monocytogenes* bacterium) | | | | | | | | | | | |
|---|---|---|---|---|---|---|---|---|---|---|---|---|---|---|---|
| | | | | 11 | 12 | 13 | 14 | 15 | 16 | 17 | 18 | 19 | 20 | 21 | 22 |
| 6 | F286A | R7C7A | 471 | − | − | − | − | − | − | − | − | − | − | − | − |
| 8 | F286A | R757B | 471 | − | − | − | − | − | − | − | − | − | − | − | − |
| 14 | F286B | R7S7A | 471 | − | − | − | − | − | − | − | − | − | − | − | − |
| 16 | F286B | R757B | 471 | − | − | − | − | − | − | − | − | − | − | − | − |
| 2 | F281A | R757A | 476 | − | − | − | − | − | − | − | − | − | − | − | − |
| 4 | F281A | R757B | 476 | − | − | − | − | − | − | − | − | − | − | − | − |

TABLE 8-2-continued

PCR for detection of the lmo0084 gene, and halo formation

| primer set No. | F primer | R primer | Amplification size (bp) | Bacterial strain No. (bacteria belonging to the genus Listeria other than the monocytogenes bacterium) | | | | | | | | | | | |
|---|---|---|---|---|---|---|---|---|---|---|---|---|---|---|---|
| | | | | 11 | 12 | 13 | 14 | 15 | 16 | 17 | 18 | 19 | 20 | 21 | 22 |
| 10 | F281B | R757A | 476 | – | – | – | – | – | – | – | – | – | – | – | – |
| 12 | F281B | R757B | 476 | – | – | – | – | – | – | – | – | – | – | – | – |
| | | Halo formation | | (+) | (+) | (+) | (+) | (–) | (–) | (–) | (+) | (–) | (–) | (–) | (–) |

TABLE 8-3

PCR for detection of the lmo2736 gene, and halo formation

| primer set No. | F primer | SEQ ID NO. | R primer | SEQ ID NO. | Amplification size (bp) | Bacterial strain No. (monocytogenes bacterium) | | | | | | | | | |
|---|---|---|---|---|---|---|---|---|---|---|---|---|---|---|---|
| | | | | | | 1 | 2 | 3 | 4 | 5 | 6 | 7 | 8 | 9 | 10 |
| 1 | F8 | 32 | R176 | 37 | 168 | + | + | + | + | + | + | + | + | + | + |
| 3 | F222 | 33 | R591 | 38 | 369 | + | + | + | + | + | + | + | + | + | + |
| 4 | F488 | 34 | R591 | 38 | 103 | + | + | + | + | + | + | + | + | + | + |
| 5 | F488 | 34 | R685 | 39 | 197 | + | + | + | + | + | + | + | + | + | + |
| 6 | F488 | 34 | R771 | 40 | 283 | + | + | + | + | + | + | + | + | + | + |
| 9 | F530 | 35 | R685 | 39 | 155 | + | + | + | + | + | + | + | + | + | + |
| 10 | F530 | 35 | R771 | 40 | 241 | + | + | + | + | + | + | + | + | + | + |
| 12 | F530 | 35 | R992 | 41 | 462 | + | + | + | + | + | + | + | + | + | + |
| 13 | F572 | 36 | R685 | 39 | 113 | + | + | + | + | + | + | + | + | + | + |
| 14 | F572 | 36 | R771 | 40 | 199 | + | + | + | + | + | + | + | + | + | + |
| | | | Halo formation | | | (+) | (+) | (+) | (+/–) | (+) | (+) | (+) | (+) | (+) | (+) |

TABLE 8-4

PGR for detection of the lmo2736 gene, and halo formation

| primer set No. | F primer | R primer | Amplification size (bp) | Bacterial strain No. (bacteria belonging to the genus Listeria other than the monocytogenes bacterium) | | | | | | | | | | | |
|---|---|---|---|---|---|---|---|---|---|---|---|---|---|---|---|
| | | | | 11 | 12 | 13 | 14 | 15 | 16 | 17 | 18 | 19 | 20 | 21 | 22 |
| 1 | F8 | R176 | 168 | – | – | – | – | – | – | – | – | – | – | – | – |
| 3 | F222 | R591 | 369 | – | – | – | – | – | – | – | – | – | – | – | – |
| 4 | F488 | R591 | 103 | – | – | – | – | – | – | – | – | – | – | – | – |
| 5 | F488 | R685 | 197 | – | – | – | – | – | – | – | – | – | – | – | – |
| 6 | F488 | R771 | 283 | – | – | – | – | – | – | – | – | – | – | – | – |
| 9 | F530 | R685 | 155 | – | – | – | – | – | – | – | – | – | – | – | – |
| 10 | F530 | R771 | 241 | – | – | – | – | – | – | – | – | – | – | – | – |
| 12 | F530 | R992 | 462 | – | – | – | – | – | – | – | – | – | – | – | – |
| 13 | F572 | R685 | 113 | – | – | – | – | – | – | – | – | – | – | – | – |
| 14 | F572 | R771 | 199 | – | – | – | – | – | – | – | – | – | – | – | – |
| | | Halo formation | | (+) | (+) | (+) | (+) | (–) | (–) | (–) | (+) | (–) | (–) | (–) | (–) |

TABLE 9-1

| | LMO 00084 | | | 23 Escherichia coli ATCC10798 | 24 Salmonella subsp. enterica (I) JA.107 | 25 Salmonella subsp. salamae (II) JA.125 | 26 Salmonella subsp. arizonae (IIIa) JA.76 | 27 Salmonella subsp. diariznae (IIIb) JA.129 |
|---|---|---|---|---|---|---|---|---|
| No. | primer F | primer R | size | | | | | |
| 6 | 286 A | 757 A | 471 | – | – | – | – | – |
| 8 | 286 A | 757 B | 471 | – | – | – | – | – |
| 14 | 286 B | 757 A | 471 | – | – | – | – | – |
| 16 | 286 B | 757 B | 471 | – | – | – | – | – |
| 2 | 281 A | 757 A | 476 | – | – | – | – | – |

TABLE 9-1-continued

| | | | | | | | | | |
|---|---|---|---|---|---|---|---|---|---|
| 4 | 281 | A | 757 | B | 476 | – | – | – | – | – |
| 10 | 281 | B | 757 | A | 476 | – | – | – | – | – |
| 12 | 281 | B | 757 | B | 476 | – | – | – | – | – |

| | LMO 00084 | | | | 28<br>*Salmonella*<br>subsp.<br>*houtenae*<br>(IV) | 29<br>*Salmonella*<br>*bongori*<br>(V) | 30<br>*Salmonella*<br>subsp.<br>*enterica*<br>*Typhimurium* | 31<br>*Staphylococcus*<br>*aureus* |
|---|---|---|---|---|---|---|---|---|
| No. | primer F | | primer R | size | JA.n-22 | JA.94 | ATCC43971 | ATCC6538P |
| 6 | 286 | A | 757 | A | 471 | – | – | – | – |
| 8 | 286 | A | 757 | B | 471 | – | – | – | – |
| 14 | 286 | B | 757 | A | 471 | – | – | – | – |
| 16 | 286 | B | 757 | B | 471 | – | – | – | – |
| 2 | 281 | A | 757 | A | 476 | – | – | – | – |
| 4 | 281 | A | 757 | B | 476 | – | – | – | – |
| 10 | 281 | B | 757 | A | 476 | – | – | – | – |
| 12 | 281 | B | 757 | B | 476 | – | – | – | – |

TABLE 9-2-continued

| | LMO 00084 | | | | 32<br>*Staphylococcus*<br>*aureus* | 33<br>*Staphylococcus*<br>*aureus* | 34<br>*Staphylococcus*<br>*aureus* | 35<br>*Staphylococcus*<br>*aureus* | 36<br>*Staphylococcus*<br>*cohnii* |
|---|---|---|---|---|---|---|---|---|---|
| No. | primer F | | primer R | size | ATCC25923 | ATCC29213 | JMC2197 | IMCB.IMA2 | ATCC29974 |
| 6 | 286 | A | 757 | A | 471 | – | – | – | – | – |
| 8 | 286 | A | 757 | B | 471 | – | – | – | – | – |
| 14 | 286 | B | 757 | A | 471 | – | – | – | – | – |
| 16 | 286 | B | 757 | B | 471 | – | – | – | – | – |
| 2 | 281 | A | 757 | A | 476 | – | – | – | – | – |
| 4 | 281 | A | 757 | B | 476 | – | – | – | – | – |
| 10 | 281 | B | 757 | A | 476 | – | – | – | – | – |
| 12 | 281 | B | 757 | B | 476 | – | – | – | – | – |

| | LMO 00084 | | | | 37<br>*Staphylococcus*<br>*haemolyticus* | 38<br>*Staphylococcus*<br>*hyicus* subsp. | 39<br>*Staphylococcus*<br>*intermedius* | 40<br>*Staphylococcus*<br>*saprophyticus* |
|---|---|---|---|---|---|---|---|---|
| No. | primer F | | primer R | size | ATCC29970 | ATCC11249 | ATCC29663 | ATCC15305 |
| 6 | 286 | A | 757 | A | 471 | – | – | – | – |
| 8 | 286 | A | 757 | B | 471 | – | – | – | – |
| 14 | 286 | B | 757 | A | 471 | – | – | – | – |
| 16 | 286 | B | 757 | B | 471 | – | – | – | – |
| 2 | 281 | A | 757 | A | 476 | – | – | – | – |
| 4 | 281 | A | 757 | B | 476 | – | – | – | – |
| 10 | 281 | B | 757 | A | 476 | – | – | – | – |
| 12 | 281 | B | 757 | B | 476 | – | – | – | – |

TABLE 9-3

| | LMO 00084 | | | | 41<br>*Citrobacter*<br>*freundii* | 42<br>*Citrobacter*<br>*freundii* | 43<br>*Proteus*<br>*vulgaris* | 44<br>*Lactbacillus*<br>*bulgarius* | 45<br>*Lactbacillus*<br>*halveticus* |
|---|---|---|---|---|---|---|---|---|---|
| No. | primer: F | | primer: R | size | ATCC8090 | ATCC8043 | IFO3988 | IFO13953 | IFO3809 |
| 6 | 286 | A | 757 | A | 471 | – | – | – | – | – |
| 8 | 286 | A | 757 | B | 471 | – | – | – | – | – |
| 14 | 286 | B | 757 | A | 471 | – | – | – | – | – |
| 16 | 286 | B | 757 | B | 471 | – | – | – | – | – |
| 2 | 281 | A | 757 | A | 476 | – | – | – | – | – |
| 4 | 281 | A | 757 | B | 476 | – | – | – | – | – |
| 10 | 281 | B | 757 | A | 476 | – | – | – | – | – |
| 12 | 281 | B | 757 | B | 476 | – | – | – | – | – |

TABLE 9-3-continued

| | LMO 00084 | | | | | 46 Streptcoccus sp. IFO3535 | 47 Streptcoccus sanguis ATCC10558 | 48 Streptcoccus mitis ATCC6249 |
|---|---|---|---|---|---|---|---|---|
| No. | primer: F | | primer: R | | size | | | |
| 6 | 286 | A | 757 | A | 471 | − | − | − |
| 8 | 286 | A | 757 | B | 471 | − | − | − |
| 14 | 286 | B | 757 | A | 471 | − | − | − |
| 16 | 286 | B | 757 | B | 471 | − | − | − |
| 2 | 281 | A | 757 | A | 476 | − | − | − |
| 4 | 281 | A | 757 | B | 476 | − | − | − |
| 10 | 281 | B | 757 | A | 476 | − | − | − |
| 12 | 281 | B | 757 | B | 476 | − | − | − |

TABLE 9-4

| | LMO 02736 | | | 23 Escherichia coli ATCC10798 | 24 Salmonella subsp. enterica (I) JA.107 | 25 Salmonella subsp salamae (II) JA.125 | 26 Salmonella subsp arizonae (IIIa) JA.76 | 27 Salmonella subsp dianzinae (IIIb) JA.129 | 28 Salmonella subsp houtenae (IV) JA.n-22 |
|---|---|---|---|---|---|---|---|---|---|
| No | primer: F | printer: R | size | | | | | | |
| 1 | 8 | 176 | 168 | − | − | − | − | − | − |
| 3 | 222 | 591 | 369 | − | − | − | − | − | − |
| 4 | 488 | 591 | 103 | − | − | − | − | − | − |
| 5 | 488 | 685 | 197 | − | − | − | − | − | − |
| 6 | 488 | 771 | 283 | − | − | − | − | − | − |
| 8 | 488 | 992 | 504 | − | − | − | − | − | − |
| 9 | 530 | 685 | 155 | − | − | − | − | − | − |
| 10 | 530 | 771 | 241 | − | − | − | − | − | − |
| 12 | 530 | 992 | 462 | − | − | − | − | − | − |
| 13 | 572 | 685 | 113 | − | − | − | − | − | − |
| 14 | 572 | 771 | 199 | − | − | − | − | − | − |

| | LMO 02736 | | | 29 Salmonela bongori (V) JA.94 | 30 Salmonella subsp enterica Typhimurium ATCC43971 | 31 Staphylococcus aureus ATCC6538P |
|---|---|---|---|---|---|---|
| No | primer: F | printer: R | size | | | |
| 1 | 8 | 176 | 168 | − | − | − |
| 3 | 222 | 591 | 369 | − | − | − |
| 4 | 488 | 591 | 103 | − | − | − |
| 5 | 488 | 685 | 197 | − | − | − |
| 6 | 488 | 771 | 283 | − | − | − |
| 8 | 488 | 992 | 504 | − | − | − |
| 9 | 530 | 685 | 155 | − | − | − |
| 10 | 530 | 771 | 241 | − | − | − |
| 12 | 530 | 992 | 462 | − | − | − |
| 13 | 572 | 685 | 113 | − | − | − |
| 14 | 572 | 771 | 199 | − | − | − |

TABLE 9-5

| | LMO 02736 | | | 32 Staphylococcus aurous ATCC25923 | 33 Staphylococcus aureus ATCC29213 | 34 Staphylococcus aureus JMC2197 | 35 Staphylococcus aureus IMCB.IMA2 | 36 Staphylococcus cohnii ATCC29974 | 37 Staphylococcus haemotyticus ATCC29970 |
|---|---|---|---|---|---|---|---|---|---|
| No | primer: F | primer: R | size | | | | | | |
| 1 | 8 | 176 | 168 | − | − | − | − | − | − |
| 3 | 222 | 591 | 369 | − | − | − | − | − | − |
| 4 | 488 | 591 | 103 | − | − | − | − | − | − |
| 5 | 488 | 685 | 197 | − | − | − | − | − | − |
| 6 | 488 | 771 | 283 | − | − | − | − | − | − |
| 8 | 488 | 992 | 504 | − | − | − | − | − | − |

TABLE 9-5-continued

| No | primer: F | primer: R | size | | | | | |
|----|-----------|-----------|------|---|---|---|---|---|
| 9  | 530 | 685 | 155 | – | – | – | – | – |
| 10 | 530 | 771 | 241 | – | – | – | – | – |
| 12 | 530 | 992 | 462 | – | – | – | – | – |
| 13 | 572 | 685 | 113 | – | – | – | – | – |
| 14 | 572 | 771 | 199 | – | – | – | – | – |

| | LMO 02736 | | | 38 *Staphylococcus hyicus* subsp. ATCC11249 | 39 *Staphylococcus intermedius* ATCC29663 | 40 *Staphylococcus saprophyticus* ATCC15305 |
|---|---|---|---|---|---|---|
| No | primer: F | primer: R | size | | | |
| 1  | 8   | 176 | 168 | – | – | – |
| 3  | 222 | 591 | 369 | – | – | – |
| 4  | 488 | 591 | 103 | – | – | – |
| 5  | 488 | 685 | 197 | – | – | – |
| 6  | 488 | 771 | 283 | – | – | – |
| 8  | 488 | 992 | 504 | – | – | – |
| 9  | 530 | 685 | 155 | – | – | – |
| 10 | 530 | 771 | 241 | – | – | – |
| 12 | 530 | 992 | 462 | – | – | – |
| 13 | 572 | 685 | 113 | – | – | – |
| 14 | 572 | 771 | 199 | – | – | – |

TABLE 9-6

| | LMO 02736 | | | 41 *Citrobacter freundii* ATCC8090 | 42 *Citrobacter freundii* ATCC8043 | 43 *Proteus vulgaris* IFO3988 | 44 *Lactbacillus bulgarius* IFO13953 | 45 *Lactbacillus helveticus* IFO3809 |
|---|---|---|---|---|---|---|---|---|
| No. | primer: F | primer: R | size | | | | | |
| 1  | 8   | 176 | 168 | – | – | – | – | – |
| 3  | 222 | 591 | 369 | – | – | – | – | – |
| 4  | 488 | 591 | 103 | – | – | – | – | – |
| 5  | 488 | 685 | 197 | – | – | – | – | – |
| 6  | 488 | 771 | 283 | – | – | – | – | – |
| 8  | 488 | 992 | 504 | – | – | – | – | – |
| 9  | 530 | 685 | 155 | – | – | – | – | – |
| 10 | 530 | 771 | 241 | – | – | – | – | – |
| 12 | 530 | 992 | 462 | – | – | – | – | – |
| 13 | 572 | 685 | 113 | – | – | – | – | – |
| 14 | 572 | 771 | 199 | – | – | – | – | – |

| | LMO 02736 | | | 46 *Streptcoccus* sp. IFO3535 | 47 *Streptcoccus sanguis* ATCC10558 | 48 *Streptcoccus mitis* ATCC6249 |
|---|---|---|---|---|---|---|
| No. | primer: F | primer: R | size | | | |
| 1  | 8   | 176 | 168 | – | – | – |
| 3  | 222 | 591 | 369 | – | – | – |
| 4  | 488 | 591 | 103 | – | – | – |
| 5  | 488 | 685 | 197 | – | – | – |
| 6  | 488 | 771 | 283 | – | – | – |
| 8  | 488 | 992 | 504 | – | – | – |
| 9  | 530 | 685 | 155 | – | – | – |
| 10 | 530 | 771 | 241 | – | – | – |
| 12 | 530 | 992 | 462 | – | – | – |
| 13 | 572 | 685 | 113 | – | – | – |
| 14 | 572 | 771 | 199 | – | – | – |

<Designing of LAMP Primers>

LAMP primers were designed based on the primer set F286A/R757B, which targets the lmo0084 gene, and the primer set F530/R771, which targets the lmo2736 gene. For the designing of the primers, LAMP Designer 1.14 (manufactured by OptiGene Limited), which is known support software for designing primers for the LAMP method, was used.

[Designing of LAMP Method Primers Targeting lmo0084]
1. The search region was entered as 1 to 984.
2. The range from F2 to B2 was entered as 150 to 300.
3. Sequences were predicted for the sets of F3/B3, F2/B2, and F1/B1 by the software.
4. Sets were selected such that one of F2 and B2 overlaps with the PCR primer F286A or R757B.
5. Optimization was carried out to select sets in which both F2 and B2 sequences overlap with the primers F286A and R757B.

[Designing of LAMP Method Primers Targeting lmo2736]
1. The search region was entered as 491 to 811.
2. The range from F2 to B2 was entered as 150 to 300.
3. The range from F1 to B1 was entered as 100 to 200.

4. Sequences were predicted for the sets of F3/B3, F2/B2, and F1/B1 by the software.
5. Sets were selected such that F2/B2 overlaps with the PCR primer F530 or R771.
6. The LAMP method was actually carried out with the designed primers, and optimization was carried out mainly for the F2/B2 selected.

The thus obtained LAMP primer sets for specific detection of the *monocytogenes* bacterium are shown below. The lmo0084 LAMP primer set was designed such that it reflects the genetic polymorphism in the serotype 1/2a of the *monocytogenes* bacterium. The lmo2736 LAMP primer sets were designed such that they reflect the genetic polymorphism in the serotype 1/2c of the *monocytogenes* bacterium except for SEQ ID NO:64. As a result of detection tests using the above bacterial strains, all of the primer sets were found to have specificity to the *monocytogenes* bacterium without being influenced by the genetic polymorphisms, as shown below in Table 14-1 to Table 14-3.

TABLE 10 lmo0084 LAMP primer set

| | Sequence (5' → 3') | SEQ ID No. | Setting position |
|---|---|---|---|
| LMO84 F3 | AAATGATTGAAGTCGTACGC | 42 | 104-123 |
| LMO84 B3 | GCAACCTCTTCAATTGGGATA | 43 | 384-404 |
| LMO84 FIP | CTAAAGCTTCTCCGACAAGTTCAATGGATGCAGGGATTAC<br>    ----\*---\*-\*--\*----- | 44 | 191-211 (F1)<br>128-146 (F2) |
| LMO84 BIP | AGAAACCATGTTCAAATTGCAAGAGCTTTCTGGACGGCTATC<br>    \*--------\*-------- | 45 | 220-243 (B1)<br>283-300 (B2) |

SEQ ID NO: 58 shows the sequence of the F2 portion in the 3'-side of FIP, and SEQ ID NO: 59 shows the sequence of the B2 portion in the 3'-side of BIP. In the F2 portion and the B2 portion, \* represents a base showing polymorphism based on comparison among the sequences of SEQ ID NOs: 1 to 25.

TABLE 11 lmo2736 LAMP primer set 1

| | Sequence (5' → 3') | SEQ ID NO. | Setting position |
|---|---|---|---|
| LMO2736-1 F3 | GAACTAGCCTACATTGATGC | 46 | 508-527 |
| LMO2736-1 B3 | TTGAACCGCTTAATAAGTCTG | 47 | 788-808 |
| LMO2736-1 FIP | TTCGTCACGTCACAGGCTATCAGCAACCTTAACCCAAAG<br>    ------\*-----\*------ | 48 | 568-587 (F1)<br>528-546 (F2) |
| LMO2736-1 BIP | GGAGCAAAACTCGACCAATTTTCGTCCAGGAGCGATACCAC<br>    ----\*------------- | 49 | 688-710 (B1)<br>752-769 (B2) |

SEQ ID NO: 60 shows the sequence of the F2 portion in the 3'-side of FIP, and SEQ ID NO: 61 shows the sequence of the 82 portion in the 3'-side of BIP. In the F2 portion and the B2 portion, \* represents a base showing polymorphism based on comparison among the sequences of SEQ ID NOs: 1 to 25.

TABLE 12 lmo2736 LAMP primer set 2

| | Sequence (5' → 3') | SEQ ID NO. | Setting position |
|---|---|---|---|
| LMO2736-2 F3 | CAAGAACTAGCCTACATTGATG | 50 | 505-526 |
| LMO2736-2 B3 | TCTGCATTTAGGAAGGGCATT | 51 | 771-791 |
| LMO2736-2 FIP | TTCGTCACGTCACAGGCTATCAGCAACCTTAACCCAAAGC<br>    ------\*-----\*------- | 52 | 568-587 (F1)<br>528-547 (F2) |
| LMO2736-2 BIP | GGAGCAAAACTCGACCAATTTTC-GTCCAGCAGCGATACCAC<br>    ----\*------------- | 53 | 688-710 (B1)<br>752-769 (B2) |

SEQ ID NO: 62 shows the sequence of the F2 portion in the 3'-side of FIP, and SEQ ID NO: 61 shows the sequence of the B2 portion in the 3'-side of BIP. In the F2 portion and the B2 portion, \* represents a base showing polymorphism based on comparison among the sequences of SEQ ID NOs: 1 to 25.

TABLE 13 lmo2736 LAMP primer set 10

| | Sequence (5' → 3') | SEQ ID NO. | Setting position |
|---|---|---|---|
| LMO2736-10 F3 | GTGGCATTCATTTGCAAGAAC | 54 | 491-511 |
| LMO2736-10 B3 | GAGCTGAACCGCTTAATAAGTC | 55 | 790-811 |
| LMO2736-10 FIP | GAAGTGGATTCGTCACGTCACAGGCTACATTGATGCCAGCAACCTTAAC<br>    *---*--------------*-----* | 56 | 572-595 (F1)<br>516-540 (F2) |
| LMO2736-10 BIP | CTCGACCAATTTTCTTCTCAAAAAATCACCACCAGCGGCTCCG<br>                -----*---------* | 57 | 697-724 (B1)<br>741-755 (B2) |

SEQ ID NO: 63 shows the sequence of the F2 portion in the 3'-side of FIP, and SEQ ID NO: 64 shows the sequence of the B2 portion in the 3'-side of BIP. In the F2 portion and the B2 portion, * represents a base showing polymorphism based on comparison among the sequences of SEQ ID NOs: 1 to 25.

TABLE 14-1

| | | | | | LMO2736 | | | LMO |
| --- | --- | --- | --- | --- | --- | --- | --- | --- |
| | *Listeria monocytogenes* | | | | set 1 | set 2 | set 10 | 0084 |
| No. | Bacterial strain | | | Halo | | | | |
| 1 | *L. monocytogenes* | ½a | GTC 02947 | (+) | + | + | + | + |
| 2 | *L. monocytogenes* | ½b | GTC 02948 | (+) | + | + | + | + |
| 3 | *L. monocytogenes* | ½c | JMC 7672 | (+) | + | + | + | + |
| 4 | *L. monocytogenes* | 3a | JMC 7673 | (+/−) | + | + | + | + |
| 5 | *L. monocytogenes* | 3b | JMC 7677 | (+) | + | + | + | + |
| 6 | *L. monocytogenes* | 3c | JMC 7678 | (+) | + | + | + | + |
| 7 | *L. monocytogenes* | 4a | JMC 7674 | (+) | + | + | + | + |
| 8 | *L. monocytogenes* | 4b | JMC 7675 | (+) | + | + | + | + |
| 9 | *L. monocytogenes* | 4d | JMC 7680 | (+) | + | + | + | + |
| 10 | *L. monocytogenes* | 5 | GTC 02957 | (+) | + | + | + | + |

TABLE 14-2

| | | | LMO2736 | | | |
| --- | --- | --- | --- | --- | --- | --- |
| Bacteria belonging to the genus *Listeria* other than the monocytogenes bacterium | | | set 1 | set 2 | set 10 | LMO0084 |
| No. | Bacterial strain | Halo | | | | |
| 11 | *L. ivanovii* | GTC02961 | (+) | − | − | − | − |
| 12 | *L. ivanovii* subsp. *Ivanovii* | JMC7681 | (+) | − | − | − | − |
| 13 | *L. ivanovii* subsp. *Ivanovii* | GTC01640T | (+) | − | − | − | − |
| 14 | *L. ivanovii* subsp. *Iondoniensis* | GTC01641 | (+) | − | − | − | − |
| 15 | *L. innocua* | GTC16426T | (−) | − | − | − | − |
| 16 | *L. innocua* | GTC02960 | (−) | − | − | − | − |
| 17 | *L. welshimeri* | GTC02963T | (−) | − | − | − | − |
| 18 | *L. seeligeri* | GTC16428T | (+) | − | − | − | − |
| 19 | *L. grayi* | GTC02964T | (−) | − | − | − | − |
| 20 | *L. murrayi* | GTC02964 | (−) | − | − | − | − |
| 21 | *L. marthii* | GTC16430T | (−) | − | − | − | − |
| 22 | *L. rocourtiae* | GTC16429T | (−) | − | − | − | − |

TABLE 14-3

| | | | LMO2736 | | | |
| --- | --- | --- | --- | --- | --- | --- |
| Food-poisoning bacteria other than bacteria belonging to the genus *Listeria* | | | set 1 | set 2 | set 10 | LMO0084 |
| No. | Bacterial strain | | | | | |
| 23 | *Escherichia coli* | ATCC10798 | − | − | − | − |
| 24 | *Salmonella* subsp. *enterica* (I) | JA.107 | − | − | − | − |
| 25 | *Salmonella* subsp. *salamae* (II) | JA.125 | − | − | − | − |
| 26 | *Salmonella* subsp. *arizonae* (IIIa) | JA.76 | − | − | − | − |
| 27 | *Salmonella* subsp. *diarizinae* (IIIb) | JA.129 | − | − | − | − |
| 28 | *Salmonella* subsp. *houtenae* (IV) | JA.n-22 | − | − | − | − |
| 29 | *Salmonella bongori* (V) | JA.94 | − | − | − | − |
| 30 | *Salmonella* subsp. *enterica* Typhimurium | ATCC43971 | − | − | − | − |
| 31 | *Staphylococcus aureus* | ATCC6538P | − | − | − | − |
| 32 | *Staphylococcus aureus* | ATCC25923 | − | − | − | − |
| 33 | *Staphylococcus aureus* | ATCC29213 | − | − | − | − |
| 34 | *Staphylococcus aureus* | JMC2197 | − | − | − | − |
| 35 | *Staphylococcus aureus* | IMCB.IMA2 | − | − | − | − |
| 36 | *Staphylococcus cohnii* | ATCC29974 | − | − | − | − |
| 37 | *Staphylococcus haemolyticus* | ATCC29970 | − | − | − | − |
| 38 | *Staphylococcus hyicus* subsp. | ATCC11249 | − | − | − | − |
| 39 | *Staphylococcus intermedius* | ATCC29663 | − | − | − | − |
| 40 | *Staphylococcus saprophyticus* | ATCC15305 | − | − | − | − |
| 41 | *Citrobacter freundii* | ATCC8090 | − | − | − | − |
| 42 | *Citrobacter freundii* | ATCC8043 | − | − | − | − |
| 43 | *Proteus vulgaris* | IFO3988 | − | − | − | − |
| 44 | *Lactobacillus bulgaricus* | IFO13953 | − | − | − | − |
| 45 | *Lactobacillus helveticus* | IFO3809 | − | − | − | − |
| 46 | *Streptococcus* sp. | IFO3535 | − | − | − | − |
| 47 | *Streptococcus sanguis* | ATCC10558 | − | − | − | − |
| 48 | *Streptococcus mitis* | ATCC6249 | − | − | − | − |

<Designing of Mixed Primers>

For covering polymorphic sequences of more serotypes, mixed primers using mixed bases were designed at the LMO0084 primer designing sites shown above in Table 6.

TABLE 15

| LMO0084 primer | SEQ ID NO. | Sequence | Serotype |
|---|---|---|---|
| F286A | 26 | AGCCGTCCAGAAAGCATCAA | 1/2a, 1/2b, 1/2c, 3a, 3b, 3c, 4b, 4e |
| F286B | 27 | AGCCGCCCAGAAAGTCTCAA | 4a, 4c |
| F286/M | 67 | AGCCGYCCAGAAAGYMTCAA | |
| F281A | 28 | TCGATAGCCGTCCAGAAAGC | 1/2a, 1/2b, 1/2c, 3a, 3b, 3c, 4b, 4e |
| F281B | 29 | TTGATAGCCGCCCAGAAAGT | 4a, 4e |
| F281/M | 68 | TYGATAGCCGYCCAGAAAGY | |
| R757A | 30 | GCTCGTCGGCGATTTCTTTC | 1/2a, 1/2c, 3a, 3c |
| R757B | 31 | GCTCGTCGGCTATTTCTTTC | 1/2b, 3b, 3c, 4a, 4b, 4c |
| R757 | See 9 | GCTCGTCAGCTATTTCTTTC | 4c |
| R757/M | 69 | GCTCGTCRGCKATTTCTTTC | |

Ordinary PCR was carried out with the combinations of F286/M and R757/M, and F281/M and R757/M, to see whether *monocytogenes*-specific amplification can be found therewith. Detection tests were carried out using the *monocytogenes* bacterial strains of the bacterial strain Nos. 1 to 10 shown in Table 5-1, the bacterial strains of the bacterial strain Nos. 11 to 22 belonging to the genus *Listeria* shown in Table 5-2, and the food-poisoning bacteria of the bacterial strain Nos. 23 to 48 (wherein, however, the *Citrobacter freundii* N-326 strain was used instead of the bacterial strain No. 42).

As a result, all *monocytogenes* bacteria showed amplification, and none of the bacterial strains other than the *monocytogenes* bacteria showed amplification (Tables 16-1 to 16-6).

TABLE 16-1

| LM00084 No. | primer: F | primer: R | size | 1 monocytogenes 1/2a GTC02947 | 2 monocytogenes 1/2b GTC02948 | 3 monocytogenes 1/2c JMC7672 | 4 monocytogenes 3a JMC7673 | 5 monocytogenes 3b JMC7677 | 6 monocytogenes 3c JMC7678 |
|---|---|---|---|---|---|---|---|---|---|
| 1 | F286/M | R757/M | 471 | + | + | + | + | + | + |
| 2 | F281/M | R757/M | 476 | + | + | + | + | + | + |

| LM00084 No. | primer: F | primer: R | size | 7 monocytogenes 4a JMC7674 | 8 monocytogenes 4b JMC7675 | 9 monocytogenes 4d JMC7680 | 10 monocytogenes 5 GTC02957 |
|---|---|---|---|---|---|---|---|
| 1 | F286/M | R757/M | 471 | + | + | + | + |
| 2 | F281/M | R757/M | 476 | + | + | + | + |

TABLE 16-2

| LMO0084 No. | primer: F | primer: R | size | 11 ivanovii GTC02961 | 12 ivanovii subsp. Ivanovii JMC7681 | 13 ivanovii subsp. Ivanovii GTC01640T | 14 ivanovii subsp. londoniensisi GTC01641 | 15 innocua GTC16426T | 16 innocua GTC02960 |
|---|---|---|---|---|---|---|---|---|---|
| 1 | F286/M | R757/M | 471 | − | − | − | − | − | − |
| 2 | F281/M | R757/M | 476 | − | − | − | − | − | − |

| LMO0084 No. | primer: F | primer: R | size | 17 welshimeri GTC02963T | 18 seeligeri GTC16428T | 19 grayi GTC02964T | 20 murrayi GTC02964 |
|---|---|---|---|---|---|---|---|
| 1 | F286/M | R757/M | 471 | − | − | − | − |
| 2 | F281/M | R757/M | 476 | − | − | − | − |

TABLE 16-3

| LMO0084 | | | 21 marthii GTC16430T | 22 rocourtiae GTC16429T |
|---|---|---|---|---|
| No. | primer: F | primer: R | size | | |
| 1 | F286/M | R757/M | 471 | – | – |
| 2 | F281/M | R757/M | 476 | – | – |

TABLE 16-4

| LMO0084 | | | | 23 Escherichia coli (K12) | 24 Salmonella subsp. Enterica (I) | 25 Salmonella subsp. Salamae (II) | 26 Salmonella subsp. Arizonae (IIIa) | 27 Salmonella subsp. Diarizinae (IIIb) | 28 Salmonella subsp. Houtenae (IV) |
|---|---|---|---|---|---|---|---|---|---|
| No. | primer: F | primer: R | size | ATCC10798 | JA.107 | JA.125 | JA.76 | JA.129 | JA.n-22 |
| 1 | F286/M | R757/M | 471 | – | – | – | – | – | – |
| 2 | F281/M | R757/M | 476 | – | – | – | – | – | – |

| LMO0084 | | | | 29 Salmonella bongori (V) | 30 Salmonella subsp. Enterica Typhimurium | 31 Staphylococcus aureus | 32 Staphylococcus aureus |
|---|---|---|---|---|---|---|---|
| No. | primer: F | primer: R | size | JA.94 | ATCC43971 | ATCC6538P | ATCC25923 |
| 1 | F286/M | R757/M | 471 | – | – | – | – |
| 2 | F281/M | R757/M | 476 | – | – | – | – |

TABLE 16-5

| LMO0084 | | | | 33 Staphylococcus aureus | 34 Staphylococcus aureus | 35 Staphylococcus aureus | 36 Staphylococcus cohnii | 40 Staphylococcus saprophyticus | 37 Staphylococcus haemolyticus |
|---|---|---|---|---|---|---|---|---|---|
| No. | primer: F | primer: R | size | ATCC29213 | JMC2197 | IMCB.IMA2 | ATCC29974 | ATCC15305 | ATCC29970 |
| 1 | F286/M | R757/M | 471 | – | – | – | – | – | – |
| 2 | F281/M | R757/M | 476 | – | – | – | – | – | – |

| LMO0084 | | | | 38 Staphylococcus hyicus subsp. | 39 Staphylococcus intermedius | 41 Citrobacter freundii | Citrobacter freundii |
|---|---|---|---|---|---|---|---|
| No. | primer: F | primer: R | size | ATCC11249 | ATCC29S63 | ATCC8090 | N-326 |
| 1 | F286/M | R757/M | 471 | – | – | – | – |
| 2 | F281/M | R757/M | 476 | – | – | – | – |

TABLE 16-6

| LMO0084 | | | | 43 Proteus vulgaris | 44 Lactbacillus bulgarius | 45 Lactbacillus helvelicus | 46 Streptcoccus sp. | 47 Streptcoccus sanguis | 48 Streptcoccus mitis |
|---|---|---|---|---|---|---|---|---|---|
| No. | primer: F | primer: R | size | IFO3988 | IFO13953 | IFO3809 | IFO3535 | ATCC10558 | ATCC6249 |
| 1 | F286/M | R757/M | 471 | – | – | – | – | – | – |
| 2 | F281/M | R757/M | 476 | – | – | – | – | – | – |

Similarly, for LMO2736, mixed primers using mixed bases were designed at the lmo2736 primer designing sites shown above in Table 6. The "SEQ ID NO." column shows the SEQ ID NOs. of the lmo2736 gene of the referred serotypes and the SEQ ID NOs. describing the primer sequences.

TABLE 17

| Position Primer abbreviations F/Rare shown in () | Sequence | SEQ ID NO. | Serotype |
|---|---|---|---|
| F 8-27 (F8) | TCGTCATCGCACCTGATTCA | 32 | 1/2a, 1/2c, 3a, 3b, 3c, 4a, 4b, 4c, 4d, 4e |
| F 222-241 | GGCCTCCTACGGTATTCACG | 15 etc | 1/2c, 3a, 3c |
| F 222-241 | GGCCCCCTACGGTATTCACA | 13 | 1/2a |
| F 222-241 | GGCCTCCTACGGTATTCACA | 19, 22 | 4a, 4c |
| F 222-241 | CCCCTCCTACGGTATTCTCG | 14 etc | 1/2b, 3b, 4b, 4d, 4e |
| F 222Mix (F222/M) | GGCCYCCTACGGTATTCWCR | 70 | |
| F 488-507 | CCGGTGGCATTCATTTGCAA | 14 etc | 1/2b, 1/2c, 3b, 3c, 4a, 4b, 4c, 4d, 4e |
| F 488-507 | CCGGCGGTATTCATTTCCAA | 13, 16 | 1/2a, 3a |
| F 488Mix (F488/M) | CCGGYGGYATTCATTTGCAA | 71 | |
| F 530-549 | GCAACCTTAACCCAAAGCTG | 15, 18 | 1/2c, 3c |
| F 530-549 | GCAATCTTAACCCAAAGCTG | 13, 16 | 1/2a, 3a |
| F 530-549 | GCAACCTTAATCCAAACCTG | 14 etc | 1/2b, 3b, 4a, 4b, 4c, 4d, 4e |
| F 530Mix (F530/M) | GCAAYCTTAAYCCAAAGCTG | 72 | |
| F 572-591 | CCTGTGACGTGACGAATCCA | 13 etc | 1/2a, 1/2c, 3a, 3c |
| F 572-591 | CCTGCGACGTCACGAATCCA | 14 etc | 1/2b, 3b, 4b, 4c, 4d, 4e |
| F 572-591 | CCTGTGACGTCACGAATCCA | 19 | 4a |
| F 572Mix (F572/M) | CCTGYGACGTSACGAATCCA | 73 | |
| R 176-157 (R176) | TCCACCTCGGAAGACTCACT | 37 | 1/2a, 1/2b, 1/2c, 3a, 3b, 3c, 4a, 4b, 4c, 4d, 4e |
| R 591-572 | TGGATTCGTCACGTCACAGG | 13 etc | 1/2a, 1/2c, 3a, 3c |
| R 591-572 | TGGATTCGTGACGTCGCAGG | 14 etc | 1/2b, 3b, 4b, 4c, 4d, 4e |
| R 591-572 | TCCATTCGTGACGTCACAGG | 19 | 4a |
| R 591Mix (R591/M) | TGGATTCGTSACGTCRCAGG | 74 | |
| R 685-666 | AGTTCTGCATGGCGTTCTCT | 13 etc | 1/2a, 1/2c, 3a, 3c |
| R 685-666 | AGTTCTGCATCCCCCGCTCT | 14 etc | 1/2b, 3b, 4b, 4d, 43 |
| R 685-666 | AGTTCTGCATGGCGTGCTCT | 19 | 4a |
| R 685-666 | AGTTCTGCATGGCATGCTCT | 22 | 4c |
| R 685Mix (R685/M) | AGTTCTGCATGGCRYKCTCT | 75 | |
| R 771-752 | TAGTCCAGCAGCGATACCAC | 13 etc | 1/2a, 1/2c, 3a, 3c |
| R 771-752 | TAGTCCGGCAGCGATACCAC | 14 etc | 1/2b, 3b, 4a, 4b, 4c, 4d, 4e |
| R 771Mix (R771/M) | TAGTCCRGCAGCGATACCAC | 76 | |
| R 992-973 (R992) | TTGTTTTCGAGTGCAAGGCT | 41 | 1/2a, 1/2b, 1/2c, 3a, 3b, 3c, 4a, 4b, 4c, 4d, 4e |

Ordinary PCR was carried out with the combinations of an F primer and an R primer shown below in Table 18 to see whether *monocytogenes*-specific amplification can be found therewith. Detection tests were carried out using the *mono-* cytogenes bacterial strains of the bacterial strain Nos. 1 to 10 shown in Table 5-1, the bacterial strains of the bacterial strain Nos. 11 to 22 belonging to the genus *Listeria* shown in Table 5-2, and the food-poisoning bacteria of the bacterial strain Nos. 23 to 48 (wherein, however, the *Citrobacter freundii* N-326 strain was used instead of the bacterial strain No. 42).

As a result, all *monocytogenes* bacteria showed amplification, and none of the bacterial strains other than the *monocytogenes* bacteria showed amplification (Tables 19-1 to 19-6).

TABLE 18

|   | LMO2736 F primer | LMO2736 R primer | Amplification size |
|---|---|---|---|
| 1 | F8 | R176 | 168 |
| 2 | F222/M | R591/M | 369 |

TABLE 18-continued

|   | LMO2736 F primer | LMO2736 R primer | Amplification size |
|---|---|---|---|
| 3 | F488/M | R591/M | 103 |
| 4 | F488/M | R685/M | 197 |
| 5 | F488/M | R771/M | 283 |
| 6 | F488/M | R992 | 504 |
| 7 | F530/M | R685/M | 155 |
| 8 | F530/M | R771/M | 241 |
| 9 | F530/M | R992 | 462 |
| 10 | F572/M | R685/M | 133 |
| 11 | F572/M | R771/M | 199 |
| 12 | F572/M | R992 | 420 |

TABLE 19-1

| | LMO2736 | | | 1 monocytogenes 1/2a GTC02947 | 2 monocytogenes 1/2b GTC02948 | 3 monocytogenes 1/2c JMC7672 | 4 monocytogenes 3a JMC7673 | 5 monocytogenes 3b JMC7677 | 6 monocytogenes 3c JMC7678 |
|---|---|---|---|---|---|---|---|---|---|
| No. | primer: F | primer: R | size | | | | | | |
| 1 | F8 | R176 | 168 | + | + | + | + | + | + |
| 2 | F222/M | R591/M | 369 | + | + | + | + | + | + |
| 3 | F488/M | R591/M | 103 | + | + | + | + | + | + |
| 4 | F488/M | R685/M | 197 | + | + | + | + | + | + |
| 5 | F488/M | R771/M | 283 | + | + | + | + | + | + |
| 6 | F488/M | R992 | 504 | + | + | + | + | + | + |
| 7 | F530/M | R685/M | 155 | + | + | + | + | + | + |
| 8 | F530/M | R771/M | 241 | + | + | + | + | + | + |
| 9 | F530/M | R992 | 462 | + | + | + | + | + | + |
| 10 | F572/M | R685/M | 133 | + | + | + | + | + | + |
| 11 | F572/M | R771/M | 199 | + | + | + | + | + | + |
| 12 | F572/M | R992 | 420 | + | + | + | + | + | + |

| | LMO2736 | | | 7 monocytogenes 4a JMC7674 | 8 monocytogenes 4b JMC7675 | 9 monocytogenes 4d JMC7680 | 10 monocytogenes 5 GTC02957 |
|---|---|---|---|---|---|---|---|
| No. | primer: F | primer: R | size | | | | |
| 1 | F8 | R176 | 168 | + | + | + | + |
| 2 | F222/M | R591/M | 369 | + | + | + | + |
| 3 | F488/M | R591/M | 103 | + | + | + | + |
| 4 | F488/M | R685/M | 197 | + | + | + | + |
| 5 | F488/M | R771/M | 283 | + | + | + | + |
| 6 | F488/M | R992 | 504 | + | + | + | + |
| 7 | F530/M | R685/M | 155 | + | + | + | + |
| 8 | F530/M | R771/M | 241 | + | + | + | + |
| 9 | F530/M | R992 | 462 | + | + | + | + |
| 10 | F572/M | R685/M | 133 | + | + | + | + |
| 11 | F572/M | R771/M | 199 | + | + | + | + |
| 12 | F572/M | R992 | 420 | + | + | + | + |

TABLE 19-2

| | LMO2736 | | | 11 ivanovii GTC02961 | 12 ivanovii subsp. Ivanovii JMC7681 | 13 ivanovii subsp. Ivanovii GTC01640T | 14 ivanovii subsp. londoniensisi GTC01641 | 15 innocua GTC16426T | 16 innocua GTC02960 |
|---|---|---|---|---|---|---|---|---|---|
| No. | primer: F | primer: R | size | | | | | | |
| 1 | F8 | R176 | 168 | − | − | − | − | − | − |
| 2 | F222/M | R591/M | 369 | − | − | − | − | − | − |
| 3 | F488/M | R591/M | 103 | − | − | − | − | − | − |
| 4 | F488/M | R685/M | 197 | − | − | − | − | − | − |

TABLE 19-2-continued

| | | | | 17 welshimeri | 18 seeligeri | 19 grayi | 20 murrayi |
|---|---|---|---|---|---|---|---|
| 5 | F488/M | R771/M | 283 | − | − | − | − |
| 6 | F488/M | R992 | 504 | − | − | − | − |
| 7 | F530/M | R685/M | 155 | − | − | − | − |
| 8 | F530/M | R771/M | 241 | − | − | − | − |
| 9 | F530/M | R992 | 462 | − | − | − | − |
| 10 | F572/M | R685/M | 133 | − | − | − | − |
| 11 | F572/M | R77/M | 199 | − | − | − | − |
| 12 | F572/M | R992 | 420 | − | − | − | − |

| | LMO2736 | | | 17 welshimeri | 18 seeligeri | 19 grayi | 20 murrayi |
|---|---|---|---|---|---|---|---|
| No. | primer: F | primer: R | size | GTC02963T | GTC16428T | GTC02964T | GTC02964 |
| 1 | F8 | R176 | 168 | − | − | − | − |
| 2 | F222/M | R591/M | 369 | − | − | − | − |
| 3 | F488/M | R591/M | 103 | − | − | − | − |
| 4 | F488/M | R685/M | 197 | − | − | − | − |
| 5 | F488/M | R771/M | 283 | − | − | − | − |
| 6 | F488/M | R992 | 504 | − | − | − | − |
| 7 | F530/M | R685/M | 155 | − | − | − | − |
| 8 | F530/M | R771/M | 241 | − | − | − | − |
| 9 | F530/M | R992 | 462 | − | − | − | − |
| 10 | F572/M | R685/M | 133 | − | − | − | − |
| 11 | F572/M | R77/M | 199 | − | − | − | − |
| 12 | F572/M | R992 | 420 | − | − | − | − |

TABLE 19-3

| | LMO2736 | | | 21 marthii | 22 rocourtiae |
|---|---|---|---|---|---|
| No. | primer: F | primer: R | size | GTC16430T | GTC16429T |
| 1 | F8 | R176 | 168 | − | − |
| 2 | F222/M | R591/M | 369 | − | − |
| 3 | F488/M | R591/M | 103 | − | − |
| 4 | F488/M | R685/M | 197 | − | − |
| 5 | F488/M | R771/M | 283 | − | − |
| 6 | F488/M | R992 | 504 | − | − |
| 7 | F530/M | R685/M | 155 | − | − |
| 8 | F530/M | R771/M | 241 | − | − |
| 9 | F530/M | R992 | 462 | − | − |
| 10 | F572/M | R685/M | 133 | − | − |
| 11 | F572/M | R771/M | 199 | − | − |
| 12 | F572/M | R992 | 420 | − | − |

TABLE 19-4

| | LMO2736 | | | 23 Escherichia coli (K12) | 24 Salmonella subsp. Enterica (I) | 25 Salmonella subsp. Salamae (II) | 26 Salmonella subsp. Arizonae (IIIa) | 27 Salmonella subsp. Diarizinae (IIIb) | 28 Salmonella subsp. Houtenae (IV) |
|---|---|---|---|---|---|---|---|---|---|
| No. | primer: F | primer: R | size | ATCC10798 | JA.107 | JA.125 | JA.76 | JA.129 | JA.n-22 |
| 1 | F8 | R176 | 168 | − | − | − | − | − | − |
| 2 | F222/M | R591/M | 369 | − | − | − | − | − | − |
| 3 | F488/M | R591/M | 103 | − | − | − | − | − | − |
| 4 | F488/M | R685/M | 197 | − | − | − | − | − | − |
| 5 | F488/M | R771/M | 283 | − | − | − | − | − | − |
| 6 | F488/M | R992 | 504 | − | − | − | − | − | − |
| 7 | F530/M | R685/M | 155 | − | − | − | − | − | − |
| 8 | F530/M | R771/M | 241 | − | − | − | − | − | − |
| 9 | F530/M | R992 | 462 | − | − | − | − | − | − |
| 10 | F572/M | R685/M | 133 | − | − | − | − | − | − |
| 11 | F572/M | R771/M | 199 | − | − | − | − | − | − |
| 12 | F572/M | R992 | 420 | − | − | − | − | − | − |

| | LMO2736 | | | 29 Salmonella bongori (V) | 30 Salmonella subsp. Enterica Typhimurium | 31 Staphylococcus aureus | 32 Staphylococcus aureus |
|---|---|---|---|---|---|---|---|
| No. | primer: F | primer: R | size | JA.94 | ATCC43971 | ATCC6538P | ATCC25923 |
| 1 | F8 | R176 | 168 | − | − | − | − |
| 2 | F222/M | R591/M | 369 | − | − | − | − |
| 3 | F488/M | R591/M | 103 | − | − | − | − |

TABLE 19-4-continued

| No. | primer: F | primer: R | size | | | | |
|---|---|---|---|---|---|---|---|
| 4 | F488/M | R685/M | 197 | − | − | − | − |
| 5 | F488/M | R771/M | 283 | − | − | − | − |
| 6 | F488/M | R992 | 504 | − | − | − | − |
| 7 | F530/M | R685/M | 155 | − | − | − | − |
| 8 | F530/M | R771/M | 241 | − | − | − | − |
| 9 | F530/M | R992 | 462 | − | − | − | − |
| 10 | F572/M | R685/M | 133 | − | − | − | − |
| 11 | F572/M | R771/M | 199 | − | − | − | − |
| 12 | F572/M | R992 | 420 | − | − | − | − |

TABLE 19-5

| | LMO2736 | | | 33 Staphylococcus aureus | 34 Staphylococcus aureus | 35 Staphylococcus aureus | 36 Staphylococcus cohnii | 40 Staphylococcus saprophyticus | 37 Staphylococcus haemolyticus |
|---|---|---|---|---|---|---|---|---|---|
| No. | primer: F | primer: R | size | ATCC29213 | JMC2197 | IMCB.IMA2 | ATCC29974 | ATCC15305 | ATCC29970 |
| 1 | F8 | R176 | 168 | − | − | − | − | − | − |
| 2 | F222/M | R591/M | 369 | − | − | − | − | − | − |
| 3 | F488/M | R591/M | 103 | − | − | − | − | − | − |
| 4 | F488/M | R685/M | 197 | − | − | − | − | − | − |
| 5 | F488/M | R771/M | 283 | − | − | − | − | − | − |
| 6 | F488/M | R992 | 504 | − | − | − | − | − | − |
| 7 | F530/M | R685/M | 155 | − | − | − | − | − | − |
| 8 | F530/M | R771/M | 241 | − | − | − | − | − | − |
| 9 | F530/M | R992 | 462 | − | − | − | − | − | − |
| 10 | F572/M | R685/M | 133 | − | − | − | − | − | − |
| 11 | F572/M | R771/M | 199 | − | − | − | − | − | − |
| 12 | F572/M | R992 | 420 | − | − | − | − | − | − |

| | LMO2736 | | | 38 Staphylococcus hyicus subsp. | 39 Staphylococcus intermedius | 41 Citrobacter freundii | Citrobacter freundii |
|---|---|---|---|---|---|---|---|
| No. | primer: F | primer: R | size | ATCC11249 | ATCC29663 | ATCC8090 | N-326 |
| 1 | F8 | R176 | 168 | − | − | − | − |
| 2 | F222/M | R591/M | 369 | − | − | − | − |
| 3 | F488/M | R591/M | 103 | − | − | − | − |
| 4 | F488/M | R685/M | 197 | − | − | − | − |
| 5 | F488/M | R771/M | 283 | − | − | − | − |
| 6 | F488/M | R992 | 504 | − | − | − | − |
| 7 | F530/M | R685/M | 155 | − | − | − | − |
| 8 | F530/M | R771/M | 241 | − | − | − | − |
| 9 | F530/M | R992 | 462 | − | − | − | − |
| 10 | F572/M | R685/M | 133 | − | − | − | − |
| 11 | F572/M | R771/M | 199 | − | − | − | − |
| 12 | F572/M | R992 | 420 | − | − | − | − |

TABLE 19-6

| | LMO2736 | | | 43 Proteus vulgaris | 44 Lactbacillus bulgarius | 45 Lactbadllus helveticus | 46 Streptcoccus sp. | 47 Streptcoccus sanguis | 48 Streptooccus mitis |
|---|---|---|---|---|---|---|---|---|---|
| No. | primer: F | primer: R | size | IFO3988 | IFO13953 | IFO3809 | IFO3535 | ATCC10558 | ATCC6249 |
| 1 | F8 | R176 | 168 | − | − | − | − | − | − |
| 2 | F222/M | R591/M | 369 | − | − | − | − | − | − |
| 3 | F488/M | R591/M | 103 | − | − | − | − | − | − |
| 4 | F488/M | R685/M | 197 | − | − | − | − | − | − |
| 5 | F488/M | R771/M | 283 | − | − | − | − | − | − |
| 6 | F488/M | R992 | 504 | − | − | − | − | − | − |
| 7 | F530/M | R685/M | 155 | − | − | − | − | − | − |
| 8 | F530/M | R771/M | 241 | − | − | − | − | − | − |
| 9 | F530/M | R992 | 462 | − | − | − | − | − | − |
| 10 | F572/M | R685/M | 133 | − | − | − | − | − | − |
| 11 | F572/M | R771/M | 199 | − | − | − | − | − | − |
| 12 | F572/M | R992 | 420 | − | − | − | − | − | − |

<Designing of TaqMan (Registered Trademark) Probes>

Aiming at construction of a real-time PCR detection system, TaqMan (registered trademark) probes were designed.

[1] LMO0084 Gene

A TaqMan (registered trademark) probe is commonly designed under the following conditions.

A TaqMan (registered trademark) probe is designed as a 20-mer to 30-mer probe (citation from Thermo Fisher).

The amplification target ideally has a length of 70 bp to 200 bp, and should have a length of less than 300 bp (citation from QIAGEN).

However, according to the sets of mixed primers targeting the LMO0084 gene, designed as described above (LMO0084-F286/M and LMO0084-R757/M, and LMO0084-F281/M and LMO0084-R757/M), the length of the amplification target was about 470 bp. Since specificity in the PCR could not be obtained with a length shorter than this, TaqMan (registered trademark) probes were designed within this range. In the amplification target, 20-mer or longer sequences containing a common sequence of not more than two bases in the *monocytogenes* bacterium were present at three locations (Table 20).

TABLE 20

| Probe | Number of bases | Characteristics |
| --- | --- | --- |
| TMP366-389 | 23 mer | Common to all sequences |
| TMP535-558 | 23 mer | TA-type and CC-type exist |
| TMP686-711 | 26 mer | Common to all sequences |

In view of this, the following four kinds of sequences were employed as probe sequences. The oligonucleotide having each sequence was modified with the fluorescent substance FAM (6-carboxyfluorescein) at the 5'-end, and with the quencher substance TAMRA at the 3'-end, to prepare a TaqMan (registered trademark) probe.

```
                        (SEQ ID NO: 77)
0084TMP366-389:    TATTACATTCATAGAATTGACCC (SEQ ID NO: 78)
0084TMP535-558(TA): ATCTGGTGGCGAGAAGCTGAAAA (SEQ ID NO: 79)
0084TMP535-558(CC): ATCTGGTGGCGAGAAGCCGAACA (SEQ ID NO: 80)
0084TMP686-711:    TACCAAGATTCCAAAAAGAAGCCATG
```

The sets of mixed primers shown in Table 15 (LMO0084-F286M and LMO0084-R757M, and LMO0084-F281M and LMO0084-R757M) were used in combination with these TaqMan (registered trademark) probes to carry out detection experiments by real-time PCR using the genomes of test bacterial strains as templates. As the test bacterial strains, the *monocytogenes* bacterial strains of the bacterial strain Nos. 1 to 10 shown in Table 5-1, the bacterial strains of the bacterial strain Nos. 11 to 22 belonging to the genus *Listeria* shown in Table 5-2, and the food-poisoning bacteria of the bacterial strain Nos. 23 to 48 (wherein, however, the *Citrobacter freundii* N-326 strain was used instead of the bacterial strain No. 42) were used.

TABLE 21

| [Composition of the reaction liquid for real-time PCR (total 20 μL)] | |
| --- | --- |
| Template DNA (1 ng/μL) | 1.00 μL |
| TaqMan Fast Advanced Master Mix(2x) | 10.00 μL |
| 100 μM Primer F | 0.08 μL (per primer sequence) |
| 100 μM Primer R | 0.08 μL (per primer sequence) |
| 100 μM TaqMan probe | 0.25 μL |
| Distilled Water | Appropriate volume |

[Reaction Conditions]
Apparatus used: Corbett Research: Roter-Gene6000
50° C. for 2 minutes (holding)→95° C. for 2 minutes (holding)→(95° C. for 3 seconds–64° C. for 15 seconds)×40 cycles Evaluation was carried out based on the presence or absence of the amplification curve. Agarose electrophoresis of the PCR product was also carried out, and the presence or absence of a band, and the band size were investigated.

The results of the real-time PCR tests are shown in Tables 22-1 to 22-3. 0084TMP366-389 and 0084TMP686-711 were capable of specific detection of the *monocytogenes* bacterium by combination with either primer set. 0084TMP535-558(TA) and 0084TMP535-558(CC) were found to be similarly capable of specific detection of the *monocytogenes* bacterium when they were used as a mixed probe. In cases where these are used as a mixture, the reaction liquid composition may be 0.25 μL of 100 μM 0084TMP535-558(TA) and 0.25 μL of 100 μM 0084TMP535-558(CC).

TABLE 22-1

| | | | TaqMan ® probe | | | | | |
| --- | --- | --- | --- | --- | --- | --- | --- | --- |
| | | | TMP366-389 – | TMP535-558 TA | TMP535-558 CC | TMP535-558 Mix (TA/CC) | TMP686-711 – | TMP366-389 – |
| | | | | | primer F | | | |
| | | | F286/M | F286/M | F286/M | F286/M | F286/M | F281/M |
| | | | | | primer: R | | | |
| | LMO 0084 | size | R757/M 471 | R757/M 476 | R757/M 476 | R757/M 476 | R757/M 471 | R757/M 476 |
| 1 | *Listeria monocytogenes* | 1/2a GTC02947 | + | + | – | + | + | + |
| 2 | *Listeria monocytogenes* | 1/2b GTC02948 | + | + | – | + | + | + |

TABLE 22-1-continued

| | | | | | | | | | |
|---|---|---|---|---|---|---|---|---|---|
| 3 | Listeria monocytogenes | 1/2c | JMC7672 | + | + | − | + | + | + |
| 4 | Listeria monocytogenes | 3a | JMC7673 | + | + | − | + | + | + |
| 5 | Listeria monocytogenes | 3b | JMC7677 | + | + | − | + | + | + |
| 6 | Listeria monocytogenes | 3c | JMC7678 | + | + | − | + | + | + |
| 7 | Listeria monocytogenes | 4a | JMC7674 | + | − | + | + | + | + |
| 8 | Listeria monocytogenes | 4b | JMC7675 | + | + | − | + | + | + |
| 9 | Listeria monocytogenes | 4d | JMC7680 | + | + | − | + | + | + |
| 10 | Listeria monocytogenes | 5 | GTC02357 | + | + | − | + | + | + |

| | | | | TaqMan ® probe | | | |
|---|---|---|---|---|---|---|---|
| | | | | TMP535-558 TA | TMP535-558 CC | TMP535-558 Mix (TA/CC) | TMP686-711 − |
| | | | | | | primer F | |
| | | | | F281/M | F281/M | F281/M | F281/M |
| | | | | | | primer H | |
| | | LMO 0084 | size | R757/M 476 | R757/M 476 | R757/M 476 | R757/M 476 |
| 1 | Listeria monocytogenes | 1/2a | GTC02947 | + | − | + | + |
| 2 | Listeria monocytogenes | 1/2b | GTC02948 | + | − | + | + |
| 3 | Listeria monocytogenes | 1/2c | JMC7672 | + | − | + | + |
| 4 | Listeria monocytogenes | 3a | JMC7673 | + | − | + | + |
| 5 | Listeria monocytogenes | 3b | JMC7677 | + | − | + | + |
| 6 | Listeria monocytogenes | 3c | JMC7678 | + | − | + | + |
| 7 | Listeria monocytogenes | 4a | JMC7674 | − | + | + | + |
| 8 | Listeria monocytogenes | 4b | JMC7675 | + | − | + | + |
| 9 | Listeria monocytogenes | 4d | JMC7680 | + | − | + | + |
| 10 | Listeria monocytogenes | 5 | GTC02357 | + | − | + | + |

TABLE 22-2

| | | | TaqMan ® probe | | | | | |
|---|---|---|---|---|---|---|---|---|
| | | | TMP366-389 − | TMP535-558 TA | TMP535-558 CC | TMP535-558 Mix (TA/CC) | TMP686-711 − | TMP366-389 − |
| | | | | | | primer F | | |
| | | | F286/M | F286/M | F286/M | F286/M | F286/M | F281/M |
| | | | | | | primer R | | |
| | LMO 0084 | size | R757/M 471 | R757/M 471 | R757/M 471 | R757/M 471 | R757/M 471 | R757/M 476 |
| 11 | Listeria ivanovii | GTC02961 | − | − | − | − | − | − |
| 12 | Listeria ivanovii subsp. Ivanovii | JMC7681 | − | − | − | − | − | − |
| 13 | Listeria ivanovii subsp. Ivanovii | GTC01640T | − | − | − | − | − | − |
| 14 | Listeria ivanovii subsp. londonionsisi | GTC01641 | − | − | − | − | − | − |
| 15 | Listeria innocua | GTC16426T | − | − | − | − | − | − |
| 16 | Listeria innocua | GTC02960 | − | − | − | − | − | − |
| 17 | Listeria welshimeri | GTC02963T | − | − | − | − | − | − |
| 18 | Listeria seeligeri | GTC16428T | − | − | − | − | − | − |
| 19 | Listeria grayi | GTC02964T | − | − | − | − | − | − |

TABLE 22-2-continued

|    |                    |           |   |   |   |   |   |   |
|----|--------------------|-----------|---|---|---|---|---|---|
| 20 | Listeria murrayi   | GTC02964  | − | − | − | − | − | − |
| 21 | Listeria marthii   | GTC16430T | − | − | − | − | − | − |
| 22 | Listeria rocourtiae| GTC16429T | − | − | − | − | − | − |

|   |   | | TaqMan ® probe | | | |
|---|---|---|---|---|---|---|
|   |   | TMP535-558 TA | TMP535-558 CC | TMP535-558 Mix (TA/CC) | TMP686-711 − |
|   |   | primer F | | | |
|   |   | F281/M | F281/M | F281/M | F281/M |
|   |   | | | primer R | |
| LMO 0084 | size | R757/M 476 | R757/M 476 | R757/M 476 | R757/M 476 |
| 11 Listeria ivanovii | GTC02961 | − | − | − | − |
| 12 Listeria ivanovii subsp. Ivanovii | JMC7681 | − | − | − | − |
| 13 Listeria ivanovii subsp. Ivanovii | GTC01640T | − | − | − | − |
| 14 Listeria ivanovii subsp. londonionsisi | GTC01641 | − | − | − | − |
| 15 Listeria innocua | GTC16426T | − | − | − | − |
| 16 Listeria innocua | GTC02960 | − | − | − | − |
| 17 Listeria welshimeri | GTC02963T | − | − | − | − |
| 18 Listeria seeligeri | GTC16428T | − | − | − | − |
| 19 Listeria grayi | GTC02964T | − | − | − | − |
| 20 Listeria murrayi | GTC02964 | − | − | − | − |
| 21 Listeria marthii | GTC16430T | − | − | − | − |
| 22 Listeria rocourtiae | GTC16429T | − | − | − | − |

TABLE 22-3

|   |   | TaqMan ® probe | | | | | |
|---|---|---|---|---|---|---|---|
|   |   | TMP366-389 − | TMP535-558 TA | TMP535-558 CC | TMP535-558 Mix (TA/CC) | TMP686-711 − | TMP366-389 − |
|   |   | | | | primer F | | |
|   |   | F286/M | F286/M | F28/M | F286/M | F286/M | F281/M |
|   |   | | | primer R | | | |
| LMO 0084 | size | R757/M 471 | R757/M 471 | R757/M 471 | R757/M 471 | R757/M 471 | R757/M 476 |
| 23 Escherichia coli (K12) | ATCC10798 | − | − | − | − | − | − |
| 24 Salmonella subsp. Enterica (I) | JA.107 | − | − | − | − | − | − |
| 25 Salmonella subsp. Salamae (II) | JA.125 | − | − | − | − | − | − |
| 26 Salmonella subsp. Arizonae (IIIa) | JA.76 | − | − | − | − | − | − |
| 27 Salmonella subsp. Diarizinae (IIIb) | JA.129 | − | − | − | − | − | − |
| 28 Salmonella subsp. Houtenae (IV) | JA.n-22 | − | − | − | − | − | − |
| 29 Salmonella bongori (V) | JA.94 | − | − | − | − | − | − |
| 30 Salmonella subsp. EntericaTyphimurium | ATCC43971 | − | − | − | − | − | − |
| 31 Staphylococcus aureus | ATCC6538P | − | − | − | − | − | − |
| 32 Staphylococcus aureus | ATCC25923 | − | − | − | − | − | − |
| 33 Staphylococcus aureus | ATCC29213 | − | − | − | − | − | − |
| 34 Staphylococcus aureus | JMC2197 | − | − | − | − | − | − |
| 35 Staphylococcus aureus | IMCB.IMA2 | − | − | − | − | − | − |
| 36 Staphylococcus cohnii | ATCC29974 | − | − | − | − | − | − |
| 40 Staphylococcus saprophyticus | ATCC15305 | − | − | − | − | − | − |
| 37 Staphylococcus haemolyticus | ATCC29970 | − | − | − | − | − | − |
| 38 Staphylococcus hyicus subsp. | ATCC11249 | − | − | − | − | − | − |

TABLE 22-3-continued

| | | | | | | | |
|---|---|---|---|---|---|---|---|
| 39 | *Staphylococcus intermedius* | ATCC29663 | – | – | – | – | – |
| 41 | *Citrobacter freundii* | ATCC8090 | – | – | – | – | – |
| | *Citrobacter freundii* | N-326 | – | – | – | – | – |
| 43 | *Proteus vulgaris* | IFO3988 | – | – | – | – | – |
| 44 | *Lactbacillus bulgarius* | IFO13953 | – | – | – | – | – |
| 45 | *Lactbacillus helveticus* | IFO3809 | – | – | – | – | – |
| 46 | *Streptcoccus* sp. | IFO3535 | – | – | – | – | – |
| 47 | *Streptcoccus sanguis* | ATCC10558 | – | – | – | – | – |
| 48 | *Streptcoccus mitis* | ATCC6249 | – | – | – | – | – |

| | | | TaqMan ® probe | | | |
|---|---|---|---|---|---|---|
| | | | TMP535-558 TA | TMP535-558 CC | TMP535-558 Mix (TA/CC) | TMP686-711 – |
| | | | primer F | | | |
| | | | F281/M | F281/M | F281/M | F281/M |
| | | | primer R | | | |
| | LMO 0084 | size | R757/M 476 | R757/M 476 | R757/M 476 | R757/M 476 |
| 23 | *Escherichia coli* (K12) | ATCC10798 | – | – | – | – |
| 24 | *Salmonella* subsp. *Enterica* (I) | JA.107 | – | – | – | – |
| 25 | *Salmonella* subsp. *Salamae* (II) | JA.125 | – | – | – | – |
| 26 | *Salmonella* subsp. *Arizonae* (IIIa) | JA.76 | – | – | – | – |
| 27 | *Salmonella* subsp. *Diarizinae* (IIIb) | JA.129 | – | – | – | – |
| 28 | *Salmonella* subsp. *Houtenae* (IV) | JA.n-22 | – | – | – | – |
| 29 | *Salmonella bongori* (V) | JA.94 | – | – | – | – |
| 30 | *Salmonella* subsp. *EntericaTyphimurium* | ATCC43971 | – | – | – | – |
| 31 | *Staphylococcus aureus* | ATCC6538P | – | – | – | – |
| 32 | *Staphylococcus aureus* | ATCC25923 | – | – | – | – |
| 33 | *Staphylococcus aureus* | ATCC29213 | – | – | – | – |
| 34 | *Staphylococcus aureus* | JMC2197 | – | – | – | – |
| 35 | *Staphylococcus aureus* | IMCB.IMA2 | – | – | – | – |
| 36 | *Staphylococcus cohnii* | ATCC29974 | – | – | – | – |
| 40 | *Staphylococcus saprophyticus* | ATCC15305 | – | – | – | – |
| 37 | *Staphylococcus haemolyticus* | ATCC29970 | – | – | – | – |
| 38 | *Staphylococcus hyicus* subsp. | ATCC11249 | – | – | – | – |
| 39 | *Staphylococcus intermedius* | ATCC29663 | – | – | – | – |
| 41 | *Citrobacter freundii* | ATCC8090 | – | – | – | – |
| | *Citrobacter freundii* | N-326 | – | – | – | – |
| 43 | *Proteus vulgaris* | IFO3988 | – | – | – | – |
| 44 | *Lactbacillus bulgarius* | IFO13953 | – | – | – | – |
| 45 | *Lactbacillus helveticus* | IFO3809 | – | – | – | – |
| 46 | *Streptcoccus* sp. | IFO3535 | – | – | – | – |
| 47 | *Streptcoccus sanguis* | ATCC10558 | – | – | – | – |
| 48 | *Streptcoccus mitis* | ATCC6249 | – | – | – | – |

Based on the above results, the following are primer-probe combinations that can be preferably used for detection of the LMO0084 gene by real-time PCR. The number in [ ] represents a SEQ ID NO. in SEQUENCE LISTING.

TABLE 23

| LMO0084 primers | | LMO0084 |
|---|---|---|
| primer: F | primer: R | TaqMan (registered trademark) probe |
| 1 F286/M [67] | R757/M [69] | 0084TMP366-389 [77] |
| 2 F286/M [67] | R757/M [69] | 0084TMP535-558(TA) [78] |
| | | 0084TMP535-558(CC) [79] |
| 3 F286/M [67] | R757/M [69] | 0084TMP686-711 [80] |
| 4 F281/M [68] | R757/M [69] | 0084TMP366-389 [77] |
| 5 F281/M [68] | R757/M [69] | 0084TMP535-558(TA) [78] |
| | | 0084TMP535-558(CC) [79] |
| 6 F281/M [68] | R757/M [69] | 0084TMP686-711 [80] |

[2] LMO2736 Gene

For each of No. 1 and No. 2 among the primer sets shown in Table 18, one TaqMan (registered trademark) probe was designed in the PCR amplification region (Table 24).

Since common sequences were hardly present in the PCR amplification of No. 3 to No. 12, a TaqMan (registered trademark) probe was set at one location in a common sequence in the PCR amplification regions of No. 4 to No. 12 (position 488 to position 992) (Table 24).

TABLE 24

| LMO0084 probe | Number of bases | Characteristics |
|---|---|---|
| TMP70-89 | 20 mer | Common to all sequences |
| TMP372-393 | 20 mer | Common to all sequences |
| TMP619-647 | 29 mer | GG-type and CC-type exist |

The following four kinds of sequences were employed as probe sequences. The oligonucleotide having each sequence was modified with the fluorescent substance FAM (6-carboxyfluorescein) at the 5'-end, and with the quencher substance TAMRA at the 3'-end, to prepare a TaqMan (registered trademark) probe.

2736TMP70-89:           AAAAAAGGCTGGACTAAAGC            (SEQ ID NO: 81)

2736TMP372-393:         ACGTCAAAAAAATCATTATC            (SEQ ID NO: 82)

2736TMP619-647(GG):     GTTTTCGGTGCTCAAAAAGGGGCAAGTCC   (SEQ ID NO: 83)

2736TMP619-647(CC):     GTTTTCGGTGCTCAAAAAGGCGCAACTCC   (SEQ ID NO: 84)

Real-time PCR tests were carried out using the combinations of primers and a probe shown below in Table 24. 2736TMP619-647(GG) and 2736TMP619-647(CC) were used individually or as a mixture to provide a probe. In the table, the number in [ ] represents a SEQ ID NO. in SEQUENCE LISTING. The test bacterial strains used, the composition of the reaction liquid for the real-time PCR, and the reaction conditions were the same as in the above detection tests for the LMO0084 gene. When 2736TMP619-647(SS) was used, the reaction liquid composition was 0.25 µL of 100 µM 2736TMP619-647(GG) and 0.25 µL of 100 µM 2736TMP619-647(CC).

TABLE 25

| LMO2736 primers | | LMO2736 |
|---|---|---|
| primer: F | primer: R | TaqMan (registered trademark) probe |
| 1 F8 [32] | R176 [37] | 2736TMP70-89 [81] |
| 2 F222/M [70] | R591/M [74] | 2736TMP372-393 [82] |
| 3 F530/M [72] | R771/M [76] | 2736TMP619-647(GG) [83] |
| 4 F530/M [72] | R771/M [76] | 2736TMP619-647(CC) [84] |
| 5 F530/M [72] | R771/M [76] | 2736TMP619-647(GG) [83] |
| | | 2736TMP619-647(CC) [84] |

The results are shown in Tables 26-1 to 26-3. The primer-probe sets 1 and 2 in Table 25 were capable of specific detection of the *monocytogenes* bacterium. 2736TMP619-647(GG) and 2736TMP619-647(CC) were capable of specific detection of the *monocytogenes* bacterium when they were used as a mixed probe. Based on the above results, 1, 2, and 5 in Table 25 are primer-probe combinations that can be especially preferably used for detection of the LMO2736 gene by real-time PCR.

TABLE 26-1

| | | | TaqMan ® probe | | | | |
|---|---|---|---|---|---|---|---|
| | | | TMP70-89 | TMP372-393 | TMP619-647 GG | TMP619-647 CC | TMP619-647 Mix (GG/CC) |
| | | | | | primer: F | | |
| | | | F8 | F222/M | F530/M | F530/M | F530/M |
| | | | | | primer: R | | |
| | LMO 2736 | size | R176 168 | R591/M 368 | R771/M 241 | R771/M 241 | R771/M 241 |
| 1 | *Listeria monocytogenes* | 1/2a GTC02947 | + | + | + | − | + |
| 2 | *Listeria monocytogenes* | 1/2b GTC02948 | + | + | + | − | + |
| 3 | *Listeria monocytogenes* | 1/2c JMC7672 | + | + | + | − | + |
| 4 | *Listeria monocytogenes* | 3a JMC7673 | + | + | + | − | + |
| 5 | *Listeria monocytogenes* | 3b JMC7677 | + | + | − | + | + |
| 6 | *Listeria monocytogenes* | 3c JMC7678 | + | + | + | − | + |
| 7 | *Listeria monocytogenes* | 4a JMC7674 | + | + | − | + | + |

TABLE 26-1-continued

| | | | TaqMan ® probe | | | | |
|---|---|---|---|---|---|---|---|
| | | | TMP70-89 | TMP372-393 | TMP619-647 GG primer: F | TMP619-647 CC | TMP619-647 Mix (GG/CC) |
| | | | F8 | F222/M | F530/M primer: R | F530/M | F530/M |
| LMO 2736 | | size | R176 168 | R591/M 368 | R771/M 241 | R771/M 241 | R771/M 241 |
| 8 Listeria monocytogenes | 4b | JMC7675 | + | + | − | + | + |
| 9 Listeria monocytogenes | 4d | JMC7680 | + | + | − | + | + |
| 10 Listeria monocytogenes | 5 | GTC02957 | + | + | − | + | + |

TABLE 26-2

| | | TaqMan ® probe | | | | |
|---|---|---|---|---|---|---|
| | | TMP70-89 | TMP372-393 | TMP619-647 GG primer: F | TMP619-647 CC | TMP619-647 Mix (GG/CC) |
| | | F8 | F222/M | F530/M primer: R | F530/M | F530/M |
| LMO 2736 | size | R176 168 | R591/M 368 | R771/M 241 | R771/M 241 | R771/M 241 |
| 11 Listeria ivanovii | GTC02961 | − | − | − | − | − |
| 12 Listeria ivanovii subsp. Ivanovii | JMC7681 | − | − | − | − | − |
| 13 Listeria ivanovii subsp. Ivanovii | GTC01640T | − | − | − | − | − |
| 14 Listeria ivanovii subsp. londoniensisi | GTC01641 | − | − | − | − | − |
| 15 Listeria innocua | GTC16426T | − | − | − | − | − |
| 16 Listeria innocua | GTC02960 | − | − | − | − | − |
| 17 Listeria welshimeri | GTC02963T | − | − | − | − | − |
| 18 Listeria seeligeri | GTC16428T | − | − | − | − | − |
| 19 Listeria grayi | GTC02964T | − | − | − | − | − |
| 20 Listeria murrayi | GTC02964 | − | − | − | − | − |
| 21 Listeria marthii | GTC16430T | − | − | − | − | − |
| 22 Listeria rocourtiae | GTC16429T | − | − | − | − | − |

TABLE 26-3

| | | TaqMan ® probe | | | | |
|---|---|---|---|---|---|---|
| | | TMP70-89 | TMP372-393 | TMP619-647 GG primer: F | TMP619 647 CC | TMP619-647 Mix (GG/CC) |
| | | F8 | F222/M | F530/M primer: R | F530/M | F530/M |
| LMO 2736 | size | R176 168 | R591/M 368 | R771/M 241 | R771/M 241 | R771/M 241 |
| 23 Escherichia coli (K12) | ATCC10798 | − | − | − | − | − |
| 24 Salmonella subsp. Enterica (I) | JA.107 | − | − | − | − | − |
| 25 Salmonella subsp. Salamae (II) | JA.125 | − | − | − | − | − |
| 26 Salmonella subsp. Arizonae (IIIa) | JA.76 | − | − | − | − | − |

TABLE 26-3-continued

| | | TaqMan ® probe | | | | |
|---|---|---|---|---|---|---|
| | | TMP70-89 | TMP372-393 | TMP619-647 GG primer: F | TMP619 647 CC | TMP619-647 Mix (GG/CC) |
| | | F8 | F222/M | F530/M primer: R | F530/M | F530/M |
| LMO 2736 | size | R176 168 | R591/M 368 | R771/M 241 | R771/M 241 | R771/M 241 |
| 27 Salmonella subsp. Diarizinae (IIIb) | JA.129 | – | – | – | – | – |
| 28 Salmonella subsp. Houtenae (IV) | JA.n-22 | – | – | – | – | – |
| 29 Salmonella bongori (V) | JA.94 | – | – | – | – | – |
| 30 Salmonella subsp. EntericaTyphimurium | ATCC43971 | – | – | – | – | – |
| 31 Staphylococcus aureus | ATCC6538P | – | – | – | – | – |
| 32 Staphylococcus aureus | ATCC25923 | – | – | – | – | – |
| 33 Staphylococcus aureus | ATCC29213 | – | – | – | – | – |
| 34 Staphylococcus aureus | JMC2197 | – | – | – | – | – |
| 35 Staphylococcus aureus | IMCB.IMA2 | – | – | – | – | – |
| 36 Staphylococcus cohnii | ATCC29974 | – | – | – | – | – |
| 40 Staphylococcus saprophyticus | ATCC15305 | – | – | – | – | – |
| 37 Staphylococcus haemolyticus | ATCC29970 | – | – | – | – | – |
| 38 Staphylococcus hyicus subsp. | ATCC11249 | – | – | – | – | – |
| 39 Staphylococcus intermedius | ATCC29663 | – | – | – | – | – |
| 41 Citrobacter freundii | ATCC8090 | – | – | – | – | – |
| Citrobacter freundii | N-326 | – | – | – | – | – |
| 43 Proteus vulgaris | IFO3988 | – | – | – | – | – |
| 44 Lactbacillus bulgarius | IFO13953 | – | – | – | – | – |
| 45 Lactbacillus helveticus | IFO3809 | – | – | – | – | – |
| 46 Streptcoccus sp. | IFO3535 | – | – | – | – | – |
| 47 Streptcoccus sanguis | ATCC10558 | – | – | – | – | - |
| 48 Streptcoccus mitis | ATCC6249 | – | – | – | – | - |

The following is an example of the procedure for preparation of a DNA sample in a case where a *monocytogenes* bacterium test is carried out for food using the present real-time PCR detection system.
(1) To 25 g of food, 225 mL of a bacterial growth selection medium is added, and culture is performed at 30° C. for 24 hours±3 hours. To 10 mL of BHI (Brain-Heart Infusion) medium, 0.1 mL of the resulting culture is added. Alternatively, a single colony on a selection agar medium is picked up, and then inoculated to 10 mL of BHI medium, followed by carrying out culture at 37° C. for 24 hours±3 hours.
(2) Centrifugation (13,000×g, 10 minutes, 20° C.) is carried out to collect bacterial cells from 1 mL of the resulting culture.
(3) DNA is extracted using a DNA extraction kit such as a mericon DNA Bacteria Plus Kit (QIAGEN: 69534).
(4) The DNA concentration is measured.

It was shown that, by this, *monocytogenes* can be specifically detected using a TaqMan (registered trademark) probe designed in the LMO0084 gene or the LMO2736 gene. By using a mixture of a plurality of TaqMan (registered trademark) probes taking polymorphic sequences of these genes into account, various serotypes of the *monocytogenes* bacterium can be comprehensively and specifically detected. The results shown in Table 22-1 and Table 26-1 indicate that, by designing a probe for targeting a polymorphism characteristic to a particular serotype, the *monocytogenes* bacterium can be detected specifically to the serotype, that is, serotype identification is possible. For example, 0084TMP535-558(CC) is a probe capable of specific detection of the serotype 4a. By designing new primers and probes from the regions in these two genes identified by the present inventors as target regions for specific detection of the *monocytogenes* bacterium, or from other regions, and appropriately combining these, identification of serotypes of the *monocytogenes* bacterium is possible.

The invention claimed is:

1. A primer set for detection of *Listeria monocytogenes*, comprising any of the following primer sets for amplification of a partial region of lmo0084 gene or lmo2736 gene of *Listeria monocytogenes*:

(A-1) a set of a forward primer containing in its 3'-side the base sequence of SEQ ID NO:26 or a sequence which is the same as said base sequence except that not more than 4 bases are substituted at a genetic polymorphism site(s) in said base sequence, and a reverse primer containing in its 3'-side the base sequence of SEQ ID NO:30 or a sequence which is the same as said base sequence except that not more than 4 bases are substituted at a genetic polymorphism site(s) in said base sequence;

(A-2) a set of a forward primer containing in its 3'-side the base sequence of SEQ ID NO:26 or a sequence which is the same as said base sequence except that not more than 4 bases are substituted at a genetic polymorphism site(s) in said base sequence, and a reverse primer containing in its 3'-side the base sequence of SEQ ID NO:31 or a sequence which is the same as said base sequence except that not more than 4 bases are substituted at a genetic polymorphism site(s) in said base sequence;

(A-3) a set of a forward primer containing in its 3'-side the base sequence of SEQ ID NO:27 or a sequence which is the same as said base sequence except that not more than 4 bases are substituted at a genetic polymorphism site(s) in said base sequence, and a reverse primer containing in its 3'-side the base sequence of SEQ ID NO:30 or a sequence which is the same as said base sequence except that not more than 4 bases are substituted at a genetic polymorphism site(s) in said base sequence;

(A-4) a set of a forward primer containing in its 3'-side the base sequence of SEQ ID NO:27 or a sequence which is the same as said base sequence except that not more than 4 bases are substituted at a genetic polymorphism site(s) in said base sequence, and a reverse primer containing in its 3'-side the base sequence of SEQ ID NO:31 or a sequence which is the same as said base sequence except that not more than 4 bases are substituted at a genetic polymorphism site(s) in said base sequence;

(A-5) a set of a forward primer containing in its 3'-side the base sequence of SEQ ID NO:28 or a sequence which is the same as said base sequence except that not more than 4 bases are substituted at a genetic polymorphism site(s) in the base sequence, and a reverse primer containing in its 3'-side the base sequence of SEQ ID NO:30 or a sequence which is the same as said base sequence except that not more than 4 bases are substituted at a genetic polymorphism site(s) in said base sequence;

(A-6) a set of a forward primer containing in its 3'-side the base sequence of SEQ ID NO:28 or a sequence which is the same as said base sequence except that not more than 4 bases are substituted at a genetic polymorphism site(s) in said base sequence, and a reverse primer containing in its 3'-side the base sequence of SEQ ID NO:31 or a sequence which is the same as said base sequence except that not more than 4 bases are substituted at a genetic polymorphism site(s) in said base sequence;

(A-7) a set of a forward primer containing in its 3'-side the base sequence of SEQ ID NO:29 or a sequence which is the same as said base sequence except that not more than 4 bases are substituted at a genetic polymorphism site(s) in said base sequence, and a reverse primer containing in its 3'-side the base sequence of SEQ ID NO:30 or a sequence which is the same as said base sequence except that not more than 4 bases are substituted at a genetic polymorphism site(s) in said base sequence;

(A-8) a set of a forward primer containing in its 3'-side the base sequence of SEQ ID NO:29 or a sequence which is the same as said base sequence except that not more than 4 bases are substituted at a genetic polymorphism site(s) in said base sequence, and a reverse primer containing in its 3'-side the base sequence of SEQ ID NO:31 or a sequence which is the same as said base sequence except that not more than 4 bases are substituted at a genetic polymorphism site(s) in said base sequence;

(B-1) a set of a forward primer containing in its 3'-side the base sequence of SEQ ID NO:58 or a sequence which is the same as said base sequence except that not more than 4 bases are substituted at a genetic polymorphism site(s) in said base sequence, and a reverse primer containing in its 3'-side the base sequence of SEQ ID NO:59 or a sequence which is the same as said base sequence except that not more than 4 bases are substituted at a genetic polymorphism site(s) in said base sequence;

(C-1) a set of a forward primer containing in its 3'-side the base sequence of SEQ ID NO:32 or a sequence which is the same as said base sequence except that not more than 4 bases are substituted at a genetic polymorphism site(s) in said base sequence, and a reverse primer containing in its 3'-side the base sequence of SEQ ID NO:37 or a sequence which is the same as said base sequence except that not more than 4 bases are substituted at a genetic polymorphism site(s) in said base sequence;

(D-1) a set of a forward primer containing in its 3'-side the base sequence of SEQ ID NO:33 or a sequence which is the same as said base sequence except that not more than 4 bases are substituted at a genetic polymorphism site(s) in said base sequence, and a reverse primer containing in its 3'-side the base sequence of SEQ ID NO:38 or a sequence which is the same as said base sequence except that not more than 4 bases are substituted at a genetic polymorphism site(s) in said base sequence;

(E-1) a set of a forward primer containing in its 3'-side the base sequence of SEQ ID NO:34 or a sequence which is the same as said base sequence except that not more than 4 bases are substituted at a genetic polymorphism site(s) in the base sequence, and a reverse primer containing in its 3'-side the base sequence of SEQ ID NO:38 or a sequence which is the same as said base sequence except that not more than 4 bases are substituted at a genetic polymorphism site(s) in said base sequence;

(F-1) a set of a forward primer containing in its 3'-side the base sequence of SEQ ID NO:34 or a sequence which is the same as said base sequence except that not more than 4 bases are substituted at a genetic polymorphism site(s) in said base sequence, and a reverse primer containing in its 3'-side the base sequence of SEQ ID NO:39 or a sequence which is the same as said base sequence except that not more than 4 bases are substituted at a genetic polymorphism site(s) in said base sequence;

(G-1) a set of a forward primer containing in its 3'-side the base sequence of SEQ ID NO:34 or a sequence which is the same as said base sequence except that not more than 4 bases are substituted at a genetic polymorphism site(s) in said base sequence, and a reverse primer containing in its 3'-side the base sequence of SEQ ID NO:40 or a sequence which is the same as said base sequence except that not more than 4 bases are substituted at a genetic polymorphism site(s) in said base sequence;

(H-1) a set of a forward primer containing in its 3'-side the base sequence of SEQ ID NO:35 or a sequence which is the same as said base sequence except that not more than 4 bases are substituted at a genetic polymorphism site(s) in the base sequence, and a reverse primer containing in its 3'-side the base sequence of SEQ ID NO:39 or a sequence which is the same as said base sequence except that not more than 4 bases are substituted at a genetic polymorphism site(s) in said base sequence;

(I-1) a set of a forward primer containing in its 3'-side the base sequence of SEQ ID NO:35 or a sequence which is the same as said base sequence except that not more than 4 bases are substituted at a genetic polymorphism site(s) in said base sequence, and a reverse primer containing in its 3'-side the base sequence of SEQ ID NO:40 or a sequence which is the same as said base sequence except that not more than 4 bases are substituted at a genetic polymorphism site(s) in said base sequence;

(I-2) a set of a forward primer containing in its 3'-side the base sequence of SEQ ID NO:60 or a sequence which is the same as said base sequence except that not more than 4 bases are substituted at a genetic polymorphism site(s) in said base sequence, and a reverse primer containing in its 3'-side the base sequence of SEQ ID NO:61 or a sequence which is the same as said base sequence except that not more than 4 bases are substituted at a genetic polymorphism site(s) in said base sequence;

(I-3) a set of a forward primer containing in its 3'-side the base sequence of SEQ ID NO:62 or a sequence which is the same as said base sequence except that not more than 4 bases are substituted at a genetic polymorphism site(s) in said base sequence, and a reverse primer containing in its 3'-side the base sequence of SEQ ID NO:61 or a sequence which is the same as said base sequence except that not more than 4 bases are substituted at a genetic polymorphism site(s) in said base sequence;

(J-1) a set of a forward primer containing in its 3'-side the base sequence of SEQ ID NO:35 or a sequence which is the same as said base sequence except that not more than 4 bases are substituted at a genetic polymorphism site(s) in said base sequence, and a reverse primer containing in its 3'-side the base sequence of SEQ ID NO:41 or a sequence which is the same as said base sequence except that not more than 4 bases are substituted at a genetic polymorphism site(s) in said base sequence;

(K-1) a set of a forward primer containing in its 3'-side the base sequence of SEQ ID NO:36 or a sequence which is the same as said base sequence except that not more than 4 bases are substituted at a genetic polymorphism site(s) in said base sequence, and a reverse primer containing in its 3'-side the base sequence of SEQ ID NO:39 or a sequence which is the same as said base sequence except that not more than 4 bases are substituted at a genetic polymorphism site(s) in the base sequence;

(L-1) a set of a forward primer containing in its 3'-side the base sequence of SEQ ID NO:36 or a sequence which is the same as said base sequence except that not more than 4 bases are substituted at a genetic polymorphism site(s) in said base sequence, and a reverse primer containing in its 3'-side the base sequence of SEQ ID NO:40 or a sequence which is the same as said base sequence except that not more than 4 bases are substituted at a genetic polymorphism site(s) in said base sequence; and (M-1) a set of a forward primer containing in its 3'-side the base sequence of SEQ ID NO:63 or a sequence which is the same as said base sequence except that not more than 4 bases are substituted at a genetic polymorphism site(s) in said base sequence, and a reverse primer containing in its 3'-side the base sequence of SEQ ID NO:64 or a sequence which is the same as said base sequence except that not more than 4 bases are substituted at a genetic polymorphism site(s) in said base sequence wherein the primer set further comprises a probe containing an oligonucleotide portion, wherein the ends of the oligonucleotide portion are modified with a fluorescent substance and a quencher substance, respectively.

2. A method of detecting *Listeria monocytogenes*, comprising a step of amplifying a partial region of lmo0084 gene or lmo2736 gene by a nucleic acid amplification method using the primer set according to claim 1.

3. The method according to claim 2, wherein the amplification of the partial region is carried out by a PCR method or an isothermal amplification method.

4. The method according to claim 3, wherein the isothermal amplification method is a loop-mediated isothermal amplification method.

5. The method according to claim 3, wherein the PCR method is a real-time PCR method.

6. A primer set for detection of *Listeria monocytogenes*, comprising any of the following sets:
- (A-9) a set of a mixed forward primer containing in its 3'-side the base sequence of SEQ ID NO:67, and a mixed reverse primer containing in its 3'-side the base sequence of SEQ ID NO:69;
- (A-10) a set of a mixed forward primer containing in its 3'-side the base sequence of SEQ ID NO:68, and a mixed reverse primer containing in its 3'-side the base sequence of SEQ ID NO:69;
- (D-2) a set of a mixed forward primer containing in its 3'-side the base sequence of SEQ ID NO:70, and a mixed reverse primer containing in its 3'-side the base sequence of SEQ ID NO:74;
- (E-2) a set of a mixed forward primer containing in its 3'-side the base sequence of SEQ ID NO:71, and a mixed reverse primer containing in its 3'-side the base sequence of SEQ ID NO:74;
- (F-2) a set of a mixed forward primer containing in its 3'-side the base sequence of SEQ ID NO:71, and a mixed reverse primer containing in its 3'-side the base sequence of SEQ ID NO:75;
- (G-2) a set of a mixed forward primer containing in its 3'-side the base sequence of SEQ ID NO:71, and a mixed reverse primer containing in its 3'-side the base sequence of SEQ ID NO:76;
- (H-2) a set of a mixed forward primer containing in its 3'-side the base sequence of SEQ ID NO:72, and a mixed reverse primer containing in its 3'-side the base sequence of SEQ ID NO:75;
- (I-4) a set of a mixed forward primer containing in its 3'-side the base sequence of SEQ ID NO:72, and a mixed reverse primer containing in its 3'-side the base sequence of SEQ ID NO:76;
- (J-2) a set of a mixed forward primer containing in its 3'-side the base sequence of SEQ ID NO:72, and a reverse primer containing in its 3'-side the base sequence of SEQ ID NO:41 or a sequence which is the same as said base sequence except that not more than 4 bases are substituted at a genetic polymorphism site(s) in said base sequence;
- (K-3) a set of a mixed forward primer containing in its 3'-side the base sequence of SEQ ID NO:73, and a mixed reverse primer containing in its 3'-side the base sequence of SEQ ID NO:75;
- (L-2) a set of a mixed forward primer containing in its 3'-side the base sequence of SEQ ID NO:73, and a mixed reverse primer containing in its 3'-side the base sequence of SEQ ID NO:76;
- (N-1) a set of a mixed forward primer containing in its 3'-side the base sequence of SEQ ID NO:71, and a reverse primer containing in its 3'-side the base sequence of SEQ ID NO:41 or a sequence which is the same as said base sequence except that not more than 4 bases are substituted at a genetic polymorphism site(s) in said base sequence; and
- (O-1) a set of a mixed forward primer containing in its 3'-side the base sequence of SEQ ID NO:73, and a reverse primer containing in its 3'-side the base sequence of SEQ ID NO:41 or a sequence which is the same as said base sequence except that not more than 4 bases are substituted at a genetic polymorphism site(s) in said base sequence wherein the primer set further comprises a probe containing an oligonucleotide portion, wherein the ends of the oligonucleotide portion are modified with a fluorescent substance and a quencher substance, respectively.

7. A method of detecting *Listeria monocytogenes*, comprising a step of amplifying a partial region of lmo0084 gene or lmo2736 gene by a nucleic acid amplification method using the primer set according to claim 6.

8. A probe for detection of *Listeria monocytogenes* by real-time PCR, comprising an oligonucleotide portion having the base sequence of SEQ ID NO:77, SEQ ID NOs:80 to 82, SEQ ID NO:85, wherein in SEQ ID NO:85 ngaan is tgaaa or cgaac; (or SEQ ID NO:86, wherein in SEQ ID NO:86, ngcaan is ggcaag or cgcaac; and wherein the oligonucleotide portion has ends modified with a fluorescent substance and a quencher substance, respectively.

9. A primer-probe set for real-time PCR for detection of *Listeria monocytogenes*, comprising any of the following sets of primers and a probe:
- [1] a set of a forward primer containing in its 3'-side the base sequence of SEQ ID NO:67, a reverse primer containing in its 3'-side the base sequence of SEQ ID NO:69, and a probe containing an oligonucleotide portion having the base sequence of SEQ ID NO:77 or 80;
- [2] a set of a forward primer containing in its 3'-side the base sequence of SEQ ID NO:67, a reverse primer containing in its 3'-side the base sequence of SEQ ID NO:69, and a mixed probe containing an oligonucleotide portion having the base sequence of SEQ ID NO:85, wherein in SEQ ID NO:85 ngaan is tgaaa or cgaac;
- [3] a set of a forward primer containing in its 3'-side the base sequence of SEQ ID NO:68, a reverse primer containing in its 3'-side the base sequence of SEQ ID NO:69, and a probe containing an oligonucleotide portion having the base sequence of SEQ ID NO:77 or 80;
- [4] a set of a forward primer containing in its 3'-side the base sequence of SEQ ID NO:68, a reverse primer containing in its 3'-side the base sequence of SEQ ID NO:69, and a mixed probe containing an oligonucleotide portion having the base sequence of SEQ ID NO:85, wherein in SEQ ID NO:85 ngaan is tgaaa or cgaac;
- [5] a set of a forward primer containing in its 3'-side the base sequence of SEQ ID NO:32, a reverse primer containing in its 3'-side the base sequence of SEQ ID NO:37, and a probe containing an oligonucleotide portion having the base sequence of SEQ ID NO:81;
- [6] a set of a forward primer containing in its 3'-side the base sequence of SEQ ID NO:70, a reverse primer containing in its 3'-side the base sequence of SEQ ID NO:74, and a probe containing an oligonucleotide portion having the base sequence of SEQ ID NO:82; and

[7] a set of a forward primer containing in its 3'-side the base sequence of SEQ ID NO:72, a reverse primer containing in its 3'-side the base sequence of SEQ ID NO:76, and a mixed probe containing an oligonucleotide portion having the base sequence of SEQ ID NO:86, wherein in SEQ ID NO:86, ngcaan is ggcaag or cgcaac; and wherein each of the oligonucleotide portions of the probes has ends modified with a fluorescent substance and a quencher substance, respectively.

* * * * *

SEQUENCE LISTING

<160> NUMBER OF SEQ ID NOS: 86

<210> SEQ ID NO 1
<211> LENGTH: 983
<212> TYPE: DNA
<213> ORGANISM: Listeria monocytogenes

<400> SEQUENCE: 1
atgaaaaaga gacaattagg aaatgctggc ttagttactt cagagcttgg attcggctgt      60
atggggctaa attatcatcg tggacctgcg aaagatcgaa atgaaatgat tgaagtcgta     120

```
cgcactgcaa tggatgcagg gattacgatg ttcgatacag ctgaagtgta tggaccttat      180
actaacgaag aacttgtcgg agaagctttg gttggcaaaa gaaaccatgt tcaaatcgca      240
acaaaaggtg gttttaaaat taatggttta aataacgaag tcgatagccg tccagaaagc      300
atcaaggccg cggttgaagg ctctctcaaa cggctaaaaa cagattacat tgatttatat      360
tacattcata gaattgaccc ctctatccca attgaagagg ttgccggcac cattcagaat      420
ttaaaacaag aagggaaaat tctacactgg ggactctccg aagccagcgc aaagacaata      480
cgccgtgctc ataaagtaga gccactagct gcggttgaaa gtgagtattc tatctggtgg      540
cgagaagctg aaaaagaagt attcccggtt ttagaagaac ttggcatcgg gcttgtcgca      600
tacagcccac taggtcgtgg ttatttaact ggaaaattag atataaatgc tgacttcaat      660
gcaaacgaca accgtggtgg cttaccaaga ttccaaaaag aagccatgga agccaaccaa      720
gtactactag atttcatgaa agaaatcgcc gacgagcaaa acgtcacaac agcccaactt      780
gccctcgctt ggatacttga ccaaaaacct tggatcgtgc caattcccgg aacaacaaga      840
ccaagcagaa tggaagaaaa tatcgcctcc actgaaattc attttgatga tggagcacga      900
caaaaaatag ctgatgcttt atcgcagatt gaaattgttg gtgatagata ctcagccgcc      960
gaaaataaac gtatcggaaa ata                                              983

<210> SEQ ID NO 2
<211> LENGTH: 983
<212> TYPE: DNA
<213> ORGANISM: Listeria monocytogenes

<400> SEQUENCE: 2
atgaaaaaga gacaattagg aaacactggt ttagtaactt cagagcttgg attcggctgt       60
atgggactca attatcaccg gggacctgcg aaagatagaa agaaatgat tgaagtcgta      120 cgcactgcaa tggatgcagg gattacgatg ttcgatactg ctgaagtgta cggaccttat      180
actaatgaag aacttgtcgg agaagcttta gttggcaaaa gaaaccatgt tcaaattgca      240
acaaaaggtg gttttaaaat taatggttta aataacgaag tcgatagccg tccagaaagc      300
atcaaggccg cggttgaagg ctctctcaaa cggctaaaaa cggattacat tgatttatat      360
tacattcata gaattgaccc ctctatccca attgaagagg ttgccggaac cattcagaat      420
ttaaaacaag aaggaaaaat tctacactgg ggactttccg aagccagcgc aaagacaata      480
cgccgtgctc ataaagtaga gccactagct gctgttgaaa atgagtattc catctggtgg      540
cgagaagctg aaaaagaaat atttccggtt ttagaagaac ttggcatcgg gcttgtcgca      600
tacagcccac taggtcgcgg ttatttaact ggcaaattgg atataaatgc tagcttcaat      660
gaaaacgaca accgcggtgg cttaccaaga ttccaaaaag aagccatgga agccaaccaa      720
gtactactcg atttttatgaa agaaatagcc gacgagcaaa atgtcacaac ggcacaactc      780
gccatcgctt ggatacttga ccaaaaacct tggatcgtgc caattcccgg aacaacaaaa      840
caaagcagaa ttaagaaaaa tatcgcctcc acggacattc gttttgatga cggagcacga      900
caaaaaatag ctgatgcttt atcgcagatt gaaattgttg gtgatagata ctcagcagct      960
gaaaataaac gcatcggaaa gta                                              983

<210> SEQ ID NO 3
<211> LENGTH: 984
<212> TYPE: DNA
<213> ORGANISM: Listeria monocytogenes
```

<400> SEQUENCE: 3

```
atgaaaaaga gacaattagg aaatgctggc ttagttactt cagagcttgg attcggctgt    60
atggggctaa attatcatcg tggacctgcg aaagatcgaa atgaaatgat tgaagtcgta   120
cgcactgcaa tggatgcagg gattacgatg ttcgatacag ctgaagtgta tggaccttat   180
actaacgaag aacttgtcgg agaagctttg gttggcaaaa gaaaccatgt tcaaatcgca   240
acaaaaggtg gttttaaaat taatggttta aataacgaag tcgatagccg tccagaaagc   300
atcaaggccg cggttgaagg ctctctcaaa cggctaaaaa cagattacat tgatttatat   360
tacattcata gaattgaccc ctctatccca attgaagagg ttgccggcac cattcagaat   420
ttaaaacaag aagggaaaat tctacactgg ggactctccg aagccagcgc aaagacaata   480
cgccgtgctc ataaagtaga gccactagct gcggttgaaa gtgagtattc tatctggtgg   540
cgagaagctg aaaaagaagt attcccggtt ttagaagaac ttggcatcgg gcttgtcgca   600
tacagcccac taggtcgtgg ttatttaact ggaaaattag atataaatgc tgacttcaat   660
gcaaacgaca accgtggtgg cttaccaaga ttccaaaaag aagccatgga agccaaccaa   720
gtactactag atttcatgaa agaaatcgcc gacgagcaaa acgtcacaac agcccaactt   780
gccctcgctt ggatacttga ccaaaaacct tggatcgtgc caattcccgg aacaacaaga   840
ccaagcagaa tagaagaaaa tatcgcctcc actgaaattc attttgatga tggagcacga   900
caaaaaatag ctgatgcttt atcgcagatt gaaattgttg gtgatagata ctcagccgcc   960
gaaaataaac gtatcggaaa ataa                                         984
```

<210> SEQ ID NO 4
<211> LENGTH: 984
<212> TYPE: DNA
<213> ORGANISM: Listeria monocytogenes

<400> SEQUENCE: 4

```
atgaaaaaga gacaattagg aaatgctggc ttagttactt cagagcttgg attcggctgt    60
atggggctaa attatcatcg tggacctgcg aaagatcgaa atgaaatgat tgaagtcgta   120
cgcactgcaa tggatgcagg gattacgatg ttcgatacag ctgaagtgta tggaccttat   180
actaacgaag aacttgtcgg agaagctttg gttggcaaaa gaaaccatgt tcaaatcgca   240
acaaaaggtg gttttaaaat taatggttta aataacgaag tcgatagccg tccagaaagc   300
atcaaggccg cggttgaagg ctctctcaaa cggctaaaaa cagattacat tgatttatat   360
tacattcata gaattgaccc ctctatccca attgaagagg ttgccggcac cattcagaat   420
ttaaaacaag aagggaaaat tctacactgg ggactctccg aagccagcgc aaagacaata   480
cgccgtgctc ataaagtaga gccactagct gcggttgaaa gtgagtattc tatctggtgg   540
cgagaagcag aaaaagaagt attcccggtt ttagaagaac ttggcatcgg gcttgtcgca   600
tacagcccac taggtcgtgg ttatttaact ggaaaattag atataaatgc tgacttcaat   660
gcaaacgaca accgtggtgg cttaccaaga ttccaaaaag aagccatgga agccaaccaa   720
gtactactag atttcatgaa agaaatcgcc gacgagcaaa acgtcacaac agcccaactt   780
gccctcgctt ggatacttga ccaaaaacct tggatcgtgc caattcccgg aacaacaaga   840
ccaagcagaa tagaagaaaa tatcgcctcc actgaaattc attttgatga tggagcacga   900
caaaaaatag ctgatgcttt atcgcagatt gaaattgttg gtgatagata ctcagccgcc   960
gaaaataaac gtatcggaaa ataa                                         984
```

```
<210> SEQ ID NO 5
<211> LENGTH: 983
<212> TYPE: DNA
<213> ORGANISM: Listeria monocytogenes

<400> SEQUENCE: 5
atgaaaaaga gacaattagg aaacactggt ttagtaactt cagagcttgg attcggctgt      60
atgggactca attatcaccg gggacctgcg aaagatagaa aagaaatgat tgaagtcgta     120
cgcactgcaa tggatacagg gattacgatg ttcgatactg ctgaagtgta cggaccttat     180
actaatgaag aacttgtcgg agaagcttta gttggcaaaa gaaaccatgt tcaaattgca     240
acaaaaggtg gttttaaaat taatggttta aataacgaag tcgatagccg tccagaaagc     300
atcaaggccg cggttgaagg ctctctcaaa cggctaaaaa cggattacat tgatttatat     360
tacattcata gaattgaccc ctctatccca attgaagagg ttgccggaac cattcagaat     420
ttaaaacaag aaggaaaaat tctacactgg ggactttccg aagccagcgc aaagacaata     480
cgccgtgctc ataaagtaga gccactagct gctgttgaaa atgagtattc catctggtgg     540
cgagaagctg aaaaagaaat atttccggtt ttagaagaac ttggcatcgg gcttgtcgca     600
tacagcccac taggtcgcgg ttatttaact ggcaaattgg atataaatgc tagcttcaat     660
gaaaacgaca accgcggtgg cttaccaaga ttccaaaaag aagccatgga agccaaccaa     720
gtactactcg attttatgaa agaaatagcc gacgagcaaa atgtcacaac ggcacaactc     780
gccatcgctt ggatacttga ccaaaaacct tggatcgtgc caattcccgg aacaacaaaa     840
caaagcagaa ttaaagaaaa tatcgcctcc acggacattc gttttgatga cggagcacga     900
caaaaaatag ctgatgcttt atcgcagatt gaaattgttg gtgatagata ctcagcagct     960
gaaaataaac gcatcggaaa gta                                            983

<210> SEQ ID NO 6
<211> LENGTH: 984
<212> TYPE: DNA
<213> ORGANISM: Listeria monocytogenes

<400> SEQUENCE: 6
atgaaaaaga gacaattagg aaatgctggc ttagttactt cagagcttgg attcggctgt      60
atggggctaa attatcatcg tggacctgcg aaagatcgaa atgaaatgat tgaagtcgta     120
cgcactgcaa tggatgcagg gattacgatg ttcgatacag ctgaagtgta tggaccttat     180
actaacgaag aacttgtcgg agaagctttg gttggcaaaa gaaaccatgt tcaaatcgca     240
acaaaaggtg gttttaaaat taatggttta aataacgaag tcgatagccg tccagaaagc     300
atcaaggccg cggttgaagg ctctctcaaa cggctaaaaa cagattacat tgatttatat     360
tacattcata gaattgaccc ctctatccca attgaagagg ttgccggcac cattcagaat     420
ttaaaacaag aagggaaaat tctacactgg ggactctccg aagccagcgc aaagacaata     480
cgccgtgctc ataaagtaga gccactagct gcggttgaaa gtgagtattc tatctggtgg     540
cgagaagctg aaaaagaagt attcccggtt ttagaagaac ttggcatcgg gcttgtcgca     600
tacagcccac taggtcgtgg ttatttaact ggaaaattag atataaatgc tgacttcaat     660
gcaaacgaca accgtggtgg cttaccaaga ttccaaaaag aagccatgga agccaaccaa     720
gtactactag atttcatgaa agaaatcgcc gacgagcaaa acgtcacaac agcccaactt     780
gccctcgctt ggatacttga ccaaaaacct tggatcgtgc caattcccgg aacaacaaga     840
ccaagcagaa tagaagaaaa tatcgcctcc actgaaattc attttgatga tggagcacga     900
```

| | |
|---|---|
| caaaaaatag ctgatgcttt atcgcagatt gaaattgttg gtgatagata ctcagccgcc | 960 |
| gaaaataaac gtatcggaaa ataa | 984 |

<210> SEQ ID NO 7
<211> LENGTH: 983
<212> TYPE: DNA
<213> ORGANISM: Listeria monocytogenes

<400> SEQUENCE: 7

| | |
|---|---|
| atggataaga gacgattagg cacgactggc ttagttacat cagaactcgg atttggttgt | 60 |
| atggggctca attatcatcg tggtccggcg aaaaatcgga atgaaatgat agaagtcgtt | 120 |
| cgcgccgcaa tggattctgg tattacaatg ttcgataccg ccgaggttta tggtccttat | 180 |
| acaaatgaag aacttgtagg agaagctttg tctagcaaaa gaaatcatgt tcaaattgca | 240 |
| acgaaaggtg gctttaaaat cgatggttta aataacgagg ttgatagccg cccagaaagt | 300 |
| ctcaaagcag cagtggaagg atcgctaaaa cgcttaaaaa ctgattacat tgatctgtat | 360 |
| tacattcata gaattgaccc ttctatccca attgaagaag ttgccggaac tatcaagcag | 420 |
| ttaaagcaag aaggaaaaat tctacactgg gggctttccg aggcaagcgc caaaccatc | 480 |
| cgacgagctc acaaagtaga acgtctagca acagtgaaaa gtgaatactc catctggtgg | 540 |
| cgagaagccg aacaggaaat atttccggct ttagaagaac tcggcatcgg ccttgtcgca | 600 |
| tatagtcctc tcggtcgagg ctatttatct ggtaagcttg atatcaatac taattttact | 660 |
| gaaaatgaca accgcggcgg cctaccaaga ttccaaaaag aagccatgaa agccaaccaa | 720 |
| gtgctgctcg attttatgaa agaaatagcc gacgagcaaa atgtcacaac agctcagctt | 780 |
| gccatcgcct ggattctcga ccaaaaacca tggatcgtcc caattcccgg aacaacaaga | 840 |
| caaagtagaa taaagaaaaa tatcgccgcc actaaaattc attttgatga tgcagcacga | 900 |
| caaaaaatag ctactgcttt atctcagatt gaaatagttg gtgacaggta ctcagctgcc | 960 |
| gaaaataaac gcatcggaaa ata | 983 |

<210> SEQ ID NO 8
<211> LENGTH: 983
<212> TYPE: DNA
<213> ORGANISM: Listeria monocytogenes

<400> SEQUENCE: 8

| | |
|---|---|
| atgaaaaaga gacaattagg aaacactggt ttagtaactt cagagcttgg attcggctgt | 60 |
| atgggactca attatcaccg gggacctgcg aaagatagaa aagaaatgat tgaagtcgta | 120 |
| cgcactgcaa tggatgcagg gattacgatg ttcgatactg ctgaagtgta cggaccttat | 180 |
| actaatgaag aacttgtcgg agaagcttta gttggcaaaa gaaaccatgt tcaaattgca | 240 |
| acaaaaggtg gttttaaaat taatggttta aataacgaag tcgatagccg tccagaaagc | 300 |
| atcaaggccg cggttgaagg ctctctcaaa cggctaaaaa cggattacat tgatttatat | 360 |
| tacattcata gaattgaccc ctctatccca attgaagagg ttgccggaac cattcagaat | 420 |
| ttaaaacaag aaggaaaaat tctacactgg ggactttccg aagccagcgc aaagacaata | 480 |
| cgccgtgctc ataaagtaga gccactagct gctgttgaaa atgagtattc catctggtgg | 540 |
| cgagaagctg aaaagaaat atttccggtt ttagaagaac ttggcatcgg gcttgtcgca | 600 |
| tacagcccac taggtcgcgg ttatttaact ggcaaattgg atataaatgc tagcttcaat | 660 |
| gaaaacgaca accgcggtgg cttaccaaga ttccaaaaag aagccatgga agccaaccaa | 720 |
| gtactactcg attttatgaa agaaatagcc gacgagcaaa atgtcacaac ggcacaactc | 780 |

| gccatcgctt ggatacttga ccaaaaacct tggatcgtgc caattccgg aacaacaaaa | 840 |
| caaagcagaa ttaaagaaaa tatcgcctcc acggacattc gttttgatga cggagcacga | 900 |
| caaaaaatag ctgatgcttt atcgcagatt gaaattgttg gtgatagata ctcagcagct | 960 |
| gaaaataaac gcatcggaaa gta | 983 |

<210> SEQ ID NO 9
<211> LENGTH: 983
<212> TYPE: DNA
<213> ORGANISM: Listeria monocytogenes

<400> SEQUENCE: 9

| atggataaga gacgattggg caagactggc ttagttacat cagaactcgg atttggttgt | 60 |
| atggggctca attatcatcg tggtccggcg aaaaatcgaa atgaaatgat agaagtcgtt | 120 |
| cgcgccgcaa tagattctgg tattacaatg ttcgataccg ccgaggttta cggtccttat | 180 |
| acgaatgaag aacttgtagg agaagctttg tctggcaaaa gaaatcatgt tcaaatcgca | 240 |
| acgaaaggtg gctttaaaat cgatggttta ataacgagg ttgatagccg cccagaaagt | 300 |
| ctcaaagcag cagtggaagg atcgctaaaa cgcttgaaaa ctgattacat tgatttgtat | 360 |
| tacattcata gaattgaccc ttctatccca attgaagaag ttgccggaac tatcaagcag | 420 |
| ttaaagcaag aaggaaaaat tctacactgg gggctttccg aggcaagcgc caaaaccatc | 480 |
| cgacgagctc acaaagtaga acctctagca acagtggaaa gtgaatactc catctggtgg | 540 |
| cgagaagccg aacaggaaat atttccggtt ttagaagaac tcggcatcgg ccttgtcgca | 600 |
| tatagtcctc tcggtcgagg ctatttatct ggcaaacttg atatcaatac taatttcact | 660 |
| gaaaatgaca accgtggcgg gctaccaaga ttccaaaaag aagccatgaa agccaaccaa | 720 |
| gtgctgctcg attttatgaa agaaatagct gacgagcaaa atgtcacaac agcccagctt | 780 |
| gccatcgcct ggattctcga ccaaaaacca tggatcgtcc caattccgg aacaacaaga | 840 |
| caaagtagaa taaagaaaa tatcgccgcc actaaaattc attttgatga tgcagcacga | 900 |
| caaaaaatag ctactgcttt atctcagatt gaaatagttg gtgacaggta ctcagctgcc | 960 |
| gaaaataaac gcatcggaaa ata | 983 |

<210> SEQ ID NO 10
<211> LENGTH: 983
<212> TYPE: DNA
<213> ORGANISM: Listeria monocytogenes

<400> SEQUENCE: 10

| atgaaaaga gacaattagg aaacactggt ttagtaactt cagagcttgg attcggctgt | 60 |
| atgggactca attatcaccg gggacctgcg aaagatagaa agaaaatgat tgaagtcgta | 120 |
| cgcactgcaa tggatgcagg gattacgatg ttcgatactg ctgaagtgta cggaccttat | 180 |
| actaatgaag aacttgtcgg agaagcttta gttggcaaaa gaaaccatgt tcaaattgca | 240 |
| acaaaaggtg gttttaaaat taatggttta ataacgaag tcgatagccg tccagaaagc | 300 |
| atcaaggccg cggttgaagg ctctctcaaa cggctaaaaa cggattacat tgatttatat | 360 |
| tacattcata gaattgaccc ctctatccca attgaagagg ttgccggaac cattcagaat | 420 |
| ttaaaacaag aaggaaaaat tctacactgg ggactttccg aagccagcgc aaagacaata | 480 |
| cgccgtgctc ataaagtaga gccactagct gctgttgaaa gtgagtattc catctggtgg | 540 |
| cgagaagctg aaaagaaat atttccggtt ttagaagaac ttggcatcgg gcttgtcgca | 600 |

| | |
|---|---|
| tacagcccac taggtcgcgg ttatttaact ggcaaattgg atataaatgc tagcttcaat | 660 |
| gaaaacgaca accgcggtgg cttaccaaga ttccaaaaag aagccatgga agccaaccaa | 720 |
| gtactactcg attttatgaa agaaatagcc gacgagcaaa atgtcacaac ggcacaactc | 780 |
| gccatcgctt ggatacttga ccaaaaacct tggatcgtgc caattcccgg aacaacaaaa | 840 |
| caaagcagaa ttaagaaaaa tatcgcctcc acggacattc gttttgatga cggagcacga | 900 |
| caaaaaatag ctgatgcttt atcgcagatt gaaattgttg gtgatagata ctcagcagct | 960 |
| gaaaataaac gcatcggaaa gta | 983 |

```
<210> SEQ ID NO 11
<211> LENGTH: 983
<212> TYPE: DNA
<213> ORGANISM: Listeria monocytogenes

<400> SEQUENCE: 11
```

| | |
|---|---|
| atgaaaaaga gacaattagg aaacactggt ttagtaactt cagagcttgg attcggctgt | 60 |
| atgggactca attatcaccg gggacctgcg aaagatagaa agaaatgat tgaagtcgta | 120 |
| cgcactgcaa tggatgcagg gattacgatg ttcgatactg ctgaagtgta cggaccttat | 180 |
| actaatgaag aacttgtcgg agaagcttta gttggcaaaa gaaaccatgt tcaaattgca | 240 |
| acaaaaggtg gttttaaaat taatggttta aataacgaag tcgatagccg tccagaaagc | 300 |
| atcaaggccg cggttgaagg ctctctcaaa cggctaaaaa cggattacat tgatttatat | 360 |
| tacattcata gaattgaccc ctctatccca attgaagagg ttgccggaac cattcagaat | 420 |
| ttaaaacaag aaggaaaaat tctacactgg ggactttccg aagccagcgc aaagacaata | 480 |
| cgccgtgctc ataaagtaga gccactagct gctgttgaaa atgagtattc catctggtgg | 540 |
| cgagaagctg aaaaagaaat atttccggtt ttagaagaac ttggcatcgg gcttgtcgca | 600 |
| tacagcccac taggtcgcgg ttatttaact ggcaaattgg atataaatgc tagcttcaat | 660 |
| gaaaacgaca accgcggtgg cttaccaaga ttccaaaaag aagccatgga agccaaccaa | 720 |
| gtactactcg attttatgaa agaaatagcc gacgagcaaa atgtcacaac ggcacaactc | 780 |
| gccatcgctt ggatacttga ccaaaaacct tggatcgtgc caattcccgg aacaacaaaa | 840 |
| caaagcagaa ttaagaaaaa tatcgcctcc acggacattc gttttgatga cggagcacga | 900 |
| caaaaaatag ctgatgcttt atcgcagatt gaaattgttg gtgatagata ctcagcagct | 960 |
| gaaaataaac gcatcggaaa gta | 983 |

```
<210> SEQ ID NO 12
<211> LENGTH: 983
<212> TYPE: DNA
<213> ORGANISM: Listeria monocytogenes

<400> SEQUENCE: 12
```

| | |
|---|---|
| atgaaaaaga gacaattagg aaacactggt ttagtaactt cagagcttgg attcggctgt | 60 |
| atgggactca attatcaccg gggacctgcg aaagatagaa agaaatgat tgaagtcgta | 120 |
| cgcactgcaa tggatgcagg gattacgatg ttcgatactg ctgaagtgta cggaccttat | 180 |
| actaatgaag aacttgtcgg agaagcttta gttggcaaaa gaaaccatgt tcaaattgca | 240 |
| acaaaaggtg gttttaaaat taatggttta aataacgaag tcgatagccg tccagaaagc | 300 |
| atcaaggccg cggttgaagg ctctctcaaa cggctaaaaa cggattacat tgatttatat | 360 |
| tacattcata gaattgaccc ctctatccca attgaagagg ttgccggaac cattcagaat | 420 |
| ttaaaacaag aaggaaaaat tctacactgg ggactttccg aagccagcgc aaagacaata | 480 |

```
cgccgtgctc ataaagtaga gccactagct gctgttgaaa atgagtattc catctggtgg     540
cgagaagctg aaaaagaaat atttccggtt ttagaagaac ttggcatcgg gcttgtcgca     600
tacagcccac taggtcgcgg ttatttaact ggcaaattgg atataaatgc tagcttcaat     660
gaaaacgaca accgcggtgg cttaccaaga ttccaaaaag aagccatgga agccaaccaa     720
gtactactcg attttatgaa agaaatagcc gacgagcaaa atgtcacaac ggcacaactc     780
gccatcgctt ggatacttga ccaaaaacct tggatcgtgc caattcccgg aacaacaaaa     840
caaagcagaa ttaaagaaaa tatcgcctcc acggacattc gttttgatga cggagcacga     900
caaaaaatag ctgatgcttt atcgcagatt gaaattgttg gtgatagata ctcagcagct     960
gaaaataaac gcatcggaaa gta                                             983

<210> SEQ ID NO 13
<211> LENGTH: 1134
<212> TYPE: DNA
<213> ORGANISM: Listeria monocytogenes

<400> SEQUENCE: 13
atgaaaatcg tcatcgcacc tgattcattc aaagagagcg ccactgcggt ggaagtagca      60
actgccataa aaaaggctg gactaaagct cgtccagccg atcaaattag ccttgcccct     120
gtttctgacg ggggtgaggg ttttcttact gttttaagtg agtcttccga ggtggaattg     180
ttccaagcag aagtaaccaa cctaaacggt cacaaaataa cggcccccta cggtattcac     240
actagccaag aaactgcgat tatcgagtcc gccaacacga ttggattaga tttaatccca     300
gcggcagacc gcaatccagc ttacgcgagc tctaaaggag tcggtgaact aattttggcg     360
gcactgaatc acaacgtcaa aaaaatcatt atcgggctag gcggaagtgg tacaaacgat     420
ggcggcgctg gctaatcca agctttgggc gttgcactac ttgataaaaa caaacagcct     480
attccgcccg gcggtattca tttgcaagag ctagcctata ttgatgccag caatcttaac     540
ccaaagctga aaacattca attccaaata gcctgtgacg tgacgaatcc acttcttgga     600
gaaaacggtg ctacatttgt tttcggtgct caaaaagggg caagtcccga catgctcgtt     660
aaactagaga acgccatgca gaactacgga gcaaaactcg accaattttc ttctcaaaaa     720
atcaccacaa aaaaggagc tggagccgct ggtggtatcg ctgctggact aatgaccttc     780
ctaaatgcag acttattaag cggttcaact cttgttatgg aactttctaa tatgaaagat     840
aaaatgaaag acgccgatat tgttattgtt ggtgaaggac gaatggacaa gcaatcgatg     900
atggggaaaa ttcctgttca aatcgctcaa gaagctaaaa acaaggttg cttcgttctg     960 gctattgtcg gcagccttgc actcgaaaac aacctagccc aacagcacgg catcgatgct    1020
tttttcccaa acatccctga ataacagat ttacccactc tttttgaaaa tacgacgaaa    1080
aacctcgaac gtacggcgga aaacatcgcc aaactaactt taattggcaa ataa         1134

<210> SEQ ID NO 14
<211> LENGTH: 1134
<212> TYPE: DNA
<213> ORGANISM: Listeria monocytogenes

<400> SEQUENCE: 14
atgaaaatcg tcatcgcacc tgattcattc aaagagagcg ccactgctgt tgaagtagca      60
aatgctataa aaaaggctg gactaaagca cgtccagccg atcaaattag ccttgcccct     120
gtttctgacg ggggtgaggg ttttcttact gttttaagtg agtcttccga ggtggaattg     180
```

| | |
|---|---|
| tttcaagcag aagtaaccaa cctaaatggt cacaaaataa cggcctccta cggtattctc | 240 |
| gctagccaag aaactgcaat tatcgagtcc gctaacacga ttggattaga tttaatccca | 300 |
| gccgtagacc gcaatccagc ttacgcgagc tctaaaggcg tcggtgaact tatttttggcg | 360 |
| gcactgaatc acaacgtcaa aaaaatcatt atcggccttg gtggaagtgg cacaaacgat | 420 |
| ggcggcgctg ggctaatcca agctttgggc gttgcactac ttgataaaaa caaacagcct | 480 |
| attccgcccg gtggcattca tttgcaagaa ctagcttaca ttgatgccag caaccttaat | 540 |
| ccaaagctga aaacattca attccaaata gcctgcgacg tcacgaatcc acttcttgga | 600 |
| gaaaacggcg ctaccttcgt tttcggtgct caaaaaggcg caactcccga atgctcgtt | 660 |
| caactagagc gcgccatgca gaactacgga gcaaaactcg atcaattttc atctcaaaaa | 720 |
| atcactacaa aaaaggagc cggagccgct ggtggtatcg ctgccggact aatgactttc | 780 |
| ctaaatgcat acgtgttaag cggttcagct ctagttatgg aactttctaa tatgaaggat | 840 |
| aaaatgaaag atgcggatat cgttattgtt ggtgaaggac gaatggacaa gcaatcgatg | 900 |
| atggggaaaa tccctgttca aattgctcaa gaagctaaaa acaaggttg tttcgtccta | 960 |
| gcaatcgtcg gtagccttgc actcgaaaac aatatcgccc aacaacacgg tatcgatgcg | 1020 |
| tttttcccaa acatcccaga ataacagat ttacccactc ttttcgaaaa tacaacaaag | 1080 |
| aacctcgaac gcacggcgga aaacattgcc aaactaactt taattggcaa ataa | 1134 |

<210> SEQ ID NO 15
<211> LENGTH: 1134
<212> TYPE: DNA
<213> ORGANISM: Listeria monocytogenes

<400> SEQUENCE: 15

| | |
|---|---|
| atgaaaatcg tcatcgcacc tgattcattc aaagaaagcg ccactgcggt ggaagtagca | 60 |
| actgccatta aaaaggctg gactaaagct cgtccagccg atcaaataag ccttgcccct | 120 |
| gtttctgacg ggggtgaggg ttttcttact gttttaagtg agtcttccga ggtggaattg | 180 |
| ttccaagcag aagtaaccaa cttaaacggt cacaaaataa tggcctccta cggtattcac | 240 |
| gcccgccaag aaactgcgat tatcgagtcc gccaacacga ttggattaga tttaatccca | 300 |
| gcggcagacc gtaatccagc ccatgcaagc tctgctggcg tcggtgaact aattttggca | 360 |
| tcactggatc acaacgtcaa aaaaatcatt atcggccttg gtggaagtgg cacaaacgat | 420 |
| ggcggcgctg gactaatcca agctttgggc gttgcactac ttgataaaaa caaacagcct | 480 |
| attccgcccg gtggcattca tttgcaagaa ctagcctaca ttgatgccag caaccttaac | 540 |
| ccaaagctga aaacattca attccaaata gcctgtgacg tgacgaatcc acttcttgga | 600 |
| gaaaacggtg ctacatttgt tttcggtgct caaaaagggg caagtcccga catgctcgtt | 660 |
| aaactagaga cgccatgca gaactacgga gcaaaactcg accaattttc ttctcaaaaa | 720 |
| atcaccacaa aaaaggagc tggagccgct ggtggtatcg ctgctggact aatgaccttc | 780 |
| ctaaatgcag acttattaag cggttcaact cttgttatgg aactttctaa tatgaaagat | 840 |
| aaaatgaaag acgccgatat tgttattgtt ggtgaaggac gaatggacaa gcaatcgatg | 900 |
| atggggaaaa ttcctgttca aatcgctcaa gaagctaaaa acaaggttg cttcgttctg | 960 |
| gctattgtcg gcagccttgc actcgaaaac aacctagccc agcagcacgg catcgatgct | 1020 |
| tttttcccaa acatccctga ataacagat ttacccactc ttttgaaaa tacgacgaaa | 1080 |
| aacctcgaac gtacggcgga aaacatcgcc aaactaactt taattggcaa ataa | 1134 |

<210> SEQ ID NO 16
<211> LENGTH: 1134
<212> TYPE: DNA
<213> ORGANISM: Listeria monocytogenes

<400> SEQUENCE: 16

| | | | | | |
|---|---|---|---|---|---|
| atgaaaatcg | tcatcgcacc | tgattcattc | aaagaaagcg | ccactgcggt | ggaagtagca | 60 |
| actgccatta | aaaaaggctg | gactaaagct | cgtccagccg | atcaaataag | ccttgcccct | 120 |
| gtttctgacg | ggggtgaggg | ttttcttact | gttttaagtg | agtcttccga | ggtgaattg | 180 |
| ttccaagcag | aagtaaccaa | cttaaacggt | cacaaaataa | tggcctccta | cggtattcac | 240 |
| gcccgccaag | aaactgcgat | tatcgagtcc | gccaacacga | ttggattaga | tttaatccca | 300 |
| gcggcagacc | gcaatccagc | ttacgcgagc | tctaaaggag | tcggtgaact | aattttggca | 360 |
| tcactggatc | acaacgtcaa | aaaaatcatt | atcggccttg | gtggaagtgg | cacaaacgat | 420 |
| ggcggcgctg | gactaatcca | agctttgggc | gttgcgctac | ttgataaaaa | caaacagcct | 480 |
| attctgcccg | gcggtattca | tttgcaagag | ctagcctata | ttgatgccag | caatcttaac | 540 |
| ccaaagctga | aaacattca | attccaaata | gcctgtgacg | tgacgaatcc | acttcttgga | 600 |
| gaaaacggtg | ctacatttgt | tttcggtgct | caaaaagggg | caagtcccga | catgctcgtt | 660 |
| aaactagaga | acgccatgca | gaactacgga | gcaaaactcg | accaattttc | ttctcaaaaa | 720 |
| atcaccacaa | aaaaggagc | tggagccgct | ggtggtatcg | ctgctggact | aatgaccttc | 780 |
| ctaaatgcag | acttattaag | cggttcaact | cttgttatgg | aactttctaa | tatgaaagat | 840 |
| aaaatgaaag | acgccgatat | tgttattgtt | ggtgaaggac | gaatggacaa | gcaatcgatg | 900 |
| atggggaaaa | ttcctgttca | aatcgctcaa | gaagctaaaa | acaaggttg | cttcgttctg | 960 |
| gctattgtcg | gcagccttgc | actcgaaaac | aacctagccc | agcagcacgg | catcgatgct | 1020 |
| tttttcccaa | acatccctga | aataacagat | ttacccactc | tttttgaaaa | tacgacgaaa | 1080 |
| aacctcgaac | gtacggcgga | aaacatcgcc | aaactaactt | taattggcaa | ataa | 1134 |

<210> SEQ ID NO 17
<211> LENGTH: 1134
<212> TYPE: DNA
<213> ORGANISM: Listeria monocytogenes

<400> SEQUENCE: 17

| | | | | | |
|---|---|---|---|---|---|
| atgaaaatcg | tcatcgcacc | tgattcattc | aaagagagcg | ccactgctgt | tgaagtagca | 60 |
| aatgctataa | aaaaggctg | gactaaagca | cgtccagccg | atcaaattag | ccttgcccct | 120 |
| gtttctgacg | ggggtgaggg | ttttcttact | gttttaagtg | agtcttccga | ggtgaatta | 180 |
| tttcaagcag | aagtaaccaa | cctaaatggt | cacaaaataa | cggcctccta | cggtattctc | 240 |
| gctagccaag | aaactgcgat | tatcgagtcc | gccaacacga | ttggattaga | tttaatccca | 300 |
| gccgtagacc | gtaatccagc | ttacgcgagc | tctaaaggcg | tcggtgaact | aattttggcg | 360 |
| gcactgaatc | acaacgtcaa | aaaaatcatt | atcggccttg | gtggaagtgg | cacaaacgat | 420 |
| ggcggcgctg | ggctaatcca | agctttgggc | gttgcactac | ttgataaaaa | caaacagcct | 480 |
| attccgcccg | gtggcattca | tttgcaagaa | ctagcttaca | ttgatgccag | caaccttaat | 540 |
| ccaaagctga | aaacattca | attccaaata | gcctgcgacg | tcacgaatcc | acttcttgga | 600 |
| gaaaacggcg | ctaccttcgt | tttcggtgct | caaaaaggcg | caactcccga | atgctcgtt | 660 |
| caactagagc | gcgccatgca | gaactacgga | gcaaaactcg | atcaatttc | atctcaaaaa | 720 |
| atcactacaa | aaaaggagc | cggagccgct | ggtggtatcg | ctgccggact | aatgactttc | 780 |

| | |
|---|---|
| ctaaatgcag acgtgttaag cggttcagct ctagttatgg aactttctaa tatgaaggat | 840 |
| aaaatgaaag atgcggatat cgttattgtt ggtgaaggac gaatggacaa gcaatcgatg | 900 |
| atggggaaaa tccctgttca aattgctcaa gaagctaaaa acaaggttg tttcgtccta | 960 |
| gcaatcgtcg gtagccttgc actcgaaaac aatatcgccc aacaacacgg tatcgatgcg | 1020 |
| tttttcccaa acatcccaga aataacagat ttacccactc tttttcgaaaa tacaacaaag | 1080 |
| aacctcgaac gcacggcgga aaacattgcc aaactaactt taattggcaa ataa | 1134 |

<210> SEQ ID NO 18
<211> LENGTH: 1134
<212> TYPE: DNA
<213> ORGANISM: Listeria monocytogenes

<400> SEQUENCE: 18

| | |
|---|---|
| atgaaaatcg tcatcgcacc tgattcattc aaagaaagcg ccactgcggt ggaagtagca | 60 |
| actgccatta aaaaggctg gactaaagct cgtccagccg atcaaataag ccttgcccct | 120 |
| gtttctgacg ggggtgaggg ttttcttact gttttaagtg agtcttccga ggtggaattg | 180 |
| ttccaagcag aagtaaccaa cttaaacggt cacaaaataa tggcctccta cggtattcac | 240 |
| gcccgccaag aaactgcgat tatcgagtcc gccaacacga ttggattaga tttaatccca | 300 |
| gcggcagacc gtaatccagc ccatgcaagc tctgctggcg tcggtgaact aattttggca | 360 |
| tcactggatc acaacgtcaa aaaaatcatt atcggccttg gtggaagtgg cacaaacgat | 420 |
| ggcggcgctg gactaatcca agctttgggc gttgcactac ttgataaaaa caaacagcct | 480 |
| attccgcccg gtggcattca tttgcaagaa ctagcctaca ttgatgccag caaccttaac | 540 |
| ccaaagctga aaacattca attccaaata gcctgtgacg tgacgaatcc acttcttgga | 600 |
| gaaaacggtg ctacatttgt tttcggtgct caaaaagggg caagtcccga catgctcgtt | 660 |
| aaactagaga acgccatgca gaactacgga gcaaaactcg accaattttc ttctcaaaaa | 720 |
| atcaccacaa aaaaggagc tggagccgct ggtggtatcg ctgctggact aatgaccttc | 780 |
| ctaaatgcag acttattaag cggttcaact cttgttatgg aactttctaa tatgaaagat | 840 |
| aaaatgaaag acgccgatat tgttattgtt ggtgaaggac gaatggacaa gcaatcgatg | 900 |
| atggggaaaa tccctgttca aatcgctcaa gaagctaaaa acaaggttg cttcgttctg | 960 |
| gctattgtcg gcagccttgc actcgaaaac aacctagccc agcagcacgg catcgatgct | 1020 |
| tttttcccaa acatccctga aataacagat ttacccactc ttttttgaaaa tacgacgaaa | 1080 |
| aacctcgaac gtacggcgga aaacatcgcc aaactaactt taattggcaa ataa | 1134 |

<210> SEQ ID NO 19
<211> LENGTH: 1134
<212> TYPE: DNA
<213> ORGANISM: Listeria monocytogenes

<400> SEQUENCE: 19

| | |
|---|---|
| atgaaaatcg tcatcgcacc tgattcattc aaagagagcg ccactgcggt ggaagtagca | 60 |
| actgccataa aaaaggctg gactaaagct cgtccagccg atcaaattag ccttgcccct | 120 |
| gtttctgacg ggggtgaggg ttttcttact gttttaagtg agtcttccga ggtggaattg | 180 |
| ttccaagcag aagtaaccaa cctaaacggt cacaaaataa cggcctccta cggtattcac | 240 |
| actagccaag aaactgcgat tatcgagtcc gccaacacga ttggattaga tttaatccca | 300 |
| gcggcagacc gcaatccagc ttacgcgagc tctaaaggcg tcggtgaact aattttggcg | 360 |
| gcactgaatc acaacgtcaa aaaaatcatt atcgggctag gcggaagtgg tacaaacgat | 420 |

```
ggcggcgctg ggctaatcca agctttgggc gttgcactac ttgataaaaa caaacagcct      480
attccgcccg gtggcattca tttgcaagaa ctagcctaca ttgatgccag caaccttaat      540
ccaaagctga aaacattca attccaaata gcctgtgacg tcacgaatcc acttcttgga      600
gaaaacggcg ctaccttcgt tttcggtgct caaaaaggcg caactcccga aatgctcgtt      660
caactagagc acgccatgca gaactacggg gcaaaacttg atcaattttc atctcaaaaa      720
atcactacaa aaaaggagc cggagccgct ggtggtatcg ctgccggact aatgactttc      780
ctaaatgcag acgtattaag cggttcagct cttgttatgg aactttctaa tatgaaggat      840
aaaatgaaag atgcggatat cgtcattgtt ggcgaagggc gaatggacaa gcaatcgatg      900
atggggaaaa tccctgttca aatcgctcaa gaagctaaaa acaaggttg tttcgtccta      960 gcaatcgtcg gtagccttgc actcgaaaac aatatcgccc aacaacacgg tatcgatgcg     1020
ttcttcccaa acatcccaga aataacagat ttacccactc ttttcgaaaa tacaacaaag     1080
aacctcgaac gcacggcgga aaacattgcc aaattaactt taattggcaa ataa           1134
```

<210> SEQ ID NO 20
<211> LENGTH: 1134
<212> TYPE: DNA
<213> ORGANISM: Listeria monocytogenes

<400> SEQUENCE: 20

```
atgaaaatcg tcatcgcacc tgattcattc aaagagagcg ccactgctgt tgaagtagca       60
aatgctataa aaaaggctg gactaaagca cgtccagccg atcaaattag ccttgccccct     120 gtttctgacg ggggtgaggg ttttcttact gttttaagtg agtcttccga ggtggaattg     180
tttcaagcag aagtaaccaa cctaaatggt cacaaaataa cggcctccta cggtattctc     240
gctagccaag aaactgcaat tatcgagtcc gctaacacga ttggattaga tttaatccca     300
gccgtagacc gcaatccagc ttacgcgagc tctaaaggcg tcggtgaact aattttggcg     360
gcactgaatc acaacgtcaa aaaaatcatt atcggccttg gtggaagtgg cacaaacgat     420
ggcggcgctg ggctaatcca agctttgggc gttgcactac ttgataaaaa caaacagcct     480
attccgcccg gtggcattca tttgcaagaa ctagcttaca ttgatgccag caaccttaat     540
ccaaagctga aaacattca attccaaata gcctgcgacg tcacgaatcc acttcttgga     600
gaaaacggcg ctaccttcgt tttcggtgct caaaaaggcg caactcccga aatgctcgtt     660
caactagagc gcgccatgca gaactacgga gcaaaactcg atcaattttc atctcaaaaa     720
atcactacaa aaaaggagc cggagccgct ggtggtatcg ctgccggact aatgactttc     780
ctaaatgcag acgtgttaag cggttcagct ctagttatgg aactttctaa tatgaaggat     840
aaaatgaaag atgcggatat cgttattgtt ggtgaaggac gaatggacaa gcaatcgatg     900
atggggaaaa tccctgttca aattgctcaa gaagctaaaa acaaggttg tttcgtccta     960 gcaatcgtcg gtagccttgc actcgaaaac aatatcgccc aacaacacgg tatcgatgcg    1020 ttttcccaa acatcccaga aataacagat ttacccactc ttttcgaaaa tacaacaaag    1080
aacctcgaac gcacggcgga aaacattgcc aaactaactt taattggcaa ataa          1134
```

<210> SEQ ID NO 21
<211> LENGTH: 1134
<212> TYPE: DNA
<213> ORGANISM: Listeria monocytogenes

<400> SEQUENCE: 21

```
atgaaaatcg tcatcgcacc tgattcattc aaagagagcg ccactgctgt tgaagtagca      60
aatgccataa aaaaggctg gactaaagca cgtccagccg atcaaattag ccttgccccct    120 gtttctgacg ggggtgaggg ttttcttact gttttaagtg agtcttccga ggtggaattg    180
tttcaagcag aagtaaccaa cctaaatggt cacaaaataa cggcctccta cggtattctc    240
gctagccaag aaactgcaat tatcgagtcc gctaacacga ttggattaga tttaatccca    300
gccgtagacc gcaatccagc ttacgcgagc tctaaaggcg tcggtgaact tattttggcg    360
gcactgaatc acaacgtcaa aaaatcatt atcggccttg gtggaagtgg cacaaacgat     420
ggcggcgctg gctaatcca agctttgggc gttgcactac ttgataaaaa caaacagcct     480
attccgcccg gtggcattca tttgcaagaa ctagcttaca ttgatgccag caaccttaat    540
ccaaagctga aaacattca attccaaata gcctgcgacg tcacgaatcc acttcttgga     600
gaaaacggcg ctaccttcgt tttcggtgct caaaaaggcg caactcccga aatgctcgtt    660
caactagagc gcgccatgca gaactacgga gcaaaactcg atcaattttc atctcaaaaa    720
atcactacaa aaaaggagc cggagccgct ggtggtatcg ctgccggact aatgactttc     780
ctaaatgcag acgtgttaag cggttcagct ctagttatgg aactttctaa tatgaaggat    840
aaaatgaaag atgcggatat cgttattgtt ggtgaaggac gaatgggaca gcaatcgatg    900
atggggaaaa tccctgttca aattgctcaa gaagctaaaa acaaggttg tttcgtccta     960 gcaatcgtcg gtagccttgc actcgaaaac aatatcgccc aacaacacgg tatcgatgcg  1020 ttttcccaa acatcccaga aataacagat ttacccactc ttttcgaaaa tacaacaaag   1080
aacctcgaac gcacggcgga aaacattgcc aaactaactt taattggcaa ataa         1134

<210> SEQ ID NO 22
<211> LENGTH: 1134
<212> TYPE: DNA
<213> ORGANISM: Listeria monocytogenes

<400> SEQUENCE: 22
atgaaaatcg tcatcgcacc tgattcattc aaagagagcg ccactgcagt ggaagtagca      60
actgccataa aaaaggctg gactaaagct cgtccagccg atcaaattag ccttgccccct   120 gtttctgacg ggggtgaggg ttttcttact gttttaagtg agtcttccga ggtggaattg    180
ttccaagcag aagtaaccaa cctaaacggt cacaaaataa cggcctccta cggtattcac    240
actagccaag aaactgcgat tatcgagtcc gccaacacga ttggattaga tttaatccca    300
gcagtagacc gcaatccagc ttacgcgagc tctaaaggcg tcggtgaact aattttggcg    360
gcactgaatc acaacgtcaa aaaatcatt atcgggctag cggaagtgg tacaaacgat     420 ggcggcgctg gctaatcca agctttgggc gttgcactac ttgataaaaa caaacagcct    480
attccgcccg gtggcattca tttgcaagaa ctagcctaca ttgatgccag caaccttaat    540
ccaaagctga aaacattca attccaaata gcctgcgacg tcacgaatcc acttcttgga     600
gaaaacggag ctaccttcgt tttcggtgct caaaaaggcg caactcccga aatgctcgtt    660
caactagagc atgccatgca gaactacggg gcaaaaatcg atcaattttc atctcaaaaa    720
atcactacaa aaaaggagc cggagccgcc ggtggtatcg ctgccggact aatgactttc     780
ctaaatgcag acgtattaag cggttcagct cttgttatgg aactttctaa tatgaaggat    840
aaaatgaaag atgcggatat cgtcattgtt ggcgaaggac gaatggacca gcaatcgatg    900
atggggaaaa ttcctgttca aatcgctcaa gaagctaaaa acaaggttg tttcgtccta     960 gcaatcgtcg gtagccttgc actcgaaaac aatatcgccc aacaacacgg tatcgatgcg  1020
```
ttcttcccaa acatcccaga aataacagat ttacccactc ttttcgaaaa tacaacaaag   1080
aacctcgaac gcacggcgga aaacattgcc aaattaactt taattggcaa ataa         1134

<210> SEQ ID NO 23
<211> LENGTH: 1134
<212> TYPE: DNA
<213> ORGANISM: Listeria monocytogenes

<400> SEQUENCE: 23
atgaaaatcg tcatcgcacc tgattcattc aaagagagcg ccactgctgt tgaagtagca     60
aatgctataa aaaaggctg gactaaagca cgtccagccg atcaaattag ccttgcccct    120
gtttctgacg ggggtgaggg ttttcttact gttttaagtg agtcttccga ggtggaattg    180
tttcaagcag aagtaaccaa cctaaatggt cacaaaataa cggcctccta cggtattctc    240
gctagccaag aaactgcgat tatcgagtcc gccaacacga ttggattaga tttaatccca    300
gccgtagacc gtaatccagc ttacgcgagc tctaaaggcg tcggtgaact aattttggcg    360
gcactgaatc acaacgtcaa aaaaatcatt atcggccttg gtggaagtgg cacaaacgat    420
ggcggcgctg gctaatcca agctttgggc gttgcactac ttgataaaaa caaacagcct    480
attccgcccg gtggcattca tttgcaagaa ctagcttaca ttgatgccag caaccttaat    540
ccaaagctga aaacattca attccaaata gcctgcgacg tcacgaatcc acttcttgga    600
gaaaacggcg ctaccttcgt tttcggtgct caaaaaggcg caactcccga atgctcgtt    660 caactagagc gcgccatgca gaactacgga gcaaaactcg atcaattttc atctcaaaaa    720
atcactacaa aaaaggagc cggagccgct ggtggtatcg ctgccggact aatgactttc    780
ctaaatgcag acgtgttaag cggttcagct ctagttatgg aactttctaa tatgaaggat    840
aaaatgaaag atgcggatat cgttattgtt ggtgaaggac gaatggacaa gcaatcgatg    900
atggggaaaa tccctgttca aattgctcaa gaagctaaaa acaaggttg tttcgtccta    960 gcaatcgtcg gtagccttgc actcgaaaac aatatcgccc aacaacacgg tatcgatgcg   1020
tttttcccaa acatcccaga aataacagat ttacccactc ttttcgaaaa tacaacaaag   1080
aacctcgaac gcacggcgga aaacattgcc aaactaactt taattggcaa ataa         1134

<210> SEQ ID NO 24
<211> LENGTH: 1134
<212> TYPE: DNA
<213> ORGANISM: Listeria monocytogenes

<400> SEQUENCE: 24
atgaaaatcg tcatcgcacc tgattcattc aaagagagcg ccactgctgt tgaagtagca     60
aatgctataa aaaaggctg gactaaagca cgtccagccg atcaaattag ccttgcccct    120
gtttctgacg ggggtgaggg ttttcttact gttttaagtg agtcttccga ggtggaattg    180
tttcaagcag aagtaaccaa cctaaatggt cacaaaataa cggcctccta cggtattctc    240
gctagccaag aaactgcaat tatcgagtcc gctaacacga ttggattaga tttaatccca    300
gccgtagacc gcaatccagc ttacgcgagc tctaaaggcg tcggtgaact aattttggcg    360
gcactgaatc acaacgtcaa aaaaatcatt atcggccttg gtggaagtgg cacaaacgat    420
ggcggcgctg gctaatcca agctttgggc gttgcactac ttgataaaaa caaacagcct    480
attccgcccg gtggcattca tttgcaagaa ctagcttaca ttgatgccag caaccttaat    540
ccaaagctga aaacattca attccaaata gcctgcgacg tcacgaatcc acttcttgga    600

```
gaaaacggcg ctaccttcgt tttcggtgct caaaaaggcg caactcccga aatgctcgtt    660
caactagagc gcgccatgca gaactacgga gcaaaactcg atcaattttc atctcaaaaa    720
atcactacaa aaaaggagc cggagccgct ggtggtatcg ctgccggact aatgactttc     780
ctaaatgcag acgtgttaag cggttcagct ctagttatgg aactttctaa tatgaaggat    840
aaaatgaaag atgcggatat cgttattgtt ggtgaaggac gaatggacaa gcaatcgatg    900
atggggaaaa tccctgttca aattgctcaa gaagctaaaa acaaggttg tttcgtccta     960 gcaatcgtcg gtagccttgc actcgaaaac aatatcgccc aacaacacgg tatcgatgcg   1020
tttttcccaa acatcccaga aataacagat ttacccactc ttttcgaaaa tacaacaaag   1080
aacctcgaac gcacggcgga aaacattgcc aaactaactt taattggcaa ataa          1134
```

<210> SEQ ID NO 25
<211> LENGTH: 1134
<212> TYPE: DNA
<213> ORGANISM: Listeria monocytogenes

<400> SEQUENCE: 25

```
atgaaaatcg tcatcgcacc tgattcattc aaagagagcg ccactgctgt tgaagtagca     60
aatgctataa aaaaaggctg gactaaagca cgtccagccg atcaaattag ccttgcccct   120
gtttctgacg ggggtgaggg ttttcttact gttttaagtg agtcttccga ggtggaattg   180
tttcaagcag aagtaaccaa cctaaatggt cacaaaataa cggcctccta cggtattctc   240
gctagccaag aaactgcaat tatcgagtcc gctaacacga ttggattaga tttaatccca   300
gccgtagacc gcaatccagc ttacgcgagc tctaaaggcg tcggtgaact tattttggcg   360
gcactgaatc acaacgtcaa aaaaatcatt atcggccttg gtggaagtgg cacaaacgat   420
ggcggcgctg gctaatcca gcttttgggc gttgcactac ttgataaaaa caaacagcct    480
attccgcccg gtggcattca tttgcaagaa ctagcttaca ttgatgccag caaccttaat   540
ccaaagctga aaacattca attccaaata gcctgcgacg tcacgaatcc acttcttgga    600
gaaaacggcg ctaccttcgt tttcggtgct caaaaaggcg caactcccga aatgctcgtt   660
caactagagc gcgccatgca gaactacgga gcaaaactcg atcaattttc atctcaaaaa   720
atcactacaa aaaaggagc cggagccgct ggtggtatcg ctgccggact aatgactttc    780
ctaaatgcat acgtgttaag cggttcagct ctagttatgg aactttctaa tatgaaggat   840
aaaatgaaag atgcggatat cgttattgtt ggtgaaggac gaatggacaa gcaatcgatg   900
atggggaaaa tccctgttca aattgctcaa gaagctaaaa acaaggttg tttcgtccta    960 gcaatcgtcg gtagccttgc actcgaaaac aatatcgccc aacaacacgg tatcgatgcg  1020
tttttcccaa acatcccaga aataacagat ttacccactc ttttcgaaaa tacaacaaag  1080
aacctcgaac gcacggcgga aaacattgcc aaactaactt taattggcaa ataa         1134
```

<210> SEQ ID NO 26
<211> LENGTH: 20
<212> TYPE: DNA
<213> ORGANISM: Artificial Sequence
<220> FEATURE:
<223> OTHER INFORMATION: primer LMO0084-F286A

<400> SEQUENCE: 26

```
agccgtccag aaagcatcaa                                                  20
```

<210> SEQ ID NO 27
<211> LENGTH: 20

```
<212> TYPE: DNA
<213> ORGANISM: Artificial Sequence
<220> FEATURE:
<223> OTHER INFORMATION: primer LMO0084-F286B

<400> SEQUENCE: 27
agccgcccag aaagtctcaa                                          20

<210> SEQ ID NO 28
<211> LENGTH: 20
<212> TYPE: DNA
<213> ORGANISM: Artificial Sequence
<220> FEATURE:
<223> OTHER INFORMATION: primer LMO0084-F281A

<400> SEQUENCE: 28
tcgatagccg tccagaaagc                                          20

<210> SEQ ID NO 29
<211> LENGTH: 20
<212> TYPE: DNA
<213> ORGANISM: Artificial Sequence
<220> FEATURE:
<223> OTHER INFORMATION: primer LMO0084-F281B

<400> SEQUENCE: 29
ttgatagccg cccagaaagt                                          20

<210> SEQ ID NO 30
<211> LENGTH: 20
<212> TYPE: DNA
<213> ORGANISM: Artificial Sequence
<220> FEATURE:
<223> OTHER INFORMATION: primer LMO0084-R757A

<400> SEQUENCE: 30
gctcgtcggc gatttctttc                                          20

<210> SEQ ID NO 31
<211> LENGTH: 20
<212> TYPE: DNA
<213> ORGANISM: Artificial Sequence
<220> FEATURE:
<223> OTHER INFORMATION: primer LMO0084-R757B

<400> SEQUENCE: 31
gctcgtcggc tatttctttc                                          20

<210> SEQ ID NO 32
<211> LENGTH: 20
<212> TYPE: DNA
<213> ORGANISM: Artificial Sequence
<220> FEATURE:
<223> OTHER INFORMATION: primer LMO2736-F8

<400> SEQUENCE: 32
tcgtcatcgc acctgattca                                          20

<210> SEQ ID NO 33
<211> LENGTH: 20
<212> TYPE: DNA
<213> ORGANISM: Artificial Sequence
<220> FEATURE:
<223> OTHER INFORMATION: primer LMO2736-F222

<400> SEQUENCE: 33
```

```
ggcctcctac ggtattcacg                                               20

<210> SEQ ID NO 34
<211> LENGTH: 20
<212> TYPE: DNA
<213> ORGANISM: Artificial Sequence
<220> FEATURE:
<223> OTHER INFORMATION: primer LMO2736-F488

<400> SEQUENCE: 34
ccggtggcat tcatttgcaa                                               20

<210> SEQ ID NO 35
<211> LENGTH: 20
<212> TYPE: DNA
<213> ORGANISM: Artificial Sequence
<220> FEATURE:
<223> OTHER INFORMATION: primer LMO2736-F530

<400> SEQUENCE: 35
gcaaccttaa cccaaagctg                                               20

<210> SEQ ID NO 36
<211> LENGTH: 20
<212> TYPE: DNA
<213> ORGANISM: Artificial Sequence
<220> FEATURE:
<223> OTHER INFORMATION: primer LMO2736-F572

<400> SEQUENCE: 36
cctgtgacgt sacgaatcca                                               20

<210> SEQ ID NO 37
<211> LENGTH: 20
<212> TYPE: DNA
<213> ORGANISM: Artificial Sequence
<220> FEATURE:
<223> OTHER INFORMATION: primer LMO2736-R176

<400> SEQUENCE: 37
tccacctcgg aagactcact                                               20

<210> SEQ ID NO 38
<211> LENGTH: 20
<212> TYPE: DNA
<213> ORGANISM: Artificial Sequence
<220> FEATURE:
<223> OTHER INFORMATION: primer LMO2736-R591

<400> SEQUENCE: 38
tggattcgtc acgtcacagg                                               20

<210> SEQ ID NO 39
<211> LENGTH: 20
<212> TYPE: DNA
<213> ORGANISM: Artificial Sequence
<220> FEATURE:
<223> OTHER INFORMATION: primer LMO2736-R685

<400> SEQUENCE: 39
agttctgcat ggcgttctct                                               20

<210> SEQ ID NO 40
<211> LENGTH: 20
<212> TYPE: DNA
<213> ORGANISM: Artificial Sequence
```

```
<220> FEATURE:
<223> OTHER INFORMATION: primer LMO2736-R771

<400> SEQUENCE: 40
tagtccagca gcgataccac                                               20

<210> SEQ ID NO 41
<211> LENGTH: 20
<212> TYPE: DNA
<213> ORGANISM: Artificial Sequence
<220> FEATURE:
<223> OTHER INFORMATION: primer LMO2736-R992

<400> SEQUENCE: 41
ttgttttcga gtgcaaggct                                               20

<210> SEQ ID NO 42
<211> LENGTH: 20
<212> TYPE: DNA
<213> ORGANISM: Artificial Sequence
<220> FEATURE:
<223> OTHER INFORMATION: primer LMO84 F3

<400> SEQUENCE: 42
aaatgattga agtcgtacgc                                               20

<210> SEQ ID NO 43
<211> LENGTH: 21
<212> TYPE: DNA
<213> ORGANISM: Artificial Sequence
<220> FEATURE:
<223> OTHER INFORMATION: primer LMO84 B3

<400> SEQUENCE: 43
gcaacctctt caattgggat a                                             21

<210> SEQ ID NO 44
<211> LENGTH: 40
<212> TYPE: DNA
<213> ORGANISM: Artificial Sequence
<220> FEATURE:
<223> OTHER INFORMATION: primer LMO84 FIP

<400> SEQUENCE: 44
ctaaagcttc tccgacaagt tcaatggatg cagggattac                         40

<210> SEQ ID NO 45
<211> LENGTH: 42
<212> TYPE: DNA
<213> ORGANISM: Artificial Sequence
<220> FEATURE:
<223> OTHER INFORMATION: primer LMO84 BIP

<400> SEQUENCE: 45
agaaaccatg ttcaaattgc aacagctttc tggacggcta tc                      42

<210> SEQ ID NO 46
<211> LENGTH: 20
<212> TYPE: DNA
<213> ORGANISM: Artificial Sequence
<220> FEATURE:
<223> OTHER INFORMATION: primer LMO2736-1 F3

<400> SEQUENCE: 46
gaactagcct acattgatgc                                               20
```

<210> SEQ ID NO 47
<211> LENGTH: 21
<212> TYPE: DNA
<213> ORGANISM: Artificial Sequence
<220> FEATURE:
<223> OTHER INFORMATION: primer LMO2736-1 B3

<400> SEQUENCE: 47
ttgaaccgct taataagtct g                                    21

<210> SEQ ID NO 48
<211> LENGTH: 39
<212> TYPE: DNA
<213> ORGANISM: Artificial Sequence
<220> FEATURE:
<223> OTHER INFORMATION: primer LMO2736-1 FIP

<400> SEQUENCE: 48
ttcgtcacgt cacaggctat cagcaacctt aacccaaag                 39

<210> SEQ ID NO 49
<211> LENGTH: 41
<212> TYPE: DNA
<213> ORGANISM: Artificial Sequence
<220> FEATURE:
<223> OTHER INFORMATION: primer LMO2736-1 BIP

<400> SEQUENCE: 49
ggagcaaaac tcgaccaatt ttcgtccagc agcgatacca c              41

<210> SEQ ID NO 50
<211> LENGTH: 22
<212> TYPE: DNA
<213> ORGANISM: Artificial Sequence
<220> FEATURE:
<223> OTHER INFORMATION: primer LMO2736-2 F3

<400> SEQUENCE: 50
caagaactag cctacattga tg                                   22

<210> SEQ ID NO 51
<211> LENGTH: 21
<212> TYPE: DNA
<213> ORGANISM: Artificial Sequence
<220> FEATURE:
<223> OTHER INFORMATION: primer LMO2736-2 B3

<400> SEQUENCE: 51
tctgcattta ggaaggtcat t                                    21

<210> SEQ ID NO 52
<211> LENGTH: 40
<212> TYPE: DNA
<213> ORGANISM: Artificial Sequence
<220> FEATURE:
<223> OTHER INFORMATION: primer LMO2736-2 FIP

<400> SEQUENCE: 52
ttcgtcacgt cacaggctat cagcaacctt aacccaaagc                40

<210> SEQ ID NO 53
<211> LENGTH: 41
<212> TYPE: DNA
<213> ORGANISM: Artificial Sequence
<220> FEATURE:
<223> OTHER INFORMATION: primer LMO2736-2 BIP

```
<400> SEQUENCE: 53
ggagcaaaac tcgaccaatt ttcgtccagc agcgatacca c                    41

<210> SEQ ID NO 54
<211> LENGTH: 21
<212> TYPE: DNA
<213> ORGANISM: Artificial Sequence
<220> FEATURE:
<223> OTHER INFORMATION: primer LMO2736-10 F3

<400> SEQUENCE: 54
gtggcattca tttgcaagaa c                                          21

<210> SEQ ID NO 55
<211> LENGTH: 22
<212> TYPE: DNA
<213> ORGANISM: Artificial Sequence
<220> FEATURE:
<223> OTHER INFORMATION: primer LMO2736-10 B3

<400> SEQUENCE: 55
gagctgaacc gcttaataag tc                                         22

<210> SEQ ID NO 56
<211> LENGTH: 49
<212> TYPE: DNA
<213> ORGANISM: Artificial Sequence
<220> FEATURE:
<223> OTHER INFORMATION: primer LMO2736-10 FIP

<400> SEQUENCE: 56
gaagtggatt cgtcacgtca caggctacat tgatgccagc aaccttaac            49

<210> SEQ ID NO 57
<211> LENGTH: 43
<212> TYPE: DNA
<213> ORGANISM: Artificial Sequence
<220> FEATURE:
<223> OTHER INFORMATION: primer LMO2736-10 BIP

<400> SEQUENCE: 57
ctcgaccaat tttcttctca aaaaatcacc accagcggct ccg                  43

<210> SEQ ID NO 58
<211> LENGTH: 19
<212> TYPE: DNA
<213> ORGANISM: Artificial Sequence
<220> FEATURE:
<223> OTHER INFORMATION: F2 sequence of LMO84 FIP

<400> SEQUENCE: 58
caatggatgc agggattac                                             19

<210> SEQ ID NO 59
<211> LENGTH: 18
<212> TYPE: DNA
<213> ORGANISM: Artificial Sequence
<220> FEATURE:
<223> OTHER INFORMATION: B2 sequence of LMO84 BIP

<400> SEQUENCE: 59
gctttctgga cggctatc                                              18

<210> SEQ ID NO 60
```

```
<211> LENGTH: 19
<212> TYPE: DNA
<213> ORGANISM: Artificial Sequence
<220> FEATURE:
<223> OTHER INFORMATION: F2 sequence of LMO2736-1 FIP

<400> SEQUENCE: 60
cagcaacctt aacccaaag                                              19

<210> SEQ ID NO 61
<211> LENGTH: 18
<212> TYPE: DNA
<213> ORGANISM: Artificial Sequence
<220> FEATURE:
<223> OTHER INFORMATION: B2 sequence of LMO2736-1 BIP and LMO2736-2 BIP

<400> SEQUENCE: 61
gtccagcagc gataccac                                               18

<210> SEQ ID NO 62
<211> LENGTH: 20
<212> TYPE: DNA
<213> ORGANISM: Artificial Sequence
<220> FEATURE:
<223> OTHER INFORMATION: F2 sequence of LMO2736-2 FIP

<400> SEQUENCE: 62
cagcaacctt aacccaaagc                                             20

<210> SEQ ID NO 63
<211> LENGTH: 25
<212> TYPE: DNA
<213> ORGANISM: Artificial Sequence
<220> FEATURE:
<223> OTHER INFORMATION: F2 sequence of LMO2736-10 FIP

<400> SEQUENCE: 63
ctacattgat gccagcaacc ttaac                                       25

<210> SEQ ID NO 64
<211> LENGTH: 15
<212> TYPE: DNA
<213> ORGANISM: Artificial Sequence
<220> FEATURE:
<223> OTHER INFORMATION: B2 sequence of LMO2736-10 BIP

<400> SEQUENCE: 64
ccaccagcgg ctccg                                                  15

<210> SEQ ID NO 65
<211> LENGTH: 21
<212> TYPE: DNA
<213> ORGANISM: Artificial Sequence
<220> FEATURE:
<223> OTHER INFORMATION: primer LMO0833 F329

<400> SEQUENCE: 65
ggaaagcaat tgtccactcg a                                           21

<210> SEQ ID NO 66
<211> LENGTH: 20
<212> TYPE: DNA
<213> ORGANISM: Artificial Sequence
<220> FEATURE:
<223> OTHER INFORMATION: primer LMO0833 R610

<400> SEQUENCE: 66
```
tgttggtgag tagcgtggaa 20

<210> SEQ ID NO 67
<211> LENGTH: 20
<212> TYPE: DNA
<213> ORGANISM: Artificial Sequence
<220> FEATURE:
<223> OTHER INFORMATION: mixed primer LMO0084-F286/M

<400> SEQUENCE: 67
agccgyccag aaagymtcaa 20

<210> SEQ ID NO 68
<211> LENGTH: 20
<212> TYPE: DNA
<213> ORGANISM: Artificial Sequence
<220> FEATURE:
<223> OTHER INFORMATION: mixed primer LMO0084-F281/M

<400> SEQUENCE: 68
tygatagccg yccagaaagy 20

<210> SEQ ID NO 69
<211> LENGTH: 20
<212> TYPE: DNA
<213> ORGANISM: Artificial Sequence
<220> FEATURE:
<223> OTHER INFORMATION: mixed primer LMO0084-R757/M

<400> SEQUENCE: 69
gctcgtcrgc katttctttc 20

<210> SEQ ID NO 70
<211> LENGTH: 20
<212> TYPE: DNA
<213> ORGANISM: Artificial Sequence
<220> FEATURE:
<223> OTHER INFORMATION: mixed primer LMO2736-F222/M

<400> SEQUENCE: 70
ggccycctac ggtattcwcr 20

<210> SEQ ID NO 71
<211> LENGTH: 20
<212> TYPE: DNA
<213> ORGANISM: Artificial Sequence
<220> FEATURE:
<223> OTHER INFORMATION: mixed primer LMO2736-F488/M

<400> SEQUENCE: 71
ccggyggyat tcatttgcaa 20

<210> SEQ ID NO 72
<211> LENGTH: 20
<212> TYPE: DNA
<213> ORGANISM: Artificial Sequence
<220> FEATURE:
<223> OTHER INFORMATION: mixed primer LMO2736-F530/M

<400> SEQUENCE: 72
gcaaycttaa yccaaagctg 20

<210> SEQ ID NO 73
<211> LENGTH: 20
<212> TYPE: DNA

```
<213> ORGANISM: Artificial Sequence
<220> FEATURE:
<223> OTHER INFORMATION: mixed primer LMO2736-F572/M

<400> SEQUENCE: 73
cctgygacgt sacgaatcca                                               20

<210> SEQ ID NO 74
<211> LENGTH: 20
<212> TYPE: DNA
<213> ORGANISM: Artificial Sequence
<220> FEATURE:
<223> OTHER INFORMATION: mixed primer LMO2736-R591/M

<400> SEQUENCE: 74
tggattcgts acgtcrcagg                                               20

<210> SEQ ID NO 75
<211> LENGTH: 20
<212> TYPE: DNA
<213> ORGANISM: Artificial Sequence
<220> FEATURE:
<223> OTHER INFORMATION: mixed primer LMO2736-R685/M

<400> SEQUENCE: 75
agttctgcat ggcrykctct                                               20

<210> SEQ ID NO 76
<211> LENGTH: 20
<212> TYPE: DNA
<213> ORGANISM: Artificial Sequence
<220> FEATURE:
<223> OTHER INFORMATION: mixed primer LMO2736-R771/M

<400> SEQUENCE: 76
tagtccrgca gcgataccac                                               20

<210> SEQ ID NO 77
<211> LENGTH: 23
<212> TYPE: DNA
<213> ORGANISM: Artificial Sequence
<220> FEATURE:
<223> OTHER INFORMATION: oligonucleotide sequence of probe 0084TMP366-
      389

<400> SEQUENCE: 77
tattacattc atagaattga ccc                                           23

<210> SEQ ID NO 78
<211> LENGTH: 23
<212> TYPE: DNA
<213> ORGANISM: Artificial Sequence
<220> FEATURE:
<223> OTHER INFORMATION: oligonucleotide sequence of probe 0084TMP535-
      558(TA)

<400> SEQUENCE: 78
atctggtggc gagaagctga aaa                                           23

<210> SEQ ID NO 79
<211> LENGTH: 23
<212> TYPE: DNA
<213> ORGANISM: Artificial Sequence
<220> FEATURE:
<223> OTHER INFORMATION: oligonucleotide sequence of probe 0084TMP535-
      558(CC)
```

```
<400> SEQUENCE: 79
atctggtggc gagaagccga aca                                              23

<210> SEQ ID NO 80
<211> LENGTH: 26
<212> TYPE: DNA
<213> ORGANISM: Artificial Sequence
<220> FEATURE:
<223> OTHER INFORMATION: oligonucleotide sequence of probe 0084TMP686-
      711

<400> SEQUENCE: 80
taccaagatt ccaaaaagaa gccatg                                           26

<210> SEQ ID NO 81
<211> LENGTH: 20
<212> TYPE: DNA
<213> ORGANISM: Artificial Sequence
<220> FEATURE:
<223> OTHER INFORMATION: oligonucleotide sequence of probe 2736TMP70-89

<400> SEQUENCE: 81
aaaaaaggct ggactaaagc                                                  20

<210> SEQ ID NO 82
<211> LENGTH: 20
<212> TYPE: DNA
<213> ORGANISM: Artificial Sequence
<220> FEATURE:
<223> OTHER INFORMATION: oligonucleotide sequence of probe 2736TMP372-
      393

<400> SEQUENCE: 82
acgtcaaaaa aatcattatc                                                  20

<210> SEQ ID NO 83
<211> LENGTH: 29
<212> TYPE: DNA
<213> ORGANISM: Artificial Sequence
<220> FEATURE:
<223> OTHER INFORMATION: oligonucleotide sequence of probe 2736TMP619-
      647(GG)

<400> SEQUENCE: 83
gttttcggtg ctcaaaaagg ggcaagtcc                                        29

<210> SEQ ID NO 84
<211> LENGTH: 29
<212> TYPE: DNA
<213> ORGANISM: Artificial Sequence
<220> FEATURE:
<223> OTHER INFORMATION: oligonucleotide sequence of probe 2736TMP619-
      647(CC)

<400> SEQUENCE: 84
gttttcggtg ctcaaaaagg cgcaactcc                                        29

<210> SEQ ID NO 85
<211> LENGTH: 23
<212> TYPE: DNA
<213> ORGANISM: Artificial Sequence
<220> FEATURE:
<223> OTHER INFORMATION: oligonucleotide sequence of mixed probe
      (0084TMP535-558(TA) + 0084TMP535-558(CC))
<220> FEATURE:
<221> NAME/KEY: misc_feature
<222> LOCATION: (18)..(22)
```

```
<223> OTHER INFORMATION: ngaan is tgaaa or cgaac

<400> SEQUENCE: 85
atctggtggc gagaagcnga ana                                           23

<210> SEQ ID NO 86
<211> LENGTH: 29
<212> TYPE: DNA
<213> ORGANISM: Artificial Sequence
<220> FEATURE:
<223> OTHER INFORMATION: oligonucleotide sequence of mixed probe
      (2736TMP619-647(GG) + 2736TMP619-647(CC))
<220> FEATURE:
<221> NAME/KEY: misc_feature
<222> LOCATION: (21)..(26)
<223> OTHER INFORMATION: ngcaan is ggcaag or cgcaac

<400> SEQUENCE: 86
gttttcggtg ctcaaaaagg ngcaantcc                                     29
```